US010202347B2

(12) United States Patent
Kawada et al.

(10) Patent No.: US 10,202,347 B2
(45) Date of Patent: *Feb. 12, 2019

(54) COMPOUND, PRODUCTION METHOD THEREFOR, AND USE OF SAID COMPOUND

(71) Applicant: MICROBIAL CHEMISTRY RESEARCH FOUNDATION, Tokyo (JP)

(72) Inventors: Manabu Kawada, Tokyo (JP); Hikaru Abe, Tokyo (JP); Takumi Watanabe, Tokyo (JP); Hiroyuki Inoue, Tokyo (JP); Shun-ichi Ohba, Tokyo (JP); Chigusa Hayashi, Tokyo (JP); Masayuki Igarashi, Tokyo (JP)

(73) Assignee: MICROBIAL CHEMISTRY RESEARCH FOUNDATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/817,090

(22) Filed: Nov. 17, 2017

(65) Prior Publication Data

US 2018/0093954 A1    Apr. 5, 2018

Related U.S. Application Data

(63) Continuation of application No. 15/446,769, filed on Mar. 1, 2017, now Pat. No. 9,850,211, which is a continuation of application No. 14/770,492, filed as application No. PCT/JP2014/054268 on Feb. 24, 2014, now Pat. No. 9,617,217.

(30) Foreign Application Priority Data

Feb. 26, 2013 (JP) .................................. 2013-035732

(51) Int. Cl.
  *C07D 215/233* (2006.01)
  *A61P 31/04* (2006.01)
  *A61P 35/00* (2006.01)

(52) U.S. Cl.
  CPC .......... *C07D 215/233* (2013.01); *A61P 31/04* (2018.01); *A61P 35/00* (2018.01)

(58) Field of Classification Search
  CPC ....... C07D 215/233; A61P 31/04; A61P 35/00
  See application file for complete search history.

(56) References Cited

U.S. PATENT DOCUMENTS

| | | | |
|---|---|---|---|
| 5,942,619 A | 8/1999 | Dekker et al. | |
| 6,080,757 A | 6/2000 | Brown | |
| 9,617,217 B2* | 4/2017 | Kawada | C07D 215/233 |
| 9,850,211 B2* | 12/2017 | Kawada | C07D 215/233 |
| 2007/0037752 A1 | 2/2007 | Ansorge et al. | |

FOREIGN PATENT DOCUMENTS

| | | |
|---|---|---|
| CN | 1897928 A | 1/2007 |
| EP | 0811613 A1 | 12/1997 |
| JP | 2001-097866 A | 4/2001 |
| WO | WO 2009/060209 A1 | 5/2009 |

OTHER PUBLICATIONS

Abe, Tetrahedron, VOl 69, 7608-7617, 2013. (Year: 2013).*
International Search Report, dated May 27, 2014, for corresponding International Patent Application No. PCT/JP2014/054268 (With English Translation).
Written Opinion, dated May 27, 2014, for corresponding International Patent Application No. PCT/JP2014/054268. (With English Translation).
International Preliminary Report on Patentability, dated Sep. 1, 2015, for corresponding International Patent Application No. PCT/JP2014/054268.
Reil et al., "Quinolones and their N-Oxides as inhibitors of Mitochondrial Complexes I and III", Biochimica et Biophysica Acta, Jan. 16, 1997, pp. 291 to 298, vol. 1318—issue Nos. 1 & 2, Elsevier Science B.V.
Kawada et al., "Insulin-like Growth Factor I Secreted from Prostrate Stromal Cells Mediates Tumor-Stromal Cell Interactions of Prostrate Cancer", Cancer Research, Apr. 15, 2006, pp. 4419 to 4425, vol. 66—issue No. 8, American Association for Cancer Research.
Supplementary Partial European Search Report dated Jul. 6, 2016, for corresponding European Application No. 14757424.8.
Dekker et al., "New Quinolone Compounds from *Pseudonocardia* sp. with Selective and Potent Anti-Helicobacter pylori Activity: Taxonomy of Producing Strain, Fermentation, Isolation, Structural Elucidation and Biological Activities", The Journal of Antibiotics, Feb. 1998, pp. 145 to 152, vol. 51—issue No. 2.
Office Action dated Sep. 7, 2016, by the Patent Office of the People's Republic of China, for corresponding Patent Application No. CN 201480023381.3. (With English Translation).
Tang Yajuan et al., "Research Progress in Synthesis of Quinolinone Compounds and Anti-HIV Activity", Guangzhou Chemistry, Dec. 2009, vol. 34—issue No. 4, pp. 39 to 50. (Partial English Translation).
Non-Final Office Action mailed by the USPTO dated Jul. 1, 2016, for corresponding U.S. Appl. No. 14/770,492.
Abe et al., "Structure-activity relationship study of intervenolin derivatives: synthesis, antitumor, and anti-Helicobacter pylori activities", Tetrahedron, 2013, pp. 7608 to 7617, vol. 69, Elsevier Ltd.
Reil et al., "Quinolones and their N-Oxides as inhibitors of photosystem II and the cytochrome b6/f-complex", Biochimica et Biophysica Acta, 2001, pp. 127 to 132, vol. 1506, Elsevier Science B.V.
Reen et al., "Structure-function analysis of the C-3 position in analogues of microbial behavioural modulators HHQ and PQS", Organic and Biomolecular Chemistry, 2012, pp. 8903 to 8910, vol. 10, The Royal Society of Chemistry.
Moon et al., "Plant Growth Promoting and Fungicidal 4-Quinolinones From Pseudomonas Cepacia", Phytochemistry, May 1996, pp. 365 to 368, vol. 42—issue No. 2, Elsevier Science Ltd.

(Continued)

*Primary Examiner* — D Margaret M Seaman
(74) *Attorney, Agent, or Firm* — Pergament & Cepeda LLP; Milagros A. Cepeda; Edward D. Pergament

(57) ABSTRACT

The present application provides novel compounds having anti-cancer or anti-*Helicobacter pylori* activity, pharmaceutical compositions and method for producing and using the novel compound.

8 Claims, 2 Drawing Sheets

(56) References Cited

OTHER PUBLICATIONS

Kilani-Feki et al., "Corelation between synthesis variation of 2-alkylquinolones and the antifungal activity of a Burkholderia cepacia strain collection", World J Microbiol Biotechnol, 2012, pp. 275 to 281, vol. 28, Springer Science+Buisiness Media B.V.
Non-Final Office Action mailed by the USPTO dated May 3, 2017, for corresponding U.S. Appl. No. 15/446,769.
Office Action dated Dec. 7, 2018 by the Patent Office of the People's Republic of China (Chinese).
Office Action dated Dec. 7, 2018 by the Patent Office of the People's Republic of China (English).

* cited by examiner

COMPOUND, PRODUCTION METHOD THEREFOR, AND USE OF SAID COMPOUND

This application is a Continuation of U.S. patent application Ser. No. 15/446,769, filed on Mar. 1, 2017, which is a Continuation of U.S. patent application Ser. No. 14/770,492, filed on Aug. 26, 2015, which is a National Phase application under 35 U.S.C. 371 of International Application No. PCT/JP2014/054268, filed on Feb. 24, 2014, which claims priority to Japanese Application No. 2013-035732, filed on Feb. 26, 2013, all of which are hereby incorporated by reference in their entireties.

TECHNICAL FIELD

The present invention relates to a novel compound, a method for producing the same, and a composition, an anti-cancer agent, and an anti-*Helicobacter pylori* agent each containing the novel compound.

BACKGROUND ART

Tissue of cancer is not made from cancer cells only, but is made from a mixture of cancer cells and their surrounding normal tissue called stroma. The stroma is composed of a variety of factors such as blood vessels, extracellular matrix, and fibroblast-like cells (hereinafter may be referred to simply as "stromal cells") and has been elucidated to closely relate to proliferation of cancer. In particular, stromal cells in the stroma are known to control proliferation of cancer cells both positively and negatively via adhesion and/or secretory components (see, for example, Kawada, M., Inoue, H., Masuda, T., and Ikeda, D. Insulin-like growth factor-I secreted from prostate stromal cells mediates tumor-stromal cell interactions of the prostate cancer. Cancer Res. 66, 4419-4425 (2006)). Under such circumstances, exploration has been made for more useful, new anti-cancer agents, and it has been strongly demanded to rapidly provide them.

In stomach and duodenal disorders such as stomach ulcer and duodenal ulcer, some of them are known to be caused by *Helicobacter pylori*. In view of this, quinolone compounds have been proposed as compounds having anti-*Helicobacter pylori* activity (see, for example, Dekker, K. A., Inagaki, T., Gootz, T. D., Huang, L. H., Kojima, Y., Kohlbrenner, W. E., Matsunaga, Y., McGuirk, P. R., Nomura, E., Sakakibara, T., Sakemi, S., Suzuki, Y., Yamauchi, Y., and Kojima, N. New quinolone compounds from *Pseudonocardia* sp. with selective and potent anti-*Helicobacter pylori* activity: taxonomy of producing strain, fermentation, isolation, structural elucidation and biological activities. J. Antibiot. 51, 145-152 (1998), and U.S. Pat. No. 5,942,619). However, it cannot be said that the above proposed quinolone compounds are satisfactory in use as a pharmaceutical drug, and it has been demanded to provide new compounds having anti-*Helicobacter pylori* activity.

SUMMARY OF INVENTION

Technical Problem

The present invention has been made in view of the above existing technique, and aims to achieve the following object. That is, an object of the present invention is to provide a novel compound having excellent anti-cancer effects or excellent anti-*Helicobacter pylori* activity, a method for producing the novel compound, a compound-containing composition, anti-cancer agent, and anti-*Helicobacter pylori* agent utilizing the novel compound.

Solution to Problem

Means for solving the above problems are as follows.

In one aspect, the present application provides a compound expressed by any one of Structural Formulas (1) to (13) below:

Structural Formula (1)

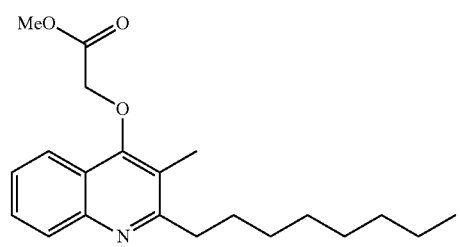

Structural Formula (2)

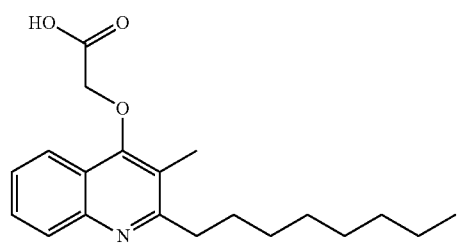

Structural Formula (3)

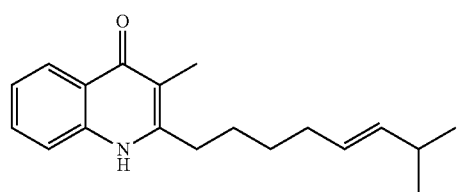

Structural Formula (4)

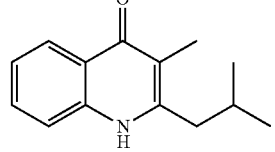

Structural Formula (5)

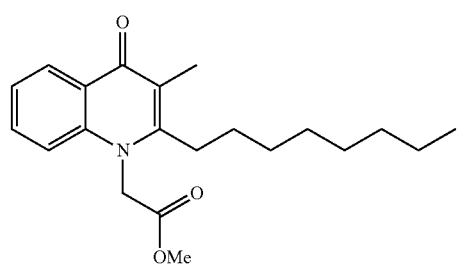

Structural Formula (6)

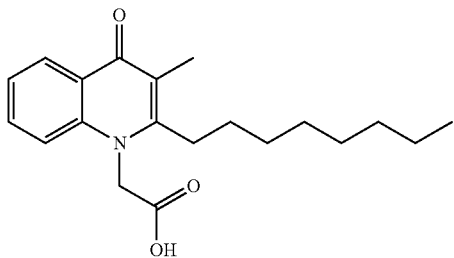

Structural Formula (7)

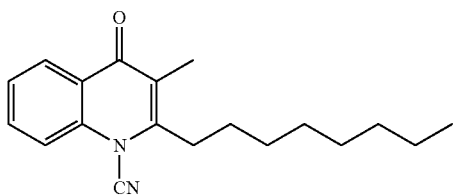

Structural Formula (8)

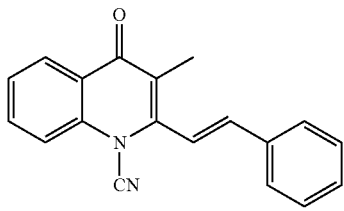

Structural Formula (9)

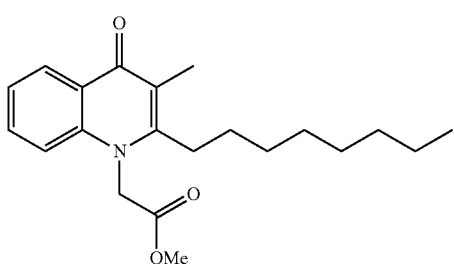

Structural Formula (10)

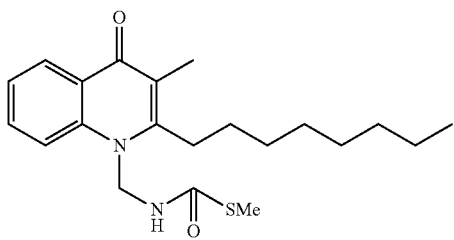

Structural Formula (11)

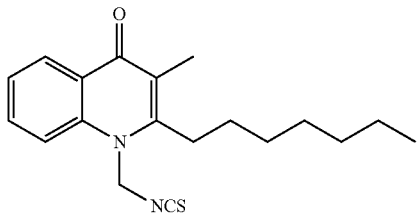

Structural Formula (12)

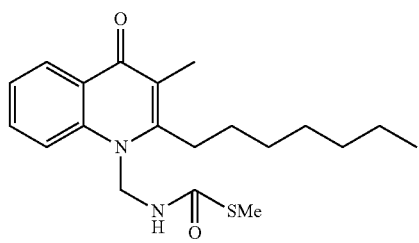

Structural Formula (13)

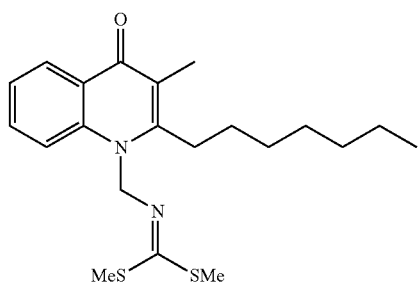

where in the Structural Formulas (1) to (13), Me denotes a methyl group.

In one aspect, the present invention provides a method for producing a compound expressed by any one of Structural Formulas (3), (4), and (8) below, the method including:

reacting a compound expressed by any one of Structural Formula (17), (18), and (19) below with a hydroxide of an alkali metal or a hydroxide of an alkaline earth metal, or both thereof:

Structural Formula (17)

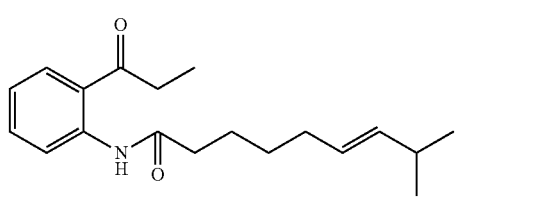

Structural Formula (3)

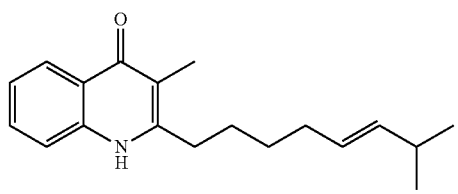

Structural Formula (18)

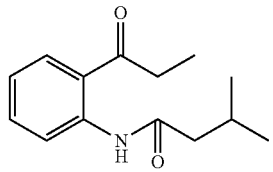

-continued

Structural Formula (4)
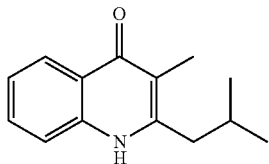

Structural Formula (19)
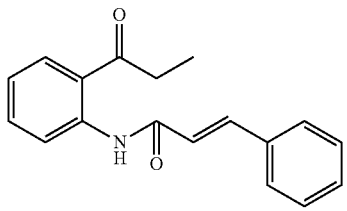

Structural Formula (8)
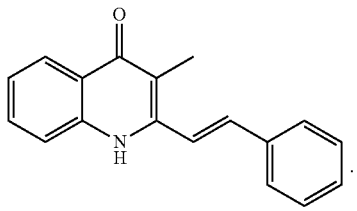

In one aspect, the present invention provides a method for producing a compound expressed by Structural Formula (5) below, the method including:

reacting a compound expressed by Structural Formula (21) below with an alkoxide of an alkali metal, a carbonic acid salt of an alkali metal or a hydride of an alkali metal, or any combination thereof, to thereby obtain a reaction product, and reacting the reaction product and methyl bromoacetate:

Structural Formula (21)
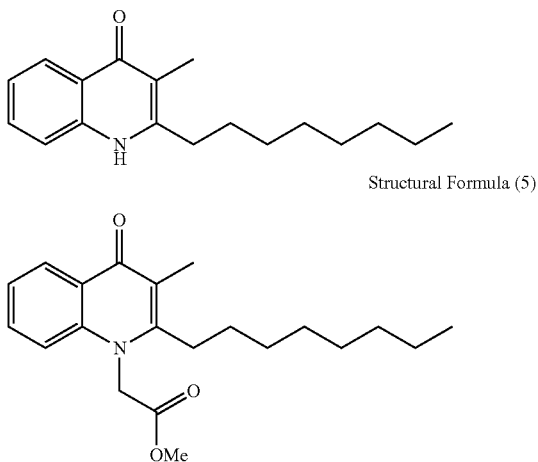

Structural Formula (5)

where in the Structural Formula (5), Me denotes a methyl group.

In one aspect, the present invention provides a method for producing a compound expressed by Structural Formula (6) below, the method including:

reacting a compound expressed by Structural Formula (5) below with a hydroxide of an alkali metal or a hydroxide of an alkaline earth metal, or both thereof, to thereby obtain a reaction product, and acidifying a pH of the reaction product:

Structural Formula (5)
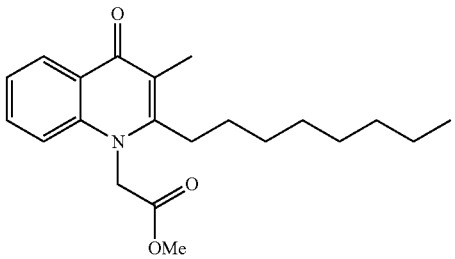

Structural Formula (6)
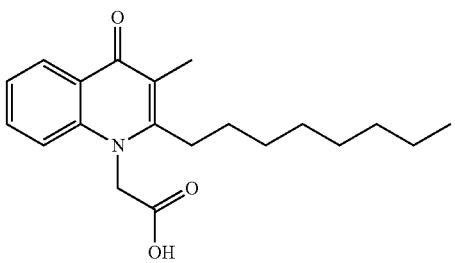

where in the Structural Formula (5), Me denotes a methyl group.

In one aspect, the present invention provides a method for producing a compound expressed by Structural Formula (1) below, the method including:

reacting a compound expressed by Structural Formula (21) below with a carbonic acid salt of an alkali metal or a hydride of an alkali metal, or both thereof, and methyl bromoacetate:

Structural Formula (21)
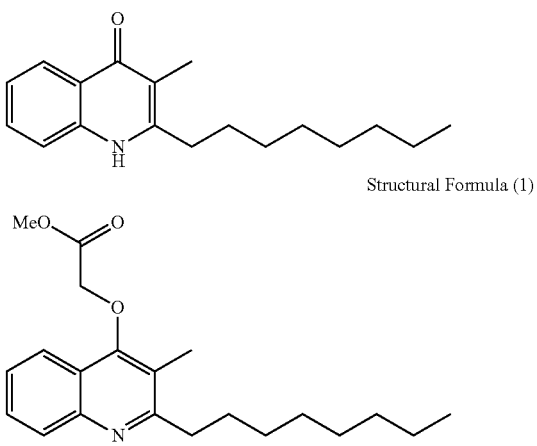

Structural Formula (1)

where in the Structural Formula (1), Me denotes a methyl group.

In one aspect, the present invention provides a method for producing a compound expressed by Structural Formula (2) below, the method including:

reacting a compound expressed by Structural Formula (1) below with a hydroxide of an alkali metal or a hydroxide of an alkaline earth metal, or both thereof, to thereby obtain a reaction product, and acidifying a pH of the reaction product:

Structural Formula (1)

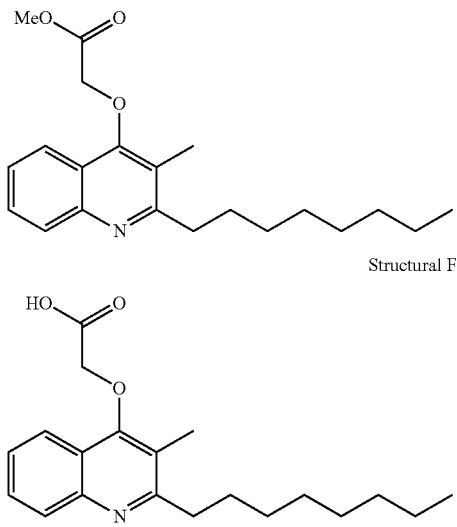

Structural Formula (2)

where in the Structural Formula (1), Me denotes a methyl group.

In one aspect, the present invention provides a method for producing a compound expressed by Structural Formula (7) below, the method including:

reacting a compound expressed by Structural Formula (21) below with an alkoxide of an alkali metal or a hydride of an alkali metal, or both thereof, to thereby obtain a reaction product, and reacting the reaction product and cyanogen bromide:

Structural Formula (21)

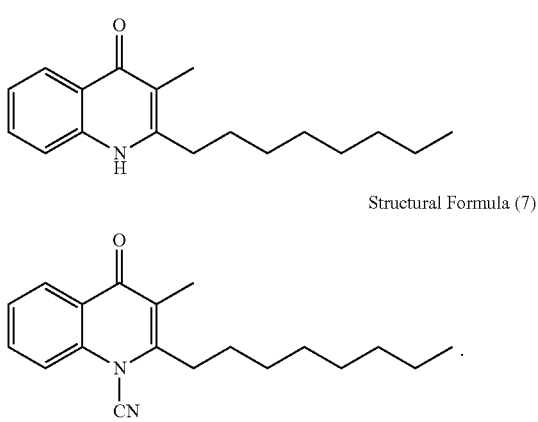

Structural Formula (7)

In one aspect, the present invention provides a method for producing a compound expressed by Structural Formula (9) below, the method including:

reacting a compound expressed by Structural Formula (6) below with a tertiary amine or a pyridine, or both thereof, diphenylphosphoryl azide, and sodium thiomethoxide:

Structural Formula (6)

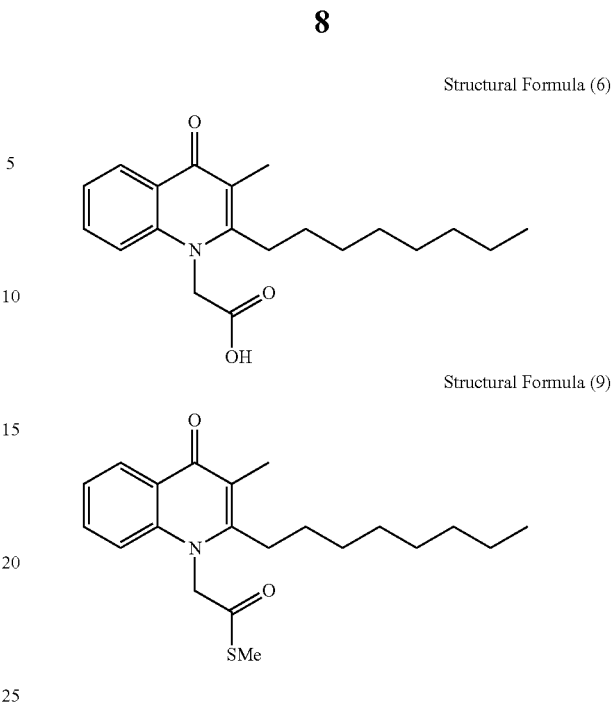

Structural Formula (9)

where in the Structural Formula (9), Me denotes a methyl group.

In one aspect, the present invention provides a method for producing a compound expressed by Structural Formula (10) below, the method including:

reacting a compound expressed by Structural Formula (6) below with a tertiary amine or a pyridine, or both thereof, and diphenylphosphoryl azide, to thereby obtain a reaction product, and reacting the reaction product and sodium thiomethoxide:

Structural Formula (6)

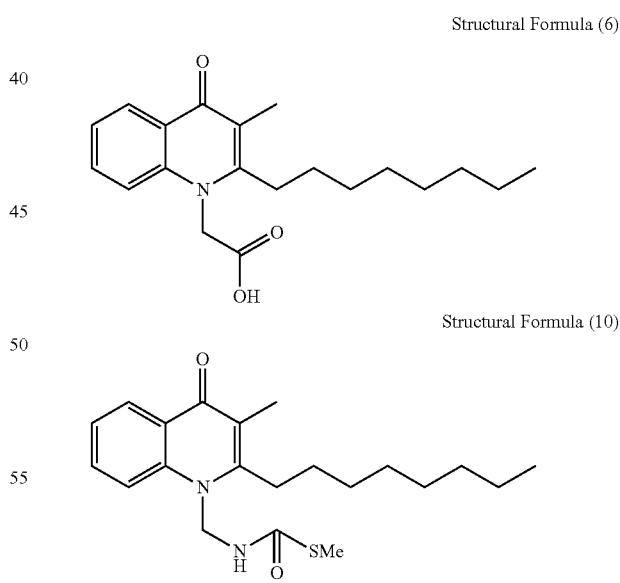

Structural Formula (10)

where in the Structural Formula (10), Me denotes a methyl group.

In one aspect, the present invention provides a method for producing a compound expressed by Structural Formula (11) below, the method including:

reacting a compound expressed by Structural Formula (20) below with an alkoxide of an alkali metal or a hydride of an alkali metal, or both thereof, to thereby obtain a reaction product, and reacting the reaction product and chloromethyl thiocyanate:

Structural Formula (20)

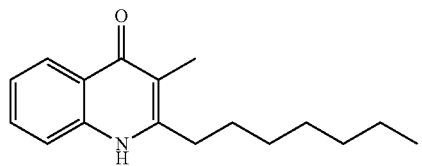

Structural Formula (11)

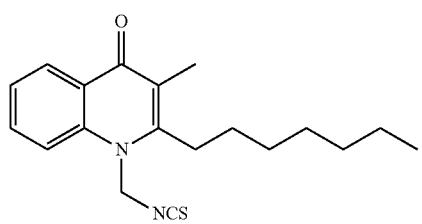

In one aspect, the present invention provides a method for producing a compound expressed by Structural Formula (12) below, the method including:

reacting a compound expressed by Structural Formula (11) below with sodium thiomethoxide in the presence of acetonitrile:

Structural Formula (11)

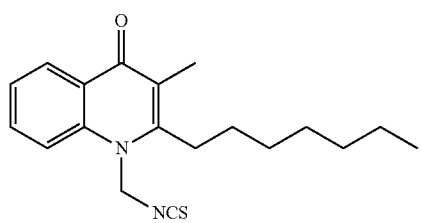

Structural Formula (12)

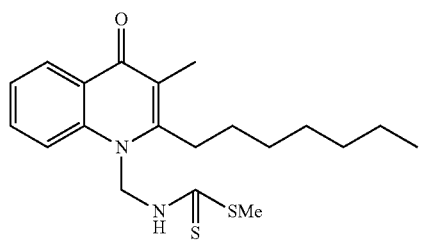

where in the Structural Formula (12), Me denotes a methyl group.

In one aspect, the present invention provides a method for producing a compound expressed by Structural Formula (13) below, the method including:

reacting a compound expressed by Structural Formula (11) below with sodium thiomethoxide in the presence of acetonitrile, to thereby obtain a reaction product, and reacting the reaction product and a methylating agent:

Structural Formula (11)

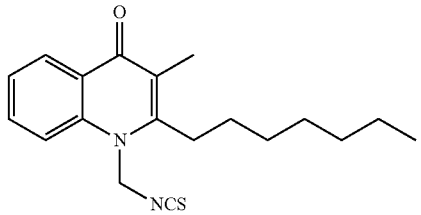

Structural Formula (13)

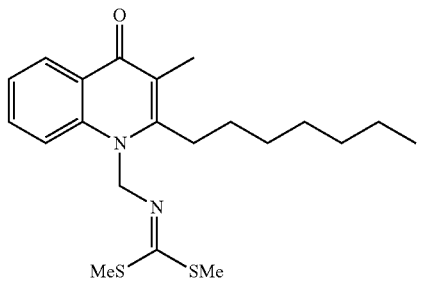

where in the Structural Formula (13), Me denotes a methyl group.

In one aspect, the present invention provides a pharmaceutical composition comprising a compound expressed by any one of Structural Formulas (1) to (13) of the present invention as shown above.

In one aspect, the present invention provides an anti-cancer agent comprising a compound expressed by any one of the Formulas (1) to (13) of the present invention as shown above.

In another aspect, the present invention provides an anti-*Helicobacter pylori* agent comprising a compound expressed by any one of the Formulas (1) to (13) of the present invention as shown above.

In another aspect, the present invention provides a method for preventing or treating cancer, the method including:

administering to an individual an anti-cancer agent comprising a compound expressed by any one of the Formulas (1) to (13) of the present invention as shown above.

In another aspect, the present invention provides a method for preventing or treating an infectious disease caused by *Helicobacter pylori*, the method including:

administering to an individual an anti-*Helicobacter pylori* agent comprising a compound expressed by any one of the Formulas (1) to (13) of the present invention as shown above.

In another aspect, the present invention provides a method for preventing or treating stomach and duodenal disorders caused by *Helicobacter pylori*, the method including:

administering to an individual an anti-*Helicobacter pylori* agent comprising a compound expressed by any one of the Formulas (1) to (13) of the present invention as shown above.

Advantageous Effects of Invention

According to the present invention, it is possible to achieve the above object and provide a novel compound having excellent anti-cancer effects or excellent anti-*Helicobacter pylori* activity, a method for producing the novel compound, a compound-containing composition, anti-cancer agent, and anti-*Helicobacter pylori* agent utilizing the novel compound.

DESCRIPTION OF EMBODIMENTS (Novel Compound)

Figure 1A:
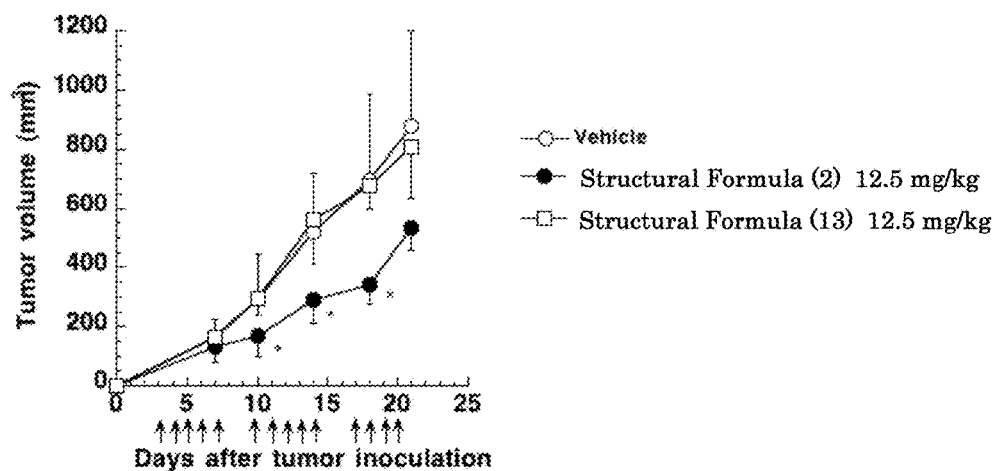
FIG. 1A is a graph of changes in tumor volume in Test Example 2-1.

A compound of the present invention is a compound expressed by any one of Structural Formulas (1) to (13) below, and is a novel compound found by the present inventors.

Structural Formula (1)
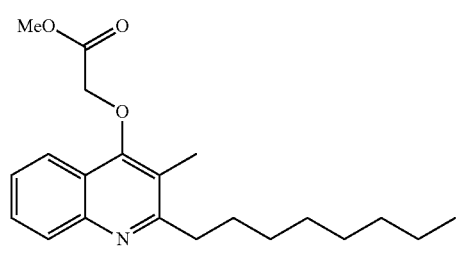

Structural Formula (2)
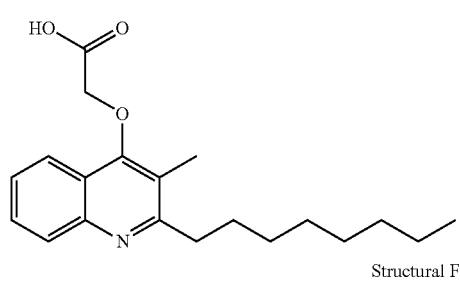

Structural Formula (3)
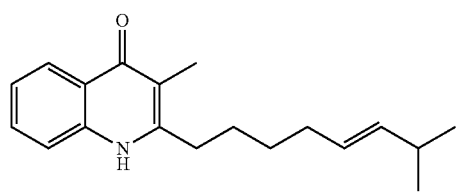

Structural Formula (4)
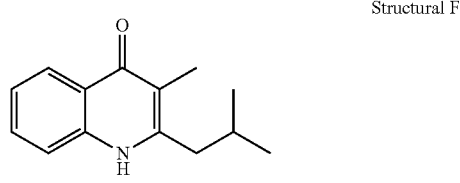

Structural Formula (5)
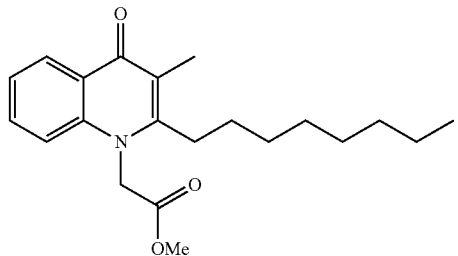

Structural Formula (6)
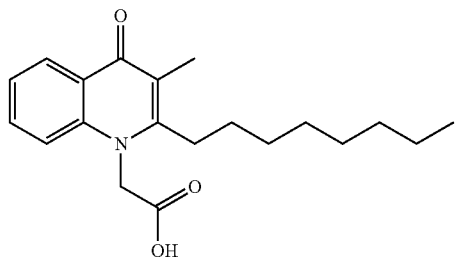

Structural Formula (7)
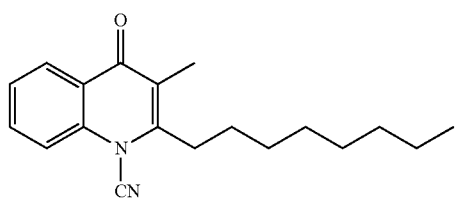

Structural Formula (8)
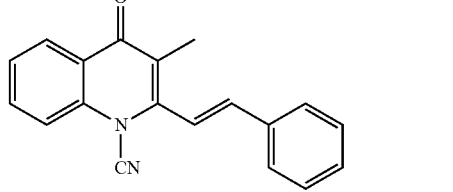

Structural Formula (9)
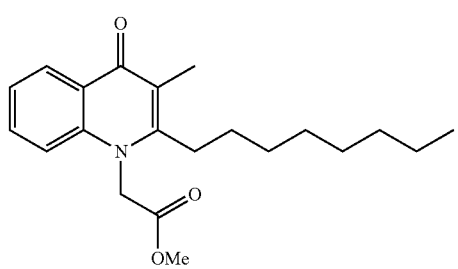

Structural Formula (10)
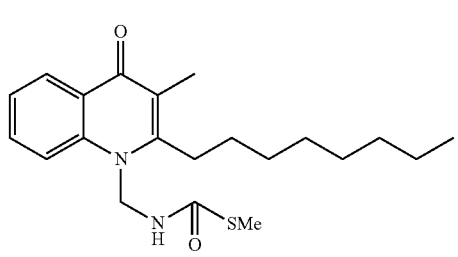

-continued

Structural Formula (11)

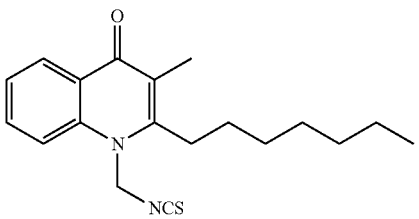

Structural Formula (12)

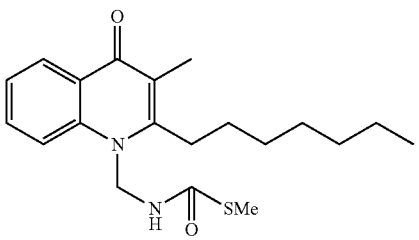

Structural Formula (13)

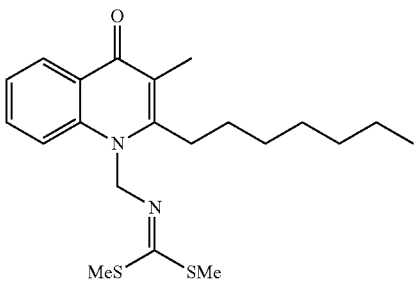

In the above Structural Formulas (1) to (13), Me denotes a methyl group.

Physico-Chemical Properties of the Compound Expressed by Structural Formula (1)

Physico-chemical properties of the compound expressed by Structural Formula (1) as follows.

(1) Appearance: colorless oily substance
(2) Molecular formula: $C_{21}H_{29}O_3N$
(3) High resolution mass spectrometry (HRESI-MS)(m/z):
   Found: 344.2221 $(M+H)^+$
   Calcd: 344.2220 (as $C_{21}H_{30}O_3N$)
(4) Infrared absorption spectrum:
   Peaks of infrared absorption measured by the KBr tablet method are as follows.
   $v_{max}(KBr)cm^{-1}$: 2953, 2925, 2854, 1765, 1618, 1596, 1437, 1123, 968, 768, 680
(5) Proton nuclear magnetic resonance spectrum (400 MHz, $CDCl_3$):
   δ=0.87 (3H, t, J=6.6), 1.20-1.48 (10H, m), 1.71 (2H, m), 2.43 (3H, s), 2.95 (2H, m), 3.86 (3H, s), 4.62 (2H, s), 7.47 (1H, ddd, J=8.2, 6.8, 1.1), 7.62 (1H, ddd, J=8.4, 6.8, 1.3), 8.00 (1H, d, J=8.4), 8.05 (1H, d, J=8.2)
(6) $^{13}C$ nuclear magnetic resonance spectrum (100 MHz, $CDCl_3$):
   δ=11.90, 14.08, 22.63, 28.99, 29.23, 29.49, 29.86, 31.83, 37.02, 52.32, 70.26, 120.85, 120.73, 121.39, 121.76, 125.73, 128.82, 128.85, 147.84, 159.03, 164.32, 168.95

Physico-Chemical Properties of the Compound Expressed by Structural Formula (2)

Physico-chemical properties of the compound expressed by Structural Formula (2) as follows.

(1) Appearance: white powder
(2) Melting point: 59° C.-62° C.
(3) Molecular formula: $C_{20}H_{27}O_3N$
(4) High resolution mass spectrometry (HRESI-MS)(m/z):
   Found: 330.2064 $(M+H)^+$
   Calcd: 330.2064 (as $C_{20}H_{28}O_3N$)
(5) Infrared absorption spectrum:
   Peaks of infrared absorption measured by the KBr tablet method are as follows.
   $v_{max}(KBr)cm^{-1}$: 2927, 2855, 2713, 1736, 1642, 1589, 1227, 1181, 1078, 764, 724
(6) Proton nuclear magnetic resonance spectrum (600 MHz, Methanol-$d_4$):
   δ=0.88 (3H, t, J=6.8), 1.25-1.41 (8H, m), 1.50 (2H, m), 1.78 (2H, m), 2.54 (3H, s), 3.15 (2H, t, m), 4.92 (2H, s), 7.54 (1H, ddd, J=8.2, 7.2, 1.0), 7.92 (1H, ddd, J=8.5, 6.8, 1.0), 8.07 (1H, brd, J=8.5), 8.42 (1H, brd, J=8.2)
(7) $^{13}C$ nuclear magnetic resonance spectrum (150 MHz, Methanol-$d_4$):
   δ=12.23, 14.40, 23.67, 29.93, 30.27, 30.34, 30.74, 32.97, 35.07, 72.72, 122.81, 123.71, 123.85, 124.62, 129.16, 133.85, 142.14, 164.30, 167.46, 171.91

Physico-Chemical Properties of the Compound Expressed by Structural Formula (3)

Physico-chemical properties of the compound expressed by Structural Formula (3) as follows.

(1) Appearance: white powder
(2) Melting point: 178° C.-181° C.
(3) Molecular formula: $C_{19}H_{25}ON$
(4) High resolution mass spectrometry (HRESI-MS)(m/z):
   Found: 284.2011 $(M+H)^+$
   Calcd: 284.2009 (as $C_{19}H_{26}ON$)
(5) Infrared absorption spectrum:
   Peaks of infrared absorption measured by the KBr tablet method are as follows.
   $v_{max}(KBr)cm^{-1}$: 3064, 2957, 2933, 1670, 1638, 1614, 1555, 1500, 1371, 1358, 1152, 1028, 998, 967, 756, 691
(6) Proton nuclear magnetic resonance spectrum (600 MHz, $CDCl_3$):
   δ=0.95 (6H, d, J=6.5), 1.44 (2H, m), 1.69 (2H, m), 2.01 (2H, q, J=6.8), 2.15 (3H, s), 2.21 (1H, m), 2.70 (2H, m), 5.27-5.32 (1H, m), 5.36-5.39 (1H, m), 7.28 (1H, ddd, J=8.2, 5.8, 1.0), 7.32 (1H, brd, J=8.2), 7.52 (1H, ddd, J=8.2, 5.5, 1.4), 8.36 (1H, dd, J=8.2, 1.4), 8.65 (1H, br)
(7) $^{13}C$ nuclear magnetic resonance spectrum (150 MHz, $CDCl_3$):
   δ=10.65, 22.64, 27.77, 29.22, 30.98, 32.09, 32.96, 115.72, 116.69, 123.00, 123.66, 126.14, 126.30, 131.25, 138.49, 138.78, 148.54, 178.16

Physico-Chemical Properties of the Compound Expressed by Structural Formula (4)

Physico-chemical properties of the compound expressed by Structural Formula (4) as follows.

(1) Appearance: white powder
(2) Melting point: 240° C.-244° C.;
(3) Molecular formula: $C_{14}H_{17}ON$
(4) High resolution mass spectrometry (HRESI-MS)(m/z):
   Found: 216.1385 $(M+H)^+$
   Calcd: 216.1383 (as $C_{14}H_{18}ON$)
(5) Infrared absorption spectrum:
   Peaks of infrared absorption measured by the KBr tablet method are as follows.
   $v_{max}(KBr)cm^{-1}$: 3059, 2956, 1636, 1609, 1554, 1505, 1369, 1359, 1189, 998, 762, 695
(6) Proton nuclear magnetic resonance spectrum (400 MHz, DMSO-$d_6$):

δ=0.89 (6H, d, J=6.6), 1.94 (3H, s), 1.99 (1H, m), 2.53 (2H, d, J=7.5), 7.18 (1H, ddd, J=8.2, 6.6, 1.4), 7.46 (1H, d, J=8.2), 7.52 (1H, ddd, J=8.2, 6.6, 1.4), 8.01 (1H, dd, J=8.2, 1.1), 11.23 (1H, br s)

(7) $^{13}$C nuclear magnetic resonance spectrum (100 MHz, DMSO-$d_6$):

δ=11.03, 22.28, 28.30, 114.68, 117.74, 122.39, 123.00, 125.18, 131.08, 139.33, 148.76, 176.43

Physico-Chemical Properties of the Compound Expressed by Structural Formula (5)

Physico-chemical properties of the compound expressed by Structural Formula (5) as follows.

(1) Appearance: colorless oily substance
(2) Molecular formula: $C_{21}H_{29}O_3N$
(3) High resolution mass spectrometry (HRESI-MS)(m/z):
    Found: 344.2222 (M+H)$^+$
    Calcd: 344.2220 (as $C_{21}H_{30}O_3N$)
(4) Infrared absorption spectrum:
    Peaks of infrared absorption measured by the KBr tablet method are as follows.
    $v_{max}$(KBr)cm$^{-1}$: 2953, 2922, 1743, 1635, 1617, 1558, 1507, 1214, 994, 760, 688
(5) Proton nuclear magnetic resonance spectrum (400 MHz, CDCl$_3$):

δ=0.89 (3H, t, J=6.6), 1.21-1.51 (10H, m), 1.60 (2H, m), 2.22 (3H, s), 2.74 (2H, br), 3.80 (3H, s), 4.90 (2H, s), 7.20 (1H, d, J=8.7), 7.33 (1H, ddd, J=8.0, 6.8, 0.7), 7.58 (1H, ddd, J=8.7, 7.1, 1.6), 8.47 (1H, dd, J=8.0, 1.6)

(6) $^{13}$C nuclear magnetic resonance spectrum (100 MHz, CDCl$_3$):

δ=11.65, 14.06, 22.60, 28.06, 29.13, 29.17, 29.75, 30.93, 31.75, 48.47, 53.01, 114.19, 117.55, 123.11, 124.79, 127.30, 131.89, 140.66, 150.66, 168.69, 177.39

Physico-Chemical Properties of the Compound Expressed by Structural Formula (6)

Physico-chemical properties of the compound expressed by Structural Formula (6) as follows.

(1) Appearance: white powder
(2) Melting point: 161° C.-163° C.
(3) Molecular formula: $C_{20}H_{27}O_3N$
(4) High resolution mass spectrometry (HRESI-MS)(m/z):
    Found: 330.2063 (M+H)$^+$
    Calcd: 330.2064 (as $C_{20}H_{28}O_3N$)
(5) Infrared absorption spectrum:
    Peaks of infrared absorption measured by the KBr tablet method are as follows.
    $v_{max}$(KBr)cm$^{-1}$: 2955, 2925, 2853, 1725, 1635, 1593, 1506, 1191, 976, 760, 689
(6) Proton nuclear magnetic resonance spectrum (400 MHz, CDCl$_3$):

δ=0.87 (3H, t, J=6.4), 1.20-1.65 (12H, m), 2.19 (3H, s), 2.80 (2H, br), 4.98 (2H, br), 7.26 (1H, t, J=8.0), 7.42 (1H, d, J=8.7), 7.54 (1H, ddd, J=8.7, 6.8, 1.1), 8.39 (1H, dd, J=8.0, 1.1)

(7) $^{13}$C nuclear magnetic resonance spectrum (100 MHz, CDCl$_3$):

δ=11.91, 14.06, 22.68, 27.85, 29.12, 29.78, 31.26, 31.73, 49.71, 115.46, 117.21, 123.86, 123.94, 126.69, 132.47, 140.53, 154.22, 169.35, 176.57

Physico-Chemical Properties of the Compound Expressed by Structural Formula (7)

Physico-chemical properties of the compound expressed by Structural Formula (7) as follows.

(1) Appearance: colorless oily substance
(2) Molecular formula: $C_{19}H_{24}ON_2$
(3) High resolution mass spectrometry (HRESI-MS)(m/z):
    Found: 297.1961 (M+H)$^+$
    Calcd: 297.1961 (as $C_{19}H_{25}ON_2$)
(4) Infrared absorption spectrum:
    Peaks of infrared absorption measured by the KBr tablet method are as follows.
    $v_{max}$(KBr)cm$^{-1}$: 2961, 2926, 2853, 2237, 1628, 1576, 1470, 1292, 1191, 761, 693
(5) Proton nuclear magnetic resonance spectrum (400 MHz, CDCl$_3$):

δ=0.87 (3H, t, J=6.8), 1.20-1.50 (10H, m), 1.71 (2H, m), 2.15 (3H, s), 2.93 (2H, m), 7.47 (1H, m), 7.73 (2H, m), 8.33 (1H, ddd, J=8.0, 0.92, 1.1)

(6) $^{13}$C nuclear magnetic resonance spectrum (100 MHz, CDCl$_3$):

δ=11.20, 14.05, 22.59, 28.00, 29.07, 29.11, 29.42, 31.73, 31.80, 106.42, 116.28, 120.30, 123.35, 126.23, 127.08, 133.34, 137.25, 146.10, 177.31

Physico-Chemical Properties of the Compound Expressed by Structural Formula (8)

Physico-chemical properties of the compound expressed by Structural Formula (8) as follows.

(1) Appearance: yellow powder
(2) Melting point: >260° C.
(3) Molecular formula: $C_{18}H_{15}ON$
(4) High resolution mass spectrometry (HRESI-MS)(m/z):
    Found: 284.1046 (M+Na)$^+$
    Calcd: 284.1046 (as $C_{18}H_{15}ONNa$)
(5) Infrared absorption spectrum:
    Peaks of infrared absorption measured by the KBr tablet method are as follows.
    $v_{max}$(KBr)cm$^{-1}$: 3064, 2938, 1628, 1570, 1507, 1387, 1359, 1187, 965, 755, 690
(6) Proton nuclear magnetic resonance spectrum (400 MHz, DMSO-$d_6$):

δ=2.13 (3H, s), 7.21 (1H, ddd, J=8.5, 6.8, 1.1), 7.32-7.50 (5H, m), 7.55-7.59 (1H, m), 7.67-7.72 (3H, m), 8.03 (1H, dd, J=8.2, 1.4), 11.20 (1H, s)

(7) $^{13}$C nuclear magnetic resonance spectrum (100 MHz, DMSO-$d_6$):

δ=10.66, 115.68, 118.18, 121.14, 122.55, 123.13, 125.14, 127.57, 129.16, 129.30, 131.61, 135.11, 135.94, 139.75, 143.14, 176.76

Physico-Chemical Properties of the Compound Expressed by Structural Formula (9)

Physico-chemical properties of the compound expressed by Structural Formula (9) as follows.

(1) Appearance: colorless oily substance
(2) Molecular formula: $C_{21}H_{29}O_2NS$
(3) High resolution mass spectrometry (HRESI-MS)(m/z):
    Found: 360.1994 (M+H)$^+$
    Calcd: 360.1992 (as $C_{21}H_{30}O_2NS$)
(4) Infrared absorption spectrum:
    Peaks of infrared absorption measured by the KBr tablet method are as follows.
    $v_{max}$(KBr)cm$^{-1}$: 2924, 2852, 1687, 1614, 1594, 1542, 1193, 1028, 757, 558
(5) Proton nuclear magnetic resonance spectrum (400 MHz, CDCl$_3$):

δ=0.88 (3H, t, J=6.4), 1.20-1.50 (10H, m), 1.60 (2H, br), 2.23 (3H, s), 2.33 (3H, s), 2.51-2.99 (2H, br), 5.01 (2H, br), 7.21 (1H, d, J=8.7), 7.34 (1H, dd, J=8.0, 6.6), 7.58 (1H, ddd, J=8.7, 6.6, 1.4), 8.47 (1H, dd, J=8.0, 1.4)

(6) $^{13}$C nuclear magnetic resonance spectrum (100 MHz, CDCl$_3$):

δ=11.38, 11.68, 14.06, 22.60, 28.16, 29.13, 29.16, 29.75, 31.03, 31.74, 55.95, 114.61, 117.94, 123.32, 127.29, 131.97, 132.02, 140.73, 150.65, 177.49, 196.82

Physico-Chemical Properties of the Compound Expressed by Structural Formula (10)

Physico-chemical properties of the compound expressed by Structural Formula (10) as follows.
(1) Appearance: colorless oily substance
(2) Molecular formula: $C_{21}H_{30}O_2N_2S$
(3) High resolution mass spectrometry (HRESI-MS)(m/z):
Found: 397.1921 $(M+Na)^+$
Calcd: 397.1920 (as $C_{21}H_{30}O_2N_2NaS$)
(4) Infrared absorption spectrum:
Peaks of infrared absorption measured by the KBr tablet method are as follows.
$v_{max}(KBr)cm^{-1}$: 3169, 2955, 2927, 1671, 1615, 1595, 1556, 1492, 1195, 1084, 760, 651
(5) Proton nuclear magnetic resonance spectrum (600 MHz, $CDCl_3$):
δ=0.89 (3H, t, J=6.7), 1.22-1.45 (15H, m), 2.45 (2H, br), 2.46 (3H, s), 5.67 (2H, br), 7.24 (1H, ddd, J=7.9, 6.8, 1.0), 7.49 (1H, d, J=8.6), 7.59 (1H, ddd, J=8.6, 6.8, 1.4), 8.26 (1H, dd, J=7.9, 1.4), 8.78 (1H, br)
(6) $^{13}C$ nuclear magnetic resonance spectrum (150 MHz, $CDCl_3$):
δ=11.05, 12.22, 14.02, 22.59, 28.48, 29.11, 29.16, 29.73, 30.73, 31.77, 52.58, 115.46, 117.00, 123.24, 124.37, 126.89, 132.32, 139.56, 151.60, 168.61, 177.27

Physico-Chemical Properties of the Compound Expressed by Structural Formula (11)

Physico-chemical properties of the compound expressed by Structural Formula (11) as follows.
(1) Appearance: yellow oily substance
(2) Molecular formula: $C_{19}H_{24}ON_2S$
(3) High resolution mass spectrometry (HRESI-MS)(m/z):
Found: 329.1682 $(M+H)^+$
Calcd: 329.1682 (as $C_{19}H_{25}ON_2S$)
(4) Infrared absorption spectrum:
Peaks of infrared absorption measured by the KBr tablet method are as follows.
$v_{max}(KBr)cm^{-1}$: 2961, 2926, 2853, 2237, 1628, 1576, 1470, 1292, 1191, 987, 761, 693
(5) Proton nuclear magnetic resonance spectrum (400 MHz, $CDCl_3$):
δ=0.90 (3H, t, J=6.6), 1.23-1.71 (10H, m), 2.19 (3H, s), 2.84 (2H, m), 5.71 (2H, s), 7.38 (1H, ddd, J=8.0, 6.8, 0.9), 7.46 (1H, d, J=8.7), 7.68 (1H, ddd, J=8.7, 6.8, 1.6), 8.45 (1H, dd, J=8.0, 1.6)
(6) $^{13}C$ nuclear magnetic resonance spectrum (100 MHz, $CDCl_3$):
δ=11.60, 14.05, 22.56, 28.59, 28.88, 29.76, 30.55, 31.66, 56.26, 114.42, 118.19, 123.83, 124.60, 127.31, 132.41, 139.86, 141.68, 149.60, 177.64

Physico-Chemical Properties of the Compound Expressed by Structural Formula (12)

Physico-chemical properties of the compound expressed by Structural Formula (12) as follows.
(1) Appearance: yellow powder
(2) Melting point: 167° C.-170° C.
(3) Molecular formula: $C_{20}H_{28}ON_2S_2$
(4) High resolution mass spectrometry (HRESI-MS)(m/z):
Found: 399.1534 $(M+Na)^+$
Calcd: 399.1535 (as $C_{20}H_{28}ON_2NaS_2$)
(5) Infrared absorption spectrum:
Peaks of infrared absorption measured by the KBr tablet method are as follows.
$v_{max}(KBr)cm^{-1}$: 3119, 2958, 2918, 2850, 1619, 1598, 1538, 1282, 1199, 1105, 938, 764, 688
(6) Proton nuclear magnetic resonance spectrum (400 MHz, $CDCl_3$):
δ=0.86 (3H, t, J=6.6), 1.21-1.50 (13H, m), 2.22-2.58 (2H, br), 2.76 (3H, s), 5.68-6.41 (2H, br), 7.22 (1H, t, J=7.8), 7.44 (1H, d, J=8.7), 7.59 (1H, ddd, J=8.7, 7.8, 1.1), 8.15 (1H, d, J=7.8), 10.09 (1H, br)
(7) $^{13}C$ nuclear magnetic resonance spectrum (100 MHz, $CDCl_3$):
δ=10.74, 14.02, 18.01, 22.53, 28.29, 28.77, 29.64, 30.85, 31.59, 58.21, 115.93, 116.84, 123.54, 123.91, 126.35, 132.65, 139.39, 152.23, 177.13, 199.84

Physico-Chemical Properties of the Compound Expressed by Structural Formula (13)

Physico-chemical properties of the compound expressed by Structural Formula (13) as follows.
(1) Appearance: white powder
(2) Melting point: 92° C.-94° C.
(3) Molecular formula: $C_{21}H_{30}ON_2S_2$
(4) High resolution mass spectrometry (HRESI-MS)(m/z):
Found: 413.1689 $(M+Na)^+$
Calcd: 413.1692 (as $C_{21}H_{30}ON_2NaS_2$)
(5) Infrared absorption spectrum:
Peaks of infrared absorption measured by the KBr tablet method are as follows.
$v_{max}(KBr)cm^{-1}$: 2958, 2922, 2852, 1618, 1595, 1566, 1492, 1370, 1277, 1192, 1004, 769, 700
(6) Proton nuclear magnetic resonance spectrum (400 MHz, $CDCl_3$):
δ=0.89 (3H, t, J=6.8), 1.24-1.50 (8H, m), 1.64 (2H, m), 2.22 (3H, s), 2.28 (3H, s), 2.71 (3H, s), 2.77 (2H, m), 5.60 (2H, s), 7.31 (2H, m), 7.55 (1H, ddd, J=8.4, 7.1, 1.6), 8.46 (1H, dd, J=8.0, 1.6)
(7) $^{13}C$ nuclear magnetic resonance spectrum (100 MHz, $CDCl_3$):
δ=11.50, 14.06, 14.75, 15.03, 22.61, 28.28, 28.92, 29.83, 30.66, 31.76, 63.75, 115.84, 116.97, 122.77, 124.81, 126.75, 131.27, 141.06, 151.35, 161.39, 177.54

Whether the above compound has a structure expressed by any one of the above Structural Formulas (1) to (13) can be determined with appropriately selected various analysis methods. Examples thereof include spectroscopies such as the above mass spectrometry, the above infrared spectroscopy, the above proton nuclear magnetic resonance, the above $^{13}C$ nuclear magnetic resonance, and ultraviolet spectroscopy. Note that, the measurements obtained by each of the above analysis methods may have some errors, but those skilled in the art could easily identify which of the structures expressed by the above Structural Formulas (1) to (13) the compound has.

The above compound may be a salt of the compound expressed by any one of the above Structural Formulas (1) to (13).

The above salt is not particularly limited and may be appropriately selected depending on the intended purpose so long as it is a pharmacologically acceptable salt. Examples thereof include organic salts such as acetic acid salts and citric acid salts, hydrochloric acid salts, and carbonic acid salts.

The compound expressed by any one of the above Structural Formulas (1) to (13) may be a tautomer thereof.

A method for producing the compound expressed by any one of the above Structural Formulas (1) to (13) is not particularly limited and may be appropriately selected depending on the intended purpose. This compound is preferably obtained by a production method of the present invention described below.

Applications

The compound expressed by any one of the above Structural Formulas (1) to (13) has excellent anti-cancer effects or excellent anti-*Helicobacter pylori* activity, and is a highly safe compound. Therefore, the compound expressed by any one of the above Structural Formulas (1) to (13) can be suitably used as an active ingredient of, for example, a compound-containing composition of the present invention, an anti-cancer agent of the present invention, and an anti-*Helicobacter pylori* agent of the present invention, which will be described below.

(Method for Producing Compound)

Method for producing the compound expressed by any one of the above Structural Formulas (3), (4), and (8)

A method for producing the compound expressed by any one of the above Structural Formulas (3), (4), and (8) is not particularly limited and may be appropriately selected depending on the intended purpose so long as it is a method including reacting a compound expressed by any one of Structural Formula (17), (18), and (19) below with a hydroxide of an alkali metal or a hydroxide of an alkaline earth metal, or both thereof.

Structural Formula (17)

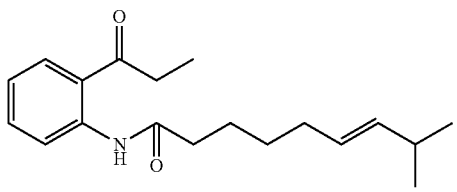

Structural Formula (18)

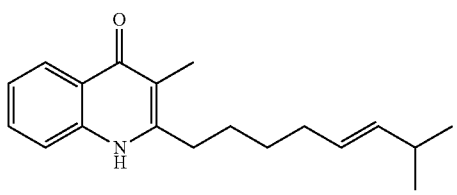

Structural Formula (19)

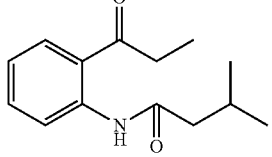

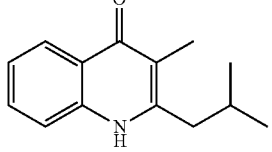

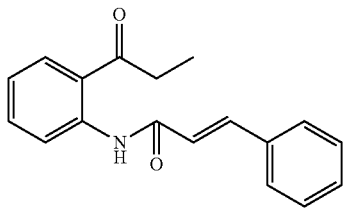

Structural Formula (8)

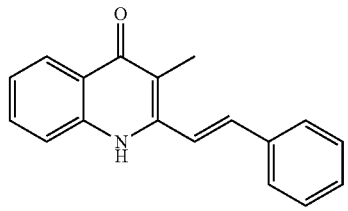

The above alkali metal refers to lithium, sodium, potassium, rubidium, cesium, and francium. The alkaline earth metal refers to calcium, strontium, barium, and radium.

The above hydroxide of the alkali metal is not particularly limited and may be appropriately selected depending on the intended purpose. Examples thereof include lithium hydroxide, sodium hydroxide, and potassium hydroxide.

The above hydroxide of the alkaline earth metal is not particularly limited and may be appropriately selected depending on the intended purpose. Examples thereof include barium hydroxide.

Either the above hydroxide of the alkali metal or the above hydroxide of the alkaline earth metal may be used, or both thereof may be used in combination.

One kind of the above hydroxide of the alkali metal may be used alone, or two or more kinds thereof may be used in combination. Also, one kind of the above hydroxide of the alkaline earth metal may be used alone, or two or more kinds thereof may be used in combination.

Among the above hydroxide of the alkali metal and the hydroxide of the alkaline earth metal, sodium hydroxide is preferable.

As preferable aspects of the method for producing the compound expressed by any one of the above Structural Formulas (3), (4), and (8), aspects where aminobenzonitrile is used as a starting material will be described below.

—Production of the Compound Expressed by Structural Formula (14)—

The compound expressed by the above Structural Formula (14) can be produced in the following manner, for example.

In an argon atmosphere, aminobenzonitrile is dissolved in anhydrous tetrahydrofuran (hereinafter may be referred to as "THF"), and ethylmagnesium bromide is added dropwise thereto in an ice bath. The mixture is stirred at room temperature for 12 hours, and then hydrochloric acid aqueous solution (10%) is added dropwise thereto in an ice bath. After completion of the dropwise addition, sodium hydroxide is added thereto in an ice bath, and the pH of the mixture is adjusted to 7. The organic layer is separated, and the aqueous layer is extracted with diethyl ether. The organic layers are combined and dried with Glauber's salt, and the solvent is evaporated. The residue is purified through silica gel chromatography (hexane:ethyl acetate=6:1), and as a result the compound expressed by Structural Formula (14) can be obtained.

Structural Formula (14)

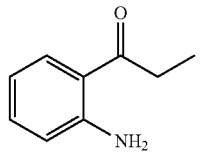

—Production of the Compound Expressed by Structural Formula (17)—

The compound expressed by the above Structural Formula (17) can be produced in the following manner, for example.

In an argon atmosphere, the compound expressed by the above Structural Formula (14) is dissolved in methylene chloride, and triethylamine is added thereto. Furthermore, trans-8-methyl-6-nonenoyl chloride, which is an acid chloride, is added dropwise to the mixture in an ice bath, followed by stirring at room temperature. The reaction is terminated with 0.1N hydrochloric acid, and the mixture is extracted with methylene chloride, followed by washing with saturated sodium hydrogencarbonate aqueous solution and brine. The combined organic layer is dried with Glauber's salt, and then the solvent is evaporated. The residue is purified through silica gel chromatography (hexane:ethyl acetate), and as a result the compound expressed by Structural Formula (17) can be obtained.

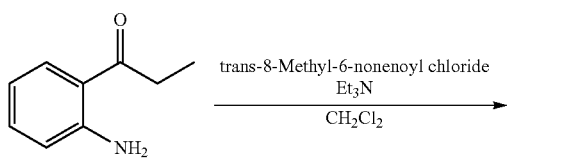

Structural Formula (14)

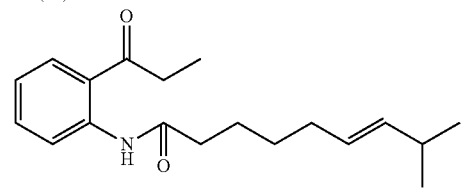

Structural Formula (17)

—Production of the Compound Expressed by Structural Formula (3)—

The compound expressed by the above Structural Formula (3) can be produced in the following manner, for example.

Sodium hydroxide is added to a dioxane solution of the compound expressed by the above Structural Formula (17) (0.1 M), and the mixture is stirred at 110° C. for 1 hour to 2 hours. The reaction solution is returned to room temperature, followed by addition of water, and also, 1N hydrochloric acid is added thereto until the pH thereof reaches 7. Furthermore, when hexane is added and then ultrasonic waves are applied thereto, solids precipitate. The solids are filtrated through aspiration, followed by washing with water, and hexane or a solvent mixture of hexane/ethyl acetate=1:1. The washing is followed by drying, and as a result the compound expressed by Structural Formula (3) can be obtained.

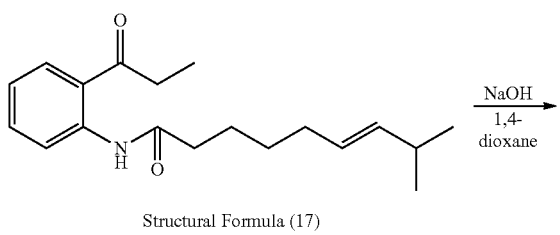

Structural Formula (17)

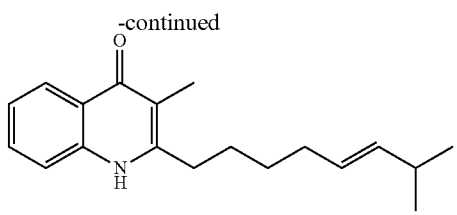

Structural Formula (3)

—Production of the Compound Expressed by Structural Formula (18)—

The compound expressed by the above Structural Formula (18) can be produced in the following manner, for example.

In an argon atmosphere, the compound expressed by the above Structural Formula (14) is dissolved in methylene chloride, followed by addition of triethylamine. Furthermore, isovaleryl chloride, which is an acid chloride, is added dropwise to the mixture in an ice bath, followed by stirring at room temperature. The reaction is terminated with 0.1N hydrochloric acid, and the mixture is extracted with methylene chloride, followed by washing with saturated sodium hydrogencarbonate aqueous solution and brine. The combined organic layer is dried with Glauber's salt, and then the solvent is evaporated. The residue is purified through silica gel chromatography (hexane:ethyl acetate), and as a result the compound expressed by Structural Formula (18) can be obtained.

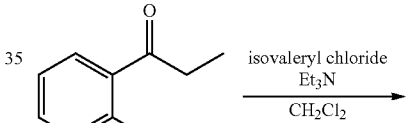

Structural Formula (14)

Structural Formula (18)

—Production of the Compound Expressed by Structural Formula (4)—

The compound expressed by the above Structural Formula (4) can be produced in the following manner, for example.

Sodium hydroxide is added to a 1,4-dioxane solution of the compound expressed by the above Structural Formula (18) (0.1 M), and the mixture is stirred at 110° C. for 1 hour to 2 hours. The reaction solution is returned to room temperature, followed by addition of water, and also, 1N hydrochloric acid is added thereto until the pH thereof reaches 7. Furthermore, when hexane is added and ultrasonic waves are applied thereto, solids precipitate. The solids are filtrated through aspiration, followed by washing with water, and hexane or a solvent mixture of hexane/ethyl acetate=1:1. The washing is followed by drying, and as a result the compound expressed by Structural Formula (4) can be obtained.

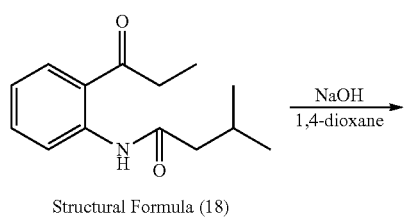

Structural Formula (18)

Structural Formula (4)

—Production of the Compound Expressed by Structural Formula (19)—

The compound expressed by the above Structural Formula (19) can be produced in the following manner, for example.

In an argon atmosphere, the compound expressed by the above Structural Formula (14) is dissolved in methylene chloride, followed by addition of triethylamine. Furthermore, cinnamoyl chloride, which is an acid chloride, is added dropwise to the mixture in an ice bath, followed by stirring at room temperature. The reaction is terminated with 0.1N hydrochloric acid, and the mixture is extracted with methylene chloride, followed by washing with saturated sodium hydrogencarbonate aqueous solution and brine. The combined organic layer is dried with Glauber's salt, and then the solvent is evaporated. The residue is purified through silica gel chromatography (hexane:ethyl acetate), and as a result the compound expressed by Structural Formula (19) can be obtained.

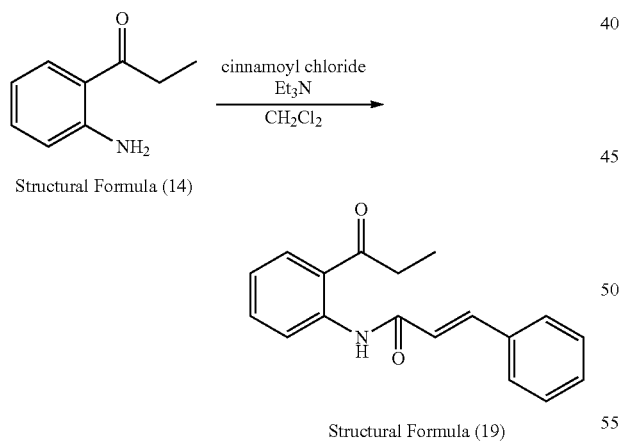

Structural Formula (14)

Structural Formula (19)

—Production of the Compound Expressed by Structural Formula (8)—

The compound expressed by the above Structural Formula (8) can be produced in the following manner, for example.

Sodium hydroxide is added to a 1,4-dioxane solution of the compound expressed by the above Structural Formula (19) (0.1 M), and the mixture is stirred at 110° C. for 1 hour to 2 hours. The reaction solution is returned to room temperature, followed by addition of water, and also, 1N hydrochloric acid is added thereto until the pH thereof reaches 7. Furthermore, when hexane is added and ultrasonic waves are applied thereto, solids precipitate. The solids are filtrated through aspiration, followed by washing with water, and hexane or a solvent mixture of hexane/ethyl acetate=1:1. The washing is followed by drying, and as a result the compound expressed by Structural Formula (8) can be obtained.

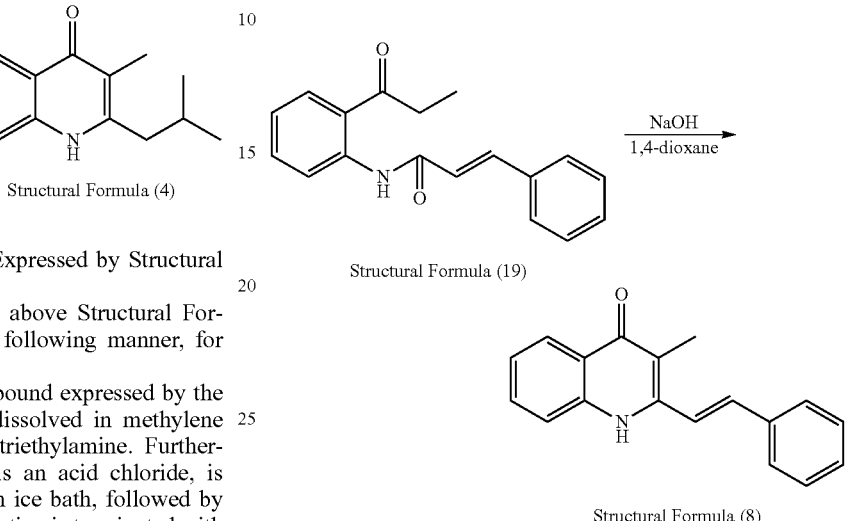

Structural Formula (19)

Structural Formula (8)

Method for Producing the Compound Expressed by the Above Structural Formula (5)

A method for producing the compound expressed by the above Structural Formula (5) is not particularly limited and may be appropriately selected depending on the intended purpose so long as it is a method including reacting a compound expressed by Structural Formula (21) below with an alkoxide of an alkali metal, a carbonic acid salt of an alkali metal or a hydride of an alkali metal, or any combination thereof, to thereby obtain a reaction product, and reacting the reaction product and methyl bromoacetate.

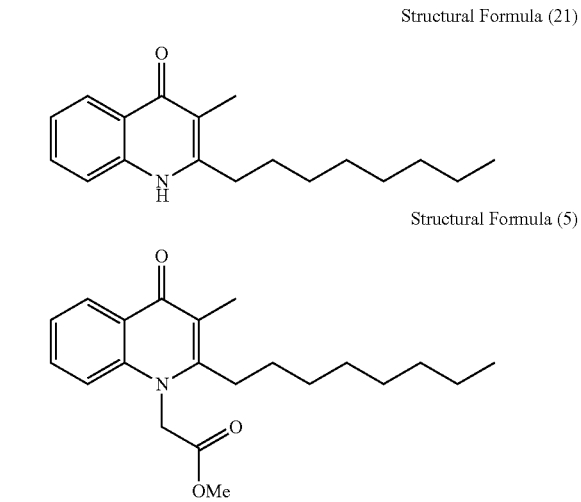

Structural Formula (21)

Structural Formula (5)

In the Structural Formula (5), Me denotes a methyl group.

The above alkali metal refers to lithium, sodium, potassium, rubidium, cesium, and francium.

The above alkoxide of the alkali metal is not particularly limited and may be appropriately selected depending on the intended purpose. Examples thereof include lithium t-butoxide.

The above carbonic acid salt of the alkali metal is not particularly limited and may be appropriately selected depending on the intended purpose. Examples thereof include sodium carbonate, potassium carbonate, sodium hydrogencarbonate, and potassium hydrogencarbonate.

The above hydride of the alkali metal is not particularly limited and may be appropriately selected depending on the intended purpose. Examples thereof include sodium hydride.

One kind of the above alkoxide of the alkali metal, the above carbonic acid salt of the alkali metal, and the above hydride of the alkali metal may be used alone, or two or more kinds thereof may be used in combination.

One kind of the above alkoxide of the alkali metal may be used alone, or two or more kinds thereof may be used in combination. One kind of the above carbonic acid salt of the alkali metal may be used alone, or two or more kinds thereof may be used in combination. Also, one kind of the above hydride of the alkali metal may be used alone, or two or more kinds thereof may be used in combination.

Among the above alkoxide of the alkali metal, the above carbonic acid salt of the alkali metal, and the above hydride of the alkali metal, lithium t-butoxide, potassium carbonate, and sodium hydride are preferable, with lithium t-butoxide being more preferable.

As a preferable aspect of the method for producing the compound expressed by the above Structural Formula (5), an aspect where the compound expressed by the above Structural Formula (14) is used as a starting material will be described below.

Note that, the compound expressed by the above Structural Formula (14) can be suitably produced by the above-described method.

—Production of the Compound Expressed by Structural Formula (16)—

The compound expressed by the above Structural Formula (16) can be produced in the following manner, for example.

In an argon atmosphere, the compound expressed by the above Structural Formula (14) is dissolved in methylene chloride, and triethylamine is added thereto. Furthermore, nonanoyl chloride, which is an acid chloride, is added dropwise to the mixture in an ice bath, followed by stirring at room temperature. The reaction is terminated with 0.1N hydrochloric acid, and the mixture is extracted with methylene chloride, followed by washing with saturated sodium hydrogencarbonate aqueous solution and brine. The combined organic layer is dried with Glauber's salt, and then the solvent is evaporated. The residue is purified through silica gel chromatography (hexane:ethyl acetate), and as a result the compound expressed by Structural Formula (16) can be obtained.

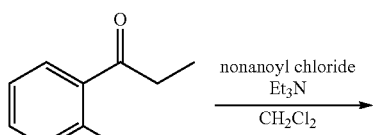

Structural Formula (14)

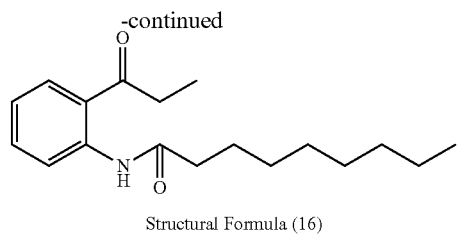

Structural Formula (16)

—Production of the Compound Expressed by Structural Formula (21)—

The compound expressed by the above Structural Formula (21) can be produced in the following manner, for example.

Sodium hydroxide is added to a 1,4-dioxane solution of the compound expressed by the above Structural Formula (16) (0.1 M), and the mixture is stirred at 110° C. for 1 hour to 2 hours. The reaction solution is returned to room temperature, followed by addition of water, and also, 1N hydrochloric acid is added thereto until the pH thereof reaches 7. Furthermore, when hexane is added and then ultrasonic waves are applied thereto, solids precipitate. The solids are filtrated through aspiration, followed by washing with water, and hexane or a solvent mixture of hexane/ethyl acetate=1:1. The washing is followed by drying, and as a result the compound expressed by Structural Formula (21) can be obtained.

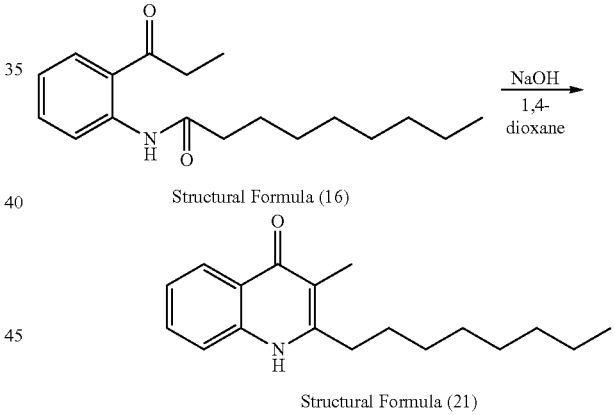

—Production of the Compound Expressed by Structural Formula (5)—

The compound expressed by the above Structural Formula (5) can be produced in the following manner, for example.

In an argon atmosphere, the compound expressed by the above Structural Formula (21) is dissolved in THF, and a THF solution of lithium t-butoxide is added thereto, followed by stirring at room temperature for 20 minutes. Next, methyl bromoacetate is added thereto, and the mixture is further stirred under reflux for 12 hours. The reaction is terminated by the addition of water, and the mixture is extracted with ethyl acetate. The organic layer is dried with Glauber's salt, and then the solvent is evaporated. The residue is purified through silica gel chromatography (hexane:ethyl acetate=2:1), and as a result the compound expressed by Structural Formula (5) can be obtained.

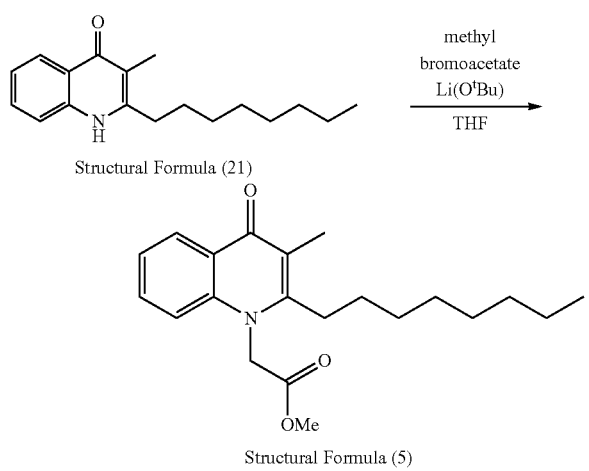

Method for Producing the Compound Expressed by the Above Structural Formula (6)

A method for producing the compound expressed by the above Structural Formula (6) is not particularly limited and may be appropriately selected depending on the intended purpose so long as it is a method including reacting a compound expressed by Structural Formula (5) below with a hydroxide of an alkali metal or a hydroxide of an alkaline earth metal, or both thereof, to thereby obtain a reaction product, and acidifying a pH of the reaction product.

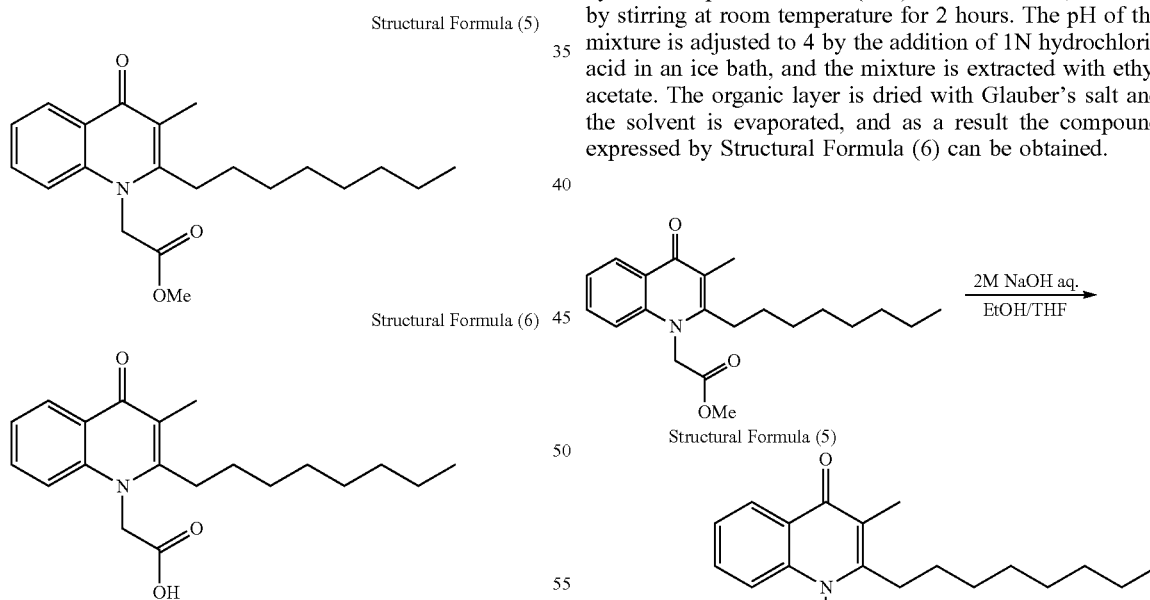

In the above Structural Formula (5), Me denotes a methyl group.

The above alkali metal refers to lithium, sodium, potassium, rubidium, cesium, and francium. The alkaline earth metal refers to calcium, strontium, barium, and radium.

The above hydroxide of the alkali metal is not particularly limited and may be appropriately selected depending on the intended purpose. Examples thereof include lithium hydroxide, sodium hydroxide, and potassium hydroxide.

The above hydroxide of the alkaline earth metal is not particularly limited and may be appropriately selected depending on the intended purpose. Examples thereof include barium hydroxide.

Either the above hydroxide of the alkali metal or the above hydroxide of the alkaline earth metal may be used, or both thereof may be used in combination.

One kind of the above hydroxide of the alkali metal may be used alone, or two or more kinds thereof may be used in combination. Also, one kind of the above hydroxide of the alkaline earth metal may be used alone, or two or more kinds thereof may be used in combination.

Among the above hydroxide of the alkali metal and the hydroxide of the alkaline earth metal, sodium hydroxide is preferable.

As a preferable aspect of the method for producing the compound expressed by the above Structural Formula (6), an aspect where the compound expressed by the above Structural Formula (5) is used as a starting material will be described below.

Note that, the compound expressed by the above Structural Formula (5) can be suitably produced by the above-described method.

—Production of the Compound Expressed by Structural Formula (6)—

The compound expressed by the above Structural Formula (6) can be produced in the following manner, for example.

The compound expressed by the above Structural Formula (5) is dissolved in a solvent mixture of ethanol (hereinafter may be referred to as "EtOH") and THF, and sodium hydroxide aqueous solution (2 M) is added thereto, followed by stirring at room temperature for 2 hours. The pH of the mixture is adjusted to 4 by the addition of 1N hydrochloric acid in an ice bath, and the mixture is extracted with ethyl acetate. The organic layer is dried with Glauber's salt and the solvent is evaporated, and as a result the compound expressed by Structural Formula (6) can be obtained.

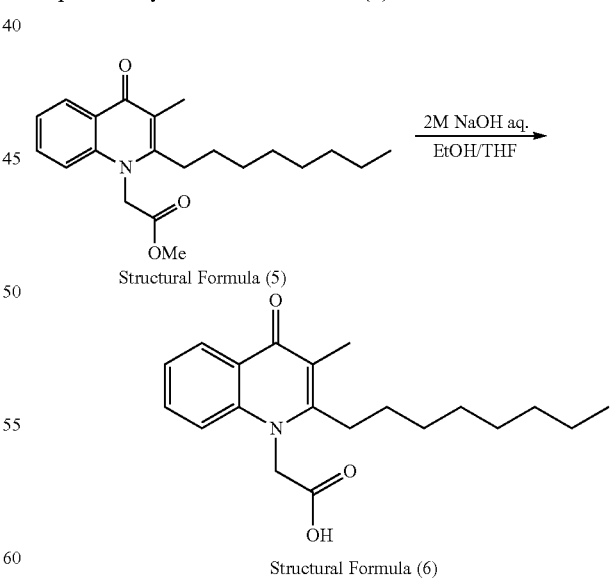

Method for Producing the Compound Expressed by the Above Structural Formula (1)

A method for producing the compound expressed by the above Structural Formula (1) is not particularly limited and may be appropriately selected depending on the intended purpose so long as it is a method including reacting a compound expressed by Structural Formula (21) below with a carbonic acid salt of an alkali metal or a hydride of an alkali metal, or both thereof, and methyl bromoacetate.

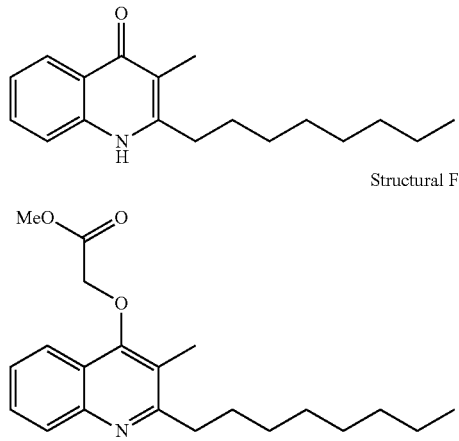

Structural Formula (21)

Structural Formula (1)

In the above Structural Formula (1), Me denotes a methyl group.

The above alkali metal refers to lithium, sodium, potassium, rubidium, cesium, and francium.

The above carbonic acid salt of the alkali metal is not particularly limited and may be appropriately selected depending on the intended purpose. Examples thereof include sodium carbonate, potassium carbonate, sodium hydrogencarbonate, and potassium hydrogencarbonate.

The above hydride of the alkali metal is not particularly limited and may be appropriately selected depending on the intended purpose. Examples thereof include sodium hydride.

Either the above carbonic acid salt of the alkali metal or the above hydride of the alkali metal may be used, or both thereof may be used in combination.

One kind of the above carbonic acid salt of the alkali metal may be used alone, or two or more kinds thereof may be used in combination. Also, one kind of the above hydride of the alkali metal may be used alone, or two or more kinds thereof may be used in combination.

Among the above carbonic acid salt of the alkali metal and the above hydride of the alkali metal, potassium carbonate and sodium hydride are preferable, with potassium carbonate being more preferable.

As a preferable aspect of the method for producing the compound expressed by the above Structural Formula (1), an aspect where the compound expressed by the above Structural Formula (21) is used as a starting material will be described below.

Note that, the compound expressed by the above Structural Formula (21) can be suitably produced by the above-described method.

—Production of the Compound Expressed by Structural Formula (1)—

The compound expressed by the above Structural Formula (1) can be produced in the following manner, for example.

The compound expressed by the above Structural Formula (21) is dissolved in N,N-dimethylformamide (hereinafter may be referred to as "DMF"), and potassium carbonate and methyl bromoacetate are added thereto, followed by stirring at 80° C. for 12 hours. The reaction is terminated by the addition of water, and the mixture is extracted with ethyl acetate. The organic layer is dried with Glauber's salt, and then the solvent is evaporated. The residue is purified through silica gel chromatography (hexane:ethyl acetate=2:1), and as a result the compound expressed by Structural Formula (1) can be obtained.

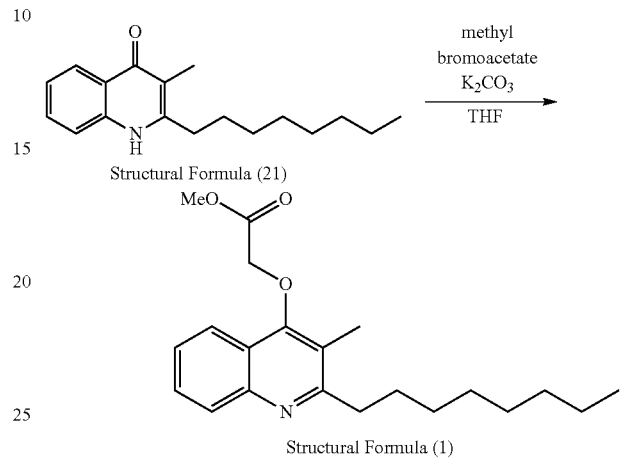

Method for Producing the Compound Expressed by the Above Structural Formula (2)

A method for producing the compound expressed by the above Structural Formula (2) is not particularly limited and may be appropriately selected depending on the intended purpose so long as it is a method including reacting a compound expressed by Structural Formula (1) below with a hydroxide of an alkali metal or a hydroxide of an alkaline earth metal, or both thereof, to thereby obtain a reaction product, and acidifying a pH of the reaction product.

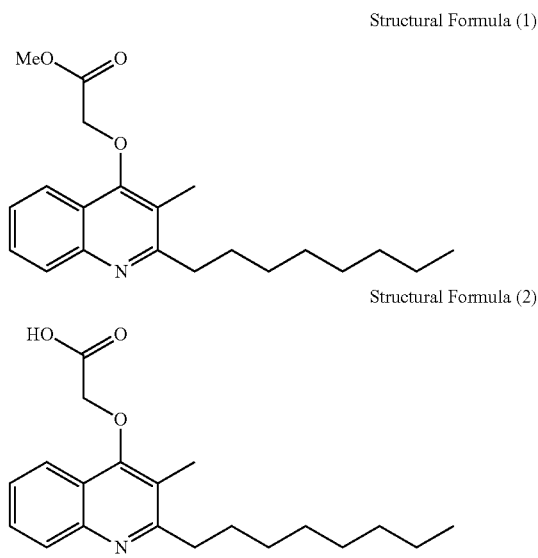

Structural Formula (1)

Structural Formula (2)

In the above Structural Formula (1), Me denotes a methyl group.

The above alkali metal refers to lithium, sodium, potassium, rubidium, cesium, and francium. The alkaline earth metal refers to calcium, strontium, barium, and radium.

The above hydroxide of the alkali metal is not particularly limited and may be appropriately selected depending on the intended purpose. Examples thereof include lithium hydroxide, sodium hydroxide, and potassium hydroxide.

The above hydroxide of the alkaline earth metal is not particularly limited and may be appropriately selected depending on the intended purpose. Examples thereof include barium hydroxide.

Either the above hydroxide of the alkali metal or the above hydroxide of the alkaline earth metal may be used, or both thereof may be used in combination.

One kind of the above hydroxide of the alkali metal may be used alone, or two or more kinds thereof may be used in combination. Also, one kind of the above hydroxide of the alkaline earth metal may be used alone, or two or more kinds thereof may be used in combination.

Among the above hydroxide of the alkali metal and the hydroxide of the alkaline earth metal, sodium hydroxide is preferable.

A method for acidifying the pH of the reaction product is not particularly limited and may be appropriately selected depending on the intended purpose. Examples thereof include 1N hydrochloric acid.

As a preferable aspect of the method for producing the compound expressed by the above Structural Formula (2), an aspect where the compound expressed by the above Structural Formula (1) is used as a starting material will be described below.

Note that, the compound expressed by the above Structural Formula (1) can be suitably produced by the above-described method.

—Production of the Compound Expressed by Structural Formula (2)—

The compound expressed by the above Structural Formula (2) can be produced in the following manner, for example.

The compound expressed by the above Structural Formula (1) is dissolved in a solvent mixture of EtOH and THF, and sodium hydroxide aqueous solution (2 M) is added thereto, followed by stirring at room temperature for 2 hours. The pH of the mixture is adjusted to 4 by the addition of 1N hydrochloric acid in an ice bath, and the mixture is extracted with ethyl acetate. The organic layer is dried with Glauber's salt and the solvent is evaporated, and as a result the compound expressed by Structural Formula (2) can be obtained.

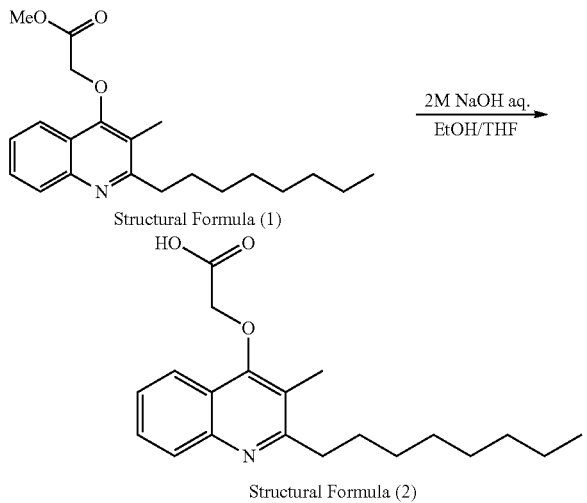

Method for Producing the Compound Expressed by the Above Structural Formula (7)

A method for producing the compound expressed by the above Structural Formula (7) is not particularly limited and may be appropriately selected depending on the intended purpose so long as it is a method including reacting a compound expressed by Structural Formula (21) below with an alkoxide of an alkali metal or a hydride of an alkali metal, or both thereof, to thereby obtain a reaction product, and reacting the reaction product and cyanogen bromide.

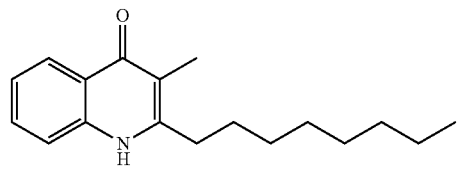

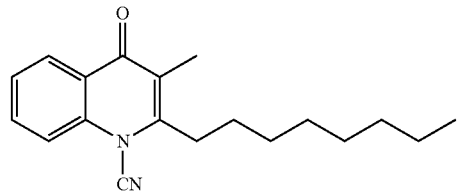

The above alkali metal refers to lithium, sodium, potassium, rubidium, cesium, and francium.

The above alkoxide of the alkali metal is not particularly limited and may be appropriately selected depending on the intended purpose. Examples thereof include lithium t-butoxide.

The above hydride of the alkali metal is not particularly limited and may be appropriately selected depending on the intended purpose. Examples thereof include sodium hydride.

Either the above alkoxide of the alkali metal or the above hydride of the alkali metal may be used, or both thereof may be used in combination.

One kind of the above alkoxide of the alkali metal may be used alone, or two or more kinds thereof may be used in combination. Also, one kind of the above hydride of the alkali metal may be used alone, or two or more kinds thereof may be used in combination.

Among the above alkoxide of the alkali metal and the above hydride of the alkali metal, lithium t-butoxide and sodium hydride are preferable, with lithium t-butoxide being more preferable.

As a preferable aspect of the method for producing the compound expressed by the above Structural Formula (7), an aspect where the compound expressed by the above Structural Formula (21) is used as a starting material will be described below.

Note that, the compound expressed by the above Structural Formula (21) can be suitably produced by the above-described method.

—Production of the Compound Expressed by Structural Formula (7)—

The compound expressed by the above Structural Formula (7) can be produced in the following manner, for example.

The compound expressed by the above Structural Formula (21) is dissolved in THF, and lithium t-butoxide is added thereto, followed by stirring at room temperature for 20 minutes. Next, cyanogen bromide is added thereto, and the mixture is stirred at room temperature for 2 hours. The reaction is terminated by the addition of water, and the mixture is extracted with ethyl acetate. The organic layer is dried with Glauber's salt, and then the solvent is evaporated. The residue is purified through silica gel chromatography (hexane:ethyl acetate=2:1), and as a result the compound expressed by Structural Formula (7) (34.0 mg, 62%) can be obtained.

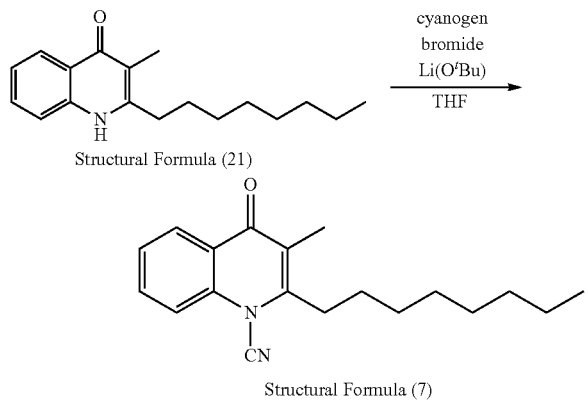

Method for Producing the Compound Expressed by the Above Structural Formula (9)

A method for producing the compound expressed by the above Structural Formula (9) is not particularly limited and may be appropriately selected depending on the intended purpose so long as it is a method including reacting a compound expressed by Structural Formula (6) below with a tertiary amine or a pyridine, or both thereof, diphenylphosphoryl azide, and sodium thiomethoxide.

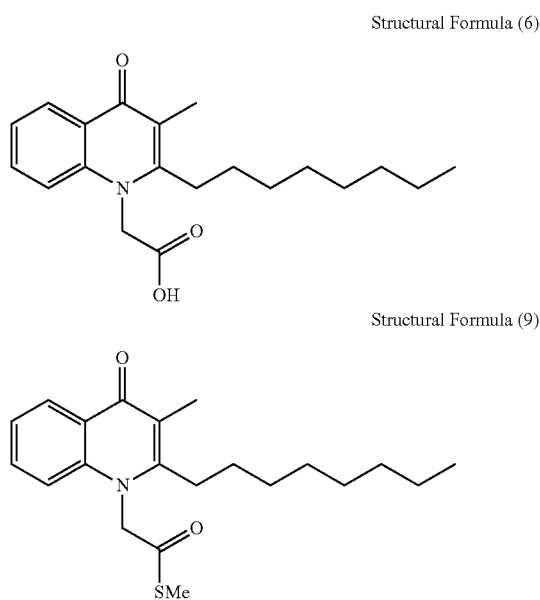

In the above Structural Formula (9), Me denotes a methyl group.

The tertiary amine is not particularly limited and may be appropriately selected depending on the intended purpose. Examples thereof include triethylamine and N,N-diisopropylethylamine.

The pyridine is not particularly limited and may be appropriately selected depending on the intended purpose. Examples thereof include pyridine and dimethylaminopyridine.

Either the tertiary amine or the pyridine may be used, or both thereof may be used in combination.

One kind of the tertiary amine may be used alone, or two or more kinds thereof may be used in combination. Also, one kind of the pyridine may be used alone, or two or more kinds thereof may be used in combination.

Among the tertiary amine and the pyridine, triethylamine is preferable.

As a preferable aspect of the method for producing the compound expressed by the above Structural Formula (9), an aspect where the compound expressed by the above Structural Formula (6) is used as a starting material will be described below.

Note that, the compound expressed by the above Structural Formula (6) can be suitably produced by the above-described method.

—Production of the Compound Expressed by Structural Formula (9)—

The compound expressed by the above Structural Formula (9) can be produced in the following manner, for example.

The compound expressed by the above Structural Formula (6) is suspended in THF, and triethylamine, diphenylphosphoryl azide (hereinafter may be referred to as "DPPA"), and sodium thiomethoxide are added thereto, and the mixture is stirred under reflux for 2 hours. Ammonium chloride aqueous solution is added thereto, and the mixture is extracted with ethyl acetate. The organic layer is dried with Glauber's salt, and the solvent is evaporated. The residue is purified through silica gel chromatography (hexane:ethyl acetate=3:1), and as a result the compound expressed by Structural Formula (9) can be obtained.

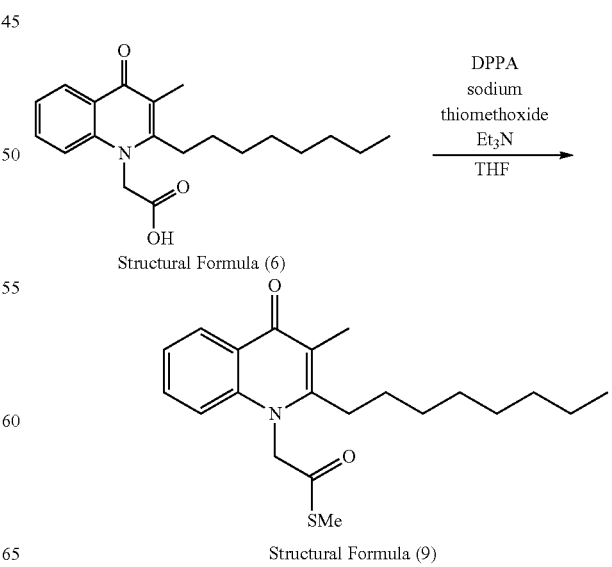

Method for Producing the Compound Expressed by the Above Structural Formula (10)

A method for producing the compound expressed by the above Structural Formula (10) is not particularly limited and may be appropriately selected depending on the intended purpose so long as it is a method including reacting a compound expressed by Structural Formula (6) below with a tertiary amine or a pyridine, or both thereof, and diphenylphosphoryl azide, to thereby obtain a reaction product, and reacting the reaction product and sodium thiomethoxide.

The compound expressed by the above Structural Formula (6) is suspended in THF, and triethylamine and DPPA are added thereto under cooling with ice, and the mixture is further stirred under reflux for 1 hour. Sodium thiomethoxide is added thereto, followed by stirring for another 1 hour. Ammonium chloride aqueous solution is added thereto, and the mixture is extracted with ethyl acetate. The organic layer is dried with Glauber's salt, and the solvent is evaporated. The residue is purified through silica gel chromatography (hexane:ethyl acetate=5:1), and as a result the compound expressed by Structural Formula (10) can be obtained.

Structural Formula (6)

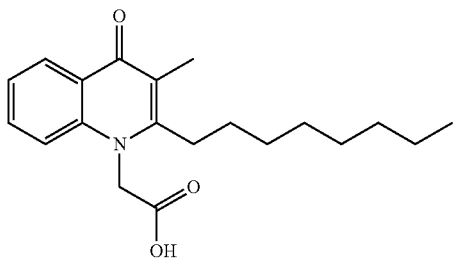

Structural Formula (10)

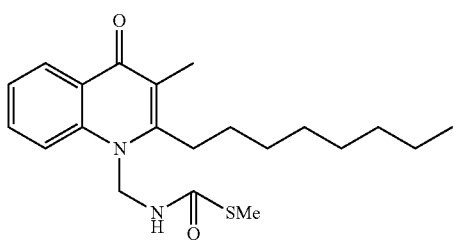

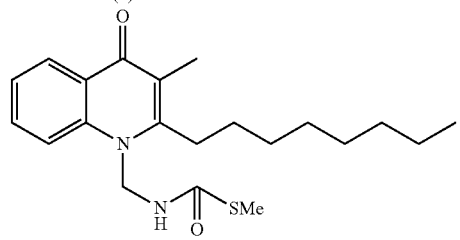

In the above Structural Formula (10), Me denotes a methyl group.

The tertiary amine is not particularly limited and may be appropriately selected depending on the intended purpose. Examples thereof include triethylamine and N,N-diisopropylethylamine.

The pyridine is not particularly limited and may be appropriately selected depending on the intended purpose. Examples thereof include pyridine and dimethylaminopyridine.

Either the tertiary amine or the pyridine may be used, or both thereof may be used in combination.

One kind of the tertiary amine may be used alone, or two or more kinds thereof may be used in combination. Also, one kind of the pyridine may be used alone, or two or more kinds thereof may be used in combination.

Among the tertiary amine and the pyridine, triethylamine is preferable.

As a preferable aspect of the method for producing the compound expressed by the above Structural Formula (10), an aspect where the compound expressed by the above Structural Formula (6) is used as a starting material will be described below.

Note that, the compound expressed by the above Structural Formula (6) can be suitably produced by the above-described method.

—Production of the Compound Expressed by Structural Formula (10)—

The compound expressed by the above Structural Formula (10) can be produced in the following manner, for example.

Method for Producing the Compound Expressed by the Above Structural Formula (11)

A method for producing the compound expressed by the above Structural Formula (11) is not particularly limited and may be appropriately selected depending on the intended purpose so long as it is a method including reacting a compound expressed by Structural Formula (20) below with an alkoxide of an alkali metal or a hydride of an alkali metal, or both thereof, to thereby obtain a reaction product, and reacting the reaction product and chloromethyl thiocyanate.

Structural Formula (20)

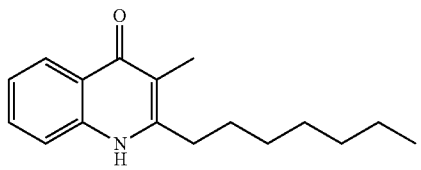

Structural Formula (11)

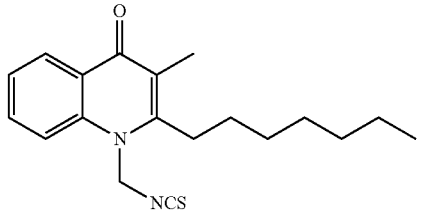

The above alkali metal refers to lithium, sodium, potassium, rubidium, cesium, and francium.

The above alkoxide of the alkali metal is not particularly limited and may be appropriately selected depending on the intended purpose. Examples thereof include lithium t-butoxide.

The above hydride of the alkali metal is not particularly limited and may be appropriately selected depending on the intended purpose. Examples thereof include sodium hydride.

Either the above alkoxide of the alkali metal or the above hydride of the alkali metal may be used, or both thereof may be used in combination.

One kind of the above alkoxide of the alkali metal may be used alone, or two or more kinds thereof may be used in combination. Also, one kind of the above hydride of the alkali metal may be used alone, or two or more kinds thereof may be used in combination.

Among the above alkoxide of the alkali metal and the above hydride of the alkali metal, lithium t-butoxide and sodium hydride are preferable, with lithium t-butoxide being more preferable.

As a preferable aspect of the method for producing the compound expressed by the above Structural Formula (11), an aspect where the compound expressed by the above Structural Formula (14) is used as a starting material will be described below.

Note that, the compound expressed by the above Structural Formula (14) can be suitably produced by the above-described method.

—Production of the Compound Expressed by Structural Formula (15)—

The compound expressed by the above Structural Formula (15) can be produced in the following manner, for example.

In an argon atmosphere, the compound expressed by the above Structural Formula (14) is dissolved in methylene chloride, and triethylamine is added thereto. Furthermore, octanoyl chloride, which is an acid chloride, is added dropwise to the mixture in an ice bath, followed by stirring at room temperature. The reaction is terminated with 0.1N hydrochloric acid, and the mixture is extracted with methylene chloride, followed by washing with saturated sodium hydrogencarbonate aqueous solution and brine. The combined organic layer is dried with Glauber's salt, and then the solvent is evaporated. The residue is purified through silica gel chromatography (hexane:ethyl acetate), and as a result the compound expressed by Structural Formula (15) can be obtained.

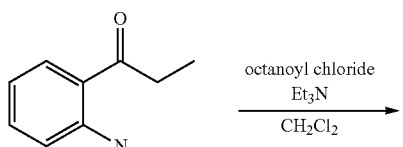

Structural Formula (14)

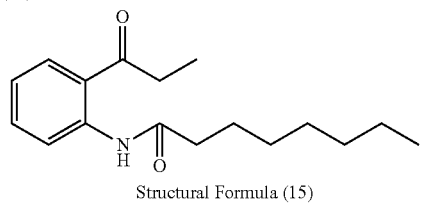

Structural Formula (15)

—Production of the Compound Expressed by Structural Formula (20)—

The compound expressed by the above Structural Formula (20) can be produced in the following manner, for example.

Sodium hydroxide is added to a dioxane solution of the compound expressed by the above Structural Formula (15) (0.1 M), and the mixture is stirred at 110° C. for 1 hour to 2 hours. The reaction solution is returned to room temperature, followed by addition of water, and also, 1N hydrochloric acid is added thereto until the pH thereof reaches 7. Furthermore, when hexane is added and ultrasonic waves are applied thereto, solids precipitate. The solids are filtrated through aspiration, followed by washing sequentially with water, and hexane or a solvent mixture of hexane/ethyl acetate=1:1. The washing is followed by drying, and as a result the compound expressed by Structural Formula (20) can be obtained.

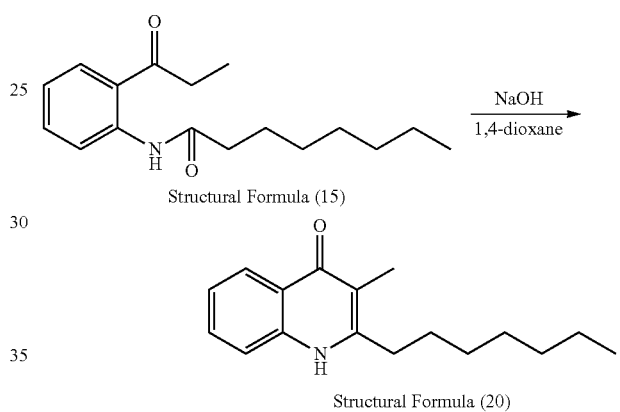

—Production of the Compound Expressed by Structural Formula (11)—

The compound expressed by the above Structural Formula (11) can be produced in the following manner, for example.

In an argon atmosphere, the compound expressed by the above Structural Formula (20) is dissolved in THF, and a THF solution of lithium t-butoxide is added thereto, followed by stirring at room temperature for 20 minutes. Chloromethyl thiocyanate is added dropwise thereto under cooling with ice, followed by further stirring at room temperature for 2 hours. The reaction is terminated by the addition of brine, and the mixture is extracted with ethyl acetate. The organic layer is dried with Glauber's salt, and then the residue is purified through silica gel chromatography (hexane:ethyl acetate=2:1), and as a result the compound expressed by Structural Formula (11) is obtained.

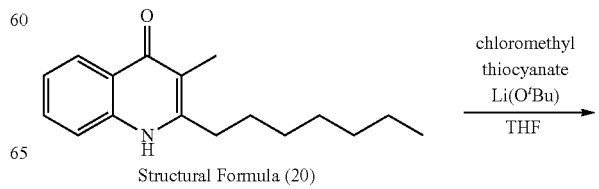

Structural Formula (20)

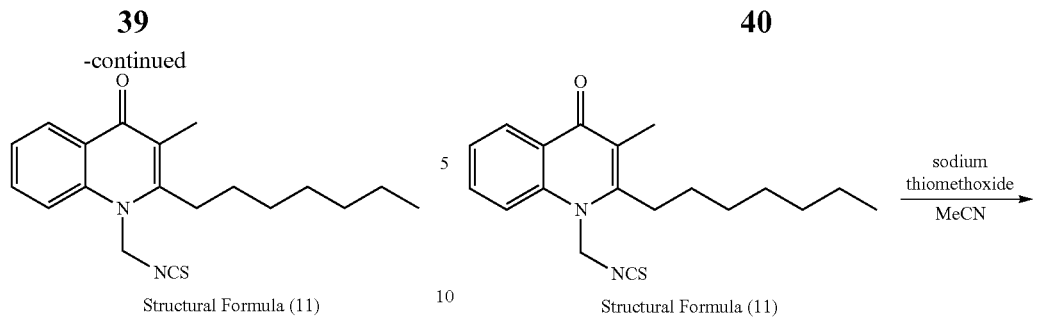

Structural Formula (11)

Method for Producing the Compound Expressed by the Above Structural Formula (12)

A method for producing the compound expressed by the above Structural Formula (12) is not particularly limited and may be appropriately selected depending on the intended purpose so long as it is a method including reacting a compound expressed by Structural Formula (11) below with sodium thiomethoxide in the presence of acetonitrile.

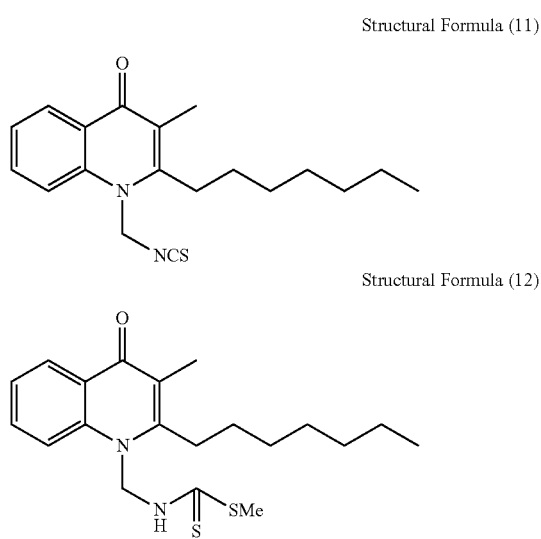

Structural Formula (11)

Structural Formula (12)

In the above Structural Formula (12), Me denotes a methyl group.

As a preferable aspect of the method for producing the compound expressed by the above Structural Formula (12), an aspect where the compound expressed by the above Structural Formula (11) is used as a starting material will be described below.

Note that, the compound expressed by the above Structural Formula (11) can be suitably produced by the above-described method.

—Production of the Compound Expressed by Structural Formula (12)—

The compound expressed by the above Structural Formula (12) can be produced in the following manner, for example.

Acetonitrile is added to a mixture of the compound expressed by the above Structural Formula (11) and sodium thiomethoxide, followed by stirring at room temperature for 20 minutes. Saturated sodium hydrogencarbonate aqueous solution is added thereto, and the mixture is extracted with ethyl acetate. The organic layer is dried with Glauber's salt, and then the residue is purified through silica gel chromatography (hexane:ethyl acetate=2:1), and as a result the compound expressed by Structural Formula (12) can be obtained.

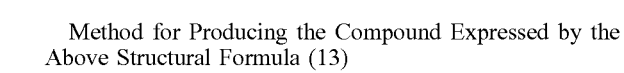

Structural Formula (11)

Structural Formula (12)

Method for Producing the Compound Expressed by the Above Structural Formula (13)

A method for producing the compound expressed by the above Structural Formula (13) is not particularly limited and may be appropriately selected depending on the intended purpose so long as it is a method including reacting a compound expressed by Structural Formula (11) below with sodium thiomethoxide in the presence of acetonitrile, to thereby obtain a reaction product, and reacting the reaction product and a methylating agent.

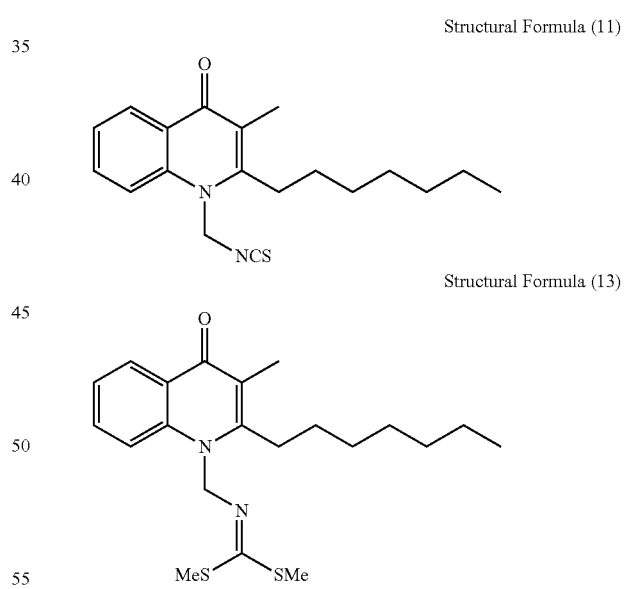

Structural Formula (11)

Structural Formula (13)

In the above Structural Formula (13), Me denotes a methyl group.

The methylating agent is not particularly limited and may be appropriately selected depending on the intended purpose. Examples thereof include iodomethane, methyl trifluoromethanesulfonate, dimethyl sulfate, and Meerwein reagents. One kind of the above methylating agent may be used alone, or two or more kinds thereof may be used in combination. Among them, iodomethane is preferable.

As a preferable aspect of the method for producing the compound expressed by the above Structural Formula (13), an aspect where the compound expressed by the above Structural Formula (11) is used as a starting material will be described below.

Note that, the compound expressed by the above Structural Formula (11) can be suitably produced by the above-described method.

—Production of the Compound Expressed by Structural Formula (13)—

The compound expressed by the above Structural Formula (13) can be produced in the following manner, for example.

Acetonitrile is added to a mixture of the compound expressed by the above Structural Formula (11) and sodium thiomethoxide, followed by stirring at room temperature for 20 minutes. Methyl iodide is added thereto at room temperature, and the mixture is further stirred for 30 minutes. Saturated sodium hydrogencarbonate aqueous solution is added thereto, and the mixture is extracted with ethyl acetate. The organic layer is dried with Glauber's salt, and then the residue is purified through silica gel chromatography (hexane:ethyl acetate=2:1), and as a result the compound expressed by Structural Formula (13) can be obtained.

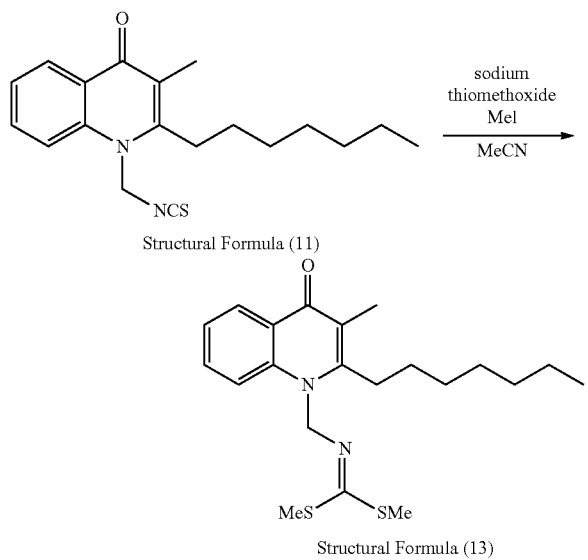

Reaction conditions, compounds to be used, amounts thereof, solvents, and the like in the production method for each of the compounds expressed by the above structural formulas are not particularly limited and may be appropriately selected depending on the intended purpose so long as the effects of the present invention are not impaired.

Whether each of the above compounds has a structure expressed by each of the above structural formulas can be determined with appropriately selected various analysis methods. Examples thereof include spectroscopies such as the above mass spectrometry, the above ultraviolet spectroscopy, the above infrared spectroscopy, the above proton nuclear magnetic resonance, and the above $^{13}C$ nuclear magnetic resonance.

(Compound-Containing Composition, Anti-Cancer Agent, and Anti-*Helicobacter pylori* Agent)

Compound-Containing Composition

A compound-containing composition of the present invention contains at least the compound expressed by any one of the above Structural Formulas (1) to (13); and, if necessary, further contains other ingredients.

One kind of the compound expressed by any one of the above Structural Formulas (1) to (13) may be used alone, or two or more kinds thereof may be used in combination.

An amount of the compound expressed by any one of the above Structural Formulas (1) to (13) contained in the compound-containing composition is not particularly limited and may be appropriately selected depending on the intended purpose. The above compound-containing composition may be the compound itself expressed by any one of the above Structural Formulas (1) to (13).

—Other Ingredients—

The above other ingredients are not particularly limited and may be appropriately selected depending on the intended purpose from pharmacologically acceptable carriers. Examples thereof include additives, supplements and water. These may be used alone or in combination of two or more thereof.

The above additives or supplements are not particularly limited and may be appropriately selected depending on the intended purpose. Examples thereof include a disinfectant, a preserving agent, a binding agent, a thickener, an adhesive agent, an integrating agent, a colorant, a stabilizer, a pH adjuster, a buffer, a tonicity agent, a solvent, an antioxidant, a UV rays-preventing agent, a preventing agent for precipitation of crystals, a defoaming agent, a property improving agent and an antiseptic agent.

The above disinfectant is not particularly limited and may be appropriately selected depending on the intended purpose. Examples thereof include cationic surfactants such as benzalkonium chloride, benzethonium chloride and cetylpyridinium chloride.

The above preserving agent is not particularly limited and may be appropriately selected depending on the intended purpose. Examples thereof include p-hydroxybenzoate esters, chlorobutanol and clesol.

The above binding agent, thickener and adhesive agent are not particularly limited and may be appropriately selected depending on the intended purpose. Examples thereof include starch, dextrin, cellulose, methyl cellulose, ethyl cellulose, carboxymethyl cellulose, hydroxyethyl cellulose, hydroxypropyol cellulose, hydroxypropyolmethyl cellulose, carboxymethyl starch, pullulan, sodium alginate, ammonium alginate, propylene glycol alginic acid esters, guar gum, locust bean gum, gum Arabic, xanthane gum, gelatin, casein, polyvinyl alcohol, polyethylene oxide, polyethylene glycol, ethylene/propylene block polymers, sodium polyacrylates and polyvinylpyrrolidone.

The above integrating agent is not particularly limited and may be appropriately selected depending on the intended purpose. Examples of the integrating agent include water, ethanol, propanol, simple syrup, glucose liquid, starch liquid, gelatin liquid, carboxymethyl cellulose, hydroxypropyl cellulose, hydroxypropyl starch, methyl cellulose, ethyl cellulose, shellac, calcium phosphate and polyvinylpyrrolidone.

The above colorant is not particularly limited and may be appropriately selected depending on the intended purpose. Examples thereof include titanium oxide and iron oxide.

The above stabilizer is not particularly limited and may be appropriately selected depending on the intended purpose. Examples thereof include tragacanth, gum Arabic, gelatin, sodium pyrosulfite, ethylenediaminetetraacetate (EDTA), thioglycolic acid and thiolactic acid.

The above pH adjuster or the buffer is not particularly limited and may be appropriately selected depending on the intended purpose. Examples thereof include sodium citrate, sodium acetate and sodium phosphate.

The above tonicity agent is not particularly limited and may be appropriately selected depending on the intended purpose. Examples thereof include sodium chloride and glucose.

An amount of the above other ingredients in the compound-containing composition is not particularly limited and may be appropriately selected depending on the intended purpose so long as the effects of the compound expressed by any one of the above Structural Formulas (1) to (13) are not impaired.

—Applications—

Since the above compound-containing composition contains the compound expressed by any one of the above Structural Formulas (1) to (13), it has excellent anti-cancer effects, excellent anti-*Helicobacter pylori* activity, and high safety, and can be suitably used for a pharmaceutical composition, an anti-cancer agent, an anti-*Helicobacter pylori* agent, and the like.

Note that, the above compound-containing composition may be used alone or in combination with a pharmaceutical drug containing another ingredient as an active ingredient. Also, the above compound-containing composition may be used in a state of being formulated into a pharmaceutical drug containing another ingredient as an active ingredient.

Anti-Cancer Agent

An anti-cancer agent of the present invention contains at least the compound expressed by the above Structural Formulas (1) to (13); and, if necessary, further contains other ingredients.

One kind of the compound expressed by any one of the above Structural Formulas (1) to (13) may be used alone, or two or more kinds thereof may be used in combination.

An amount of the compound expressed by any one of the above Structural Formulas (1) to (13) contained in the above anti-cancer agent is not particularly limited and may be appropriately selected depending on the intended purpose. The above anti-cancer agent may be the compound itself expressed by any one of the above Structural Formulas (1) to (13).

—Other Ingredients—

The above other ingredients are not particularly limited and may be appropriately selected depending on the intended purpose from pharmacologically acceptable carriers. Examples thereof include those similar to the other ingredients described for the above compound-containing composition. These may be used alone or in combination of two or more thereof.

An amount of the above other ingredients in the anti-cancer agent is not particularly limited and may be appropriately selected depending on the intended purpose so long as the effects of the compound expressed by any one of the above Structural Formulas (1) to (13) are not impaired.

—Applications—

Since the above anti-cancer agent contains the compound expressed by any one of the above Structural Formulas (1) to (13), it has excellent anti-cancer effects and high safety, and can be suitably used as a preventive agent or a therapeutic agent for a wide range of cancers such as stomach cancer, prostate cancer, lung cancer, colon cancer, pancreatic cancer, and breast cancer. Among them, it can be particularly suitably used for stomach cancer and colon cancer.

Note that, the above anti-cancer agent may be used alone or in combination with a pharmaceutical drug containing another ingredient as an active ingredient. Also, the above anti-cancer agent may be used in a state of being formulated into a pharmaceutical drug containing another ingredient as an active ingredient.

Also, as presented in the below-described Test Examples, the compound expressed by the above Structural Formulas (1) to (13) of the present invention can more suppress proliferation of cancer cells in the presence of normal stromal cells.

Since the above anti-cancer agent contains the compound expressed by any one of the above Structural Formulas (1) to (13), it can prevent development of cancer in an individual or treat an individual suffering from cancer by being administered to the individual. Therefore, the present invention also relates to a method for preventing or treating cancer, including administering the above anti-cancer agent to an individual.

Anti-*Helicobacter pylori* Agent

An anti-*Helicobacter pylori* agent of the present invention contains at least the compound expressed by any one of the above Structural Formulas (1) to (13); and, if necessary, further contains other ingredients.

One kind of the compound expressed by any one of the above Structural Formulas (1) to (13) may be used alone, or two or more kinds thereof may be used in combination.

An amount of the compound expressed by any one of the above Structural Formulas (1) to (13) contained in the anti-*Helicobacter pylori* agent is not particularly limited and may be appropriately selected depending on the intended purpose. The above anti-*Helicobacter pylori* agent may be the compound itself expressed by any one of the above Structural Formulas (1) to (13).

—Other Ingredients—

The above other ingredients are not particularly limited and may be appropriately selected depending on the intended purpose from pharmacologically acceptable carriers. Examples thereof include those similar to the other ingredients described for the above compound-containing composition. These may be used alone or in combination of two or more thereof.

An amount of the above other ingredients in the anti-*Helicobacter pylori* is not particularly limited and may be appropriately selected depending on the intended purpose so long as the effects of the compound expressed by any one of the above Structural Formulas (1) to (13) are not impaired.

—Applications—

Since the above anti-*Helicobacter pylori* agent contains the compound expressed by any one of the above Structural Formulas (1) to (13), it has excellent anti-*Helicobacter pylori* activity and high safety, and can be suitably used as a preventive agent or a therapeutic agent for stomach and duodenal disorders such as stomach ulcer and duodenal ulcer.

Note that, the above anti-*Helicobacter pylori* agent may be used alone or in combination with a pharmaceutical drug containing another ingredient as an active ingredient. Also, the above anti-*Helicobacter pylori* agent may be used in a state of being formulated into a pharmaceutical drug containing another ingredient as an active ingredient.

Since the above anti-*Helicobacter pylori* agent contains the compound expressed by any one of the above Structural Formulas (1) to (13), it can prevent an individual from being infected with *Helicobacter pylori* or treat an individual infected with *Helicobacter pylori* by being administered to the individual. Therefore, the present invention also relates to a method for preventing or treating an infectious disease caused by *Helicobacter pylori* including administering the above anti-*Helicobacter pylori* agent to an individual.

Also, the above anti-*Helicobacter pylori* agent can prevent development of stomach and duodenal disorders caused by *Helicobacter pylori* or treat an individual suffering from stomach and duodenal disorders caused *Helicobacter pylori* by being administered to the individual. Therefore, the present invention also relates to a method for preventing or treating stomach and duodenal disorders caused by *Helicobacter pylori*, including administering the above anti-*Helicobacter pylori* agent to an individual.

Dosage Form

The above dosage form of the above compound-containing composition, anti-cancer agent, and anti-*Helicobacter pylori* agent is not particularly limited and may be appropriately selected depending on the intended purpose. Examples thereof include a solid preparation, a semi-solid preparation and a liquid preparation. The above compound-containing composition, anti-cancer agent, and anti-*Helicobacter pylori* agent having any of these dosage forms can be produced according to a routine method.

—Solid Preparation—

The above solid preparation is not particularly limited and may be appropriately selected depending on the intended purpose. When it is used as an internal preparation, examples of the solid preparation include tablets, chewable tablets, foaming tablets, orally-disintegrating tablets, troches, drops, hard capsules, soft capsules, granules, powder, pills, dry syrups and infusions.

When the above solid preparation is an external preparation, examples of the solid preparation include suppositories, cataplasms and plasters.

—Semi-Solid Preparation—

The above semi-solid preparation is not particularly limited and may be appropriately selected depending on the intended purpose. When it is used as an internal preparation, examples of the semi-solid preparation include electuaries, chewing gums, whip and jelly.

When the above semi-solid preparation is used as an external preparation, examples of the semi-solid preparation include ointments, cream, mousse, inhaler and nasal gel.

—Liquid Preparation—

The above liquid preparation is not particularly limited and may be appropriately selected depending on the intended purpose. When it is used as an internal preparation, examples of the liquid preparation include syrups, drinks, suspensions and spirits.

When the above liquid preparation is used as an external preparation, examples of the liquid preparation include liquid, eye drops, aerosol and sprays.

Administration

An administration method, an administration dose, an administration period and an administration target of the above compound-containing composition, anti-cancer agent, and anti-*Helicobacter pylori* agent are not particularly limited and may be appropriately selected depending on the intended purpose.

Examples of the above administration method include a local administration method, an enteral administration method and a parenteral administration method.

The above administration dose is not particularly limited and may be appropriately selected considering various factors of an administration target, such as the age, body weight, constitution, symptom and the presence or absence of administration of a pharmaceutical drug or a medicament containing another ingredient as an active ingredient.

Animal species serving as the above administration target is not particularly limited and may be appropriately selected depending on the intended purpose. Examples thereof include human, monkey, pig, bovine, sheep, goat, dog, cat, mouse, rat and bird. Among them, they can be suitably used for human.

EXAMPLES

The present invention will next be described in detail by way of Production Examples and Test Examples. However, the present invention is not construed as being limited to these Production Examples and Test Examples.

Note that, data in the following Test Examples are representative ones from 2 or 3 independent experiments in which similar results were obtained. Statistical analysis was performed based on the Student's t-test.

Production Example 1

Production of the Compound Expressed by Structural Formula (3)

In the following manner, the compound expressed by the above Structural Formula (3) was produced through chemical synthesis.

—Production of the Compound Expressed by Structural Formula (14)—

In an argon atmosphere, aminobenzonitrile (15.0 g, 128 mmol) was dissolved in 300 mL of anhydrous tetrahydrofuran (hereinafter may be referred to as "THF"), and ethylmagnesium bromide (127 mL, 383 mmol) was added dropwise thereto in an ice bath. The mixture was stirred at room temperature for 12 hours, and then hydrochloric acid aqueous solution (10%) (100 mL) was added dropwise thereto in an ice bath. After completion of the dropwise addition, sodium hydroxide was added thereto in an ice bath, and the pH of the mixture was adjusted to 7. The organic layer was separated, and the aqueous layer was extracted with diethyl ether. The organic layers were combined and dried with Glauber's salt, and the solvent was evaporated. The residue was purified through silica gel chromatography (hexane: ethyl acetate=6:1), and as a result the compound expressed by Structural Formula (14) (9.7 g, 51%) was obtained.

Structural Formula (14)

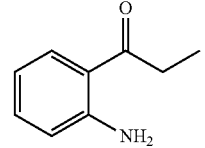

—Physico-Chemical Properties—

Physico-chemical properties of the compound expressed by Structural Formula (14) as follows.

(1) Appearance: yellow powder
(2) Melting point: 42° C.-43° C.
(3) Molecular formula: $C_9H_{11}ON$
(4) High resolution mass spectrometry (HRESI-MS)(m/z):
  Found: 150.0911 $(M+H)^+$
  Calcd: 150.0913 (as $C_9H_{12}ON$)
(5) Infrared absorption spectrum:
  Peaks of infrared absorption measured by the KBr tablet method are as follows.
  $v_{max}(KBr)cm^{-1}$: 3434, 3331, 1644, 1620
(6) Proton nuclear magnetic resonance spectrum (400 MHz, $CDCl_3$):

δ=1.21 (3H, q, J=7.3), 2.98 (2H, q, J=7.3), 6.27 (2H, br s), 6.62-6.67 (2H, m), 7.25 (1H, ddd, J=7.3, 5.0, 1.4), 7.76 (1H, dd, J=8.7, 1.4)
(7) $^{13}$C nuclear magnetic resonance spectrum (100 MHz, CDCl$_3$):
δ=8.70, 32.27, 115.70, 117.30, 117.84, 131.10, 134.05, 150.21, 203.33

—Production of the Compound Expressed by Structural Formula (17)—

In an argon atmosphere, the compound expressed by the above Structural Formula (14) (1 equivalent) was dissolved in methylene chloride, and triethylamine (2 equivalents) was added thereto. Furthermore, trans-8-methyl-6-nonenoyl chloride (1.1 equivalents), which is an acid chloride, was added dropwise to the mixture in an ice bath, followed by stirring at room temperature. The reaction was terminated with 0.1N hydrochloric acid, and the mixture was extracted with methylene chloride, followed by washing with saturated sodium hydrogencarbonate aqueous solution and brine. The combined organic layer was dried with Glauber's salt, and then the solvent was evaporated. The residue was purified through silica gel chromatography (hexane:ethyl acetate), and as a result the compound expressed by Structural Formula (17) was obtained.

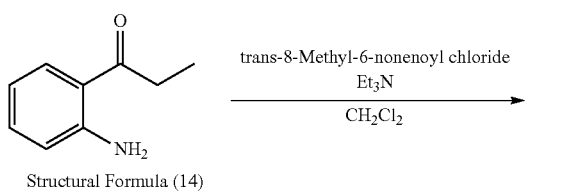

Structural Formula (14)

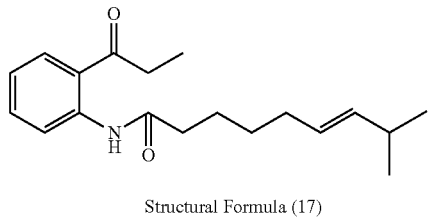

Structural Formula (17)

—Physico-Chemical Properties—
Physico-chemical properties of the compound expressed by Structural Formula (17) as follows.
(1) Appearance: colorless oily substance
(2) Molecular formula: C$_{19}$H$_{27}$O$_2$N
(3) High resolution mass spectrometry (HRESI-MS)(m/z):
 Found: 324.1932 (M+Na)$^+$
 Calcd: 324.1934 (as C$_{19}$H$_{27}$O$_2$NNa)
(4) Infrared absorption spectrum:
Peaks of infrared absorption measured by the KBr tablet method are as follows.
ν$_{max}$(KBr)cm$^{-1}$: 3255, 2956, 2937, 1655, 969, 754
(5) Proton nuclear magnetic resonance spectrum (400 MHz, CDCl$_3$):
δ=0.95 (6H, d, J=6.8), 1.22 (3H, t, J=7.1), 1.44 (2H, m), 1.75 (2H, m), 2.02 (2H, m), 2.22 (1H, m), 2.44 (2H, t, J=7.3), 3.07 (2H, q, J=7.1), 5.37 (2H, m), 7.09 (1H, ddd, J=8.0, 7.3, 1.1), 7.53 (1H, ddd, J=8.5, 7.3, 1.4), 7.92 (1H, dd, J=8.0, 1.4), 8.77 (1H, dd, J=8.5, 1.1), 11.77 (1H, br s) (6) $^{13}$C nuclear magnetic resonance spectrum (100 MHz, CDCl$_3$):
δ=8.45, 22.64, 25.03, 29.17, 30.96, 32.21, 33.14, 38.66, 120.84, 121.38, 122.14, 126.50, 130.65, 134.84, 138.03, 141.06, 172.68, 205.36

—Production of the Compound Expressed by Structural Formula (3)—

Sodium hydroxide (3.0 equivalents) was added to a 1,4-dioxane solution of the compound expressed by the above Structural Formula (17) (1 equivalent) (0.1 M), and the mixture was stirred at 110° C. for 1 hour to 2 hours. The reaction solution was returned to room temperature, followed by addition of water, and also, 1N hydrochloric acid was added thereto until the pH thereof reached 7. Furthermore, when hexane was added and ultrasonic waves were applied thereto, solids precipitated. The solids were filtrated through aspiration, followed by washing sequentially with water, hexane, and a solvent mixture of hexane/ethyl acetate=1:1. The washing was followed by drying, and as a result the compound expressed by Structural Formula (3) was obtained.

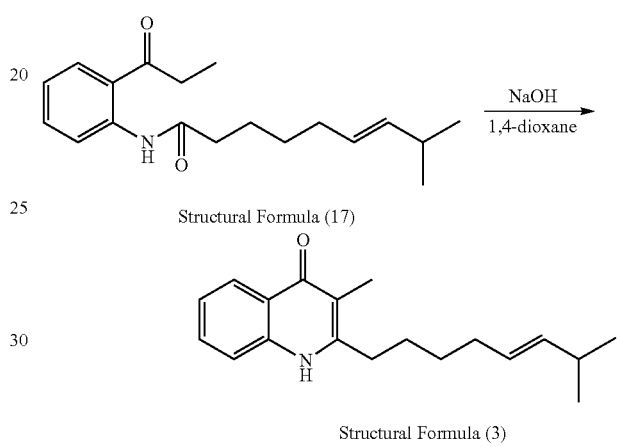

Structural Formula (17)

Structural Formula (3)

—Physico-Chemical Properties—
Physico-chemical properties of the compound expressed by Structural Formula (3) as follows.
(1) Appearance: white powder
(2) Melting point: 178° C.-181° C.
(3) Molecular formula: C$_{19}$H$_{25}$ON
(4) High resolution mass spectrometry (HRESI-MS)(m/z):
 Found: 284.2011 (M+H)$^+$
 Calcd: 284.2009 (as C$_{19}$H$_{26}$ON)
(5) Infrared absorption spectrum:
Peaks of infrared absorption measured by the KBr tablet method are as follows.
ν$_{max}$(KBr)cm$^{-1}$: 3064, 2957, 2933, 1670, 1638, 1614, 1555, 1500, 1371, 1358, 1152, 1028, 998, 967, 756, 691
(6) Proton nuclear magnetic resonance spectrum (600 MHz, CDCl$_3$):
δ=0.95 (6H, d, J=6.5), 1.44 (2H, m), 1.69 (2H, m), 2.01 (2H, q, J=6.8), 2.15 (3H, s), 2.21 (1H, m), 2.70 (2H, m), 5.27-5.32 (1H, m), 5.36-5.39 (1H, m), 7.28 (1H, ddd, J=8.2, 5.8, 1.0), 7.32 (1H, brd, J=8.2), 7.52 (1H, ddd, J=8.2, 5.5, 1.4), 8.36 (1H, dd, J=8.2, 1.4), 8.65 (1H, br)
(7) $^{13}$C nuclear magnetic resonance spectrum (150 MHz, CDCl$_3$):
δ=10.65, 22.64, 27.77, 29.22, 30.98, 32.09, 32.96, 115.72, 116.69, 123.00, 123.66, 126.14, 126.30, 131.25, 138.49, 138.78, 148.54, 178.16

Production Example 2

Production of the Compound Expressed by Structural Formula (4)

In the following manner, the compound expressed by the above Structural Formula (4) was produced through chemical synthesis.

—Production of the Compound Expressed by Structural Formula (18)—

In an argon atmosphere, the compound expressed by the above Structural Formula (14) (1 equivalent) was dissolved in methylene chloride, followed by addition of triethylamine (2 equivalents). Furthermore, isovaleryl chloride (1.1 equivalents), which is an acid chloride, was added dropwise to the mixture in an ice bath, followed by stirring at room temperature. The reaction was terminated with 0.1N hydrochloric acid, and the mixture was extracted with methylene chloride, followed by washing with saturated sodium hydrogencarbonate aqueous solution and brine. The combined organic layer was dried with Glauber's salt, and then the solvent was evaporated. The residue was purified through silica gel chromatography (hexane:ethyl acetate), and as a result the compound expressed by Structural Formula (18) was obtained.

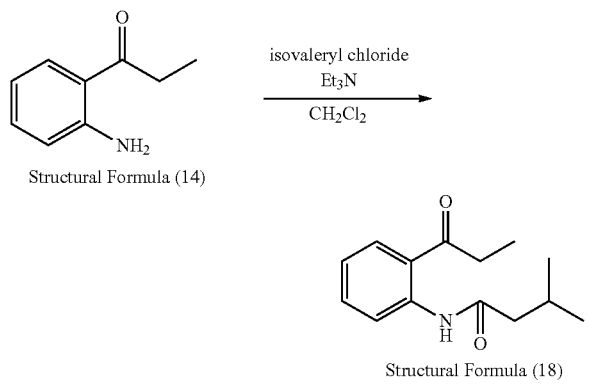

—Physico-Chemical Properties—

Physico-chemical properties of the compound expressed by Structural Formula (18) as follows.

(1) Appearance: colorless oily substance
(2) Molecular formula: $C_{14}H_{19}O_2N$
(3) High resolution mass spectrometry (HRESI-MS)(m/z):
    Found: 256.1306 (M+Na)$^+$
    Calcd: 256.1308 (as $C_{14}H_{19}O_2NNa$)
(4) Infrared absorption spectrum:
    Peaks of infrared absorption measured by the KBr tablet method are as follows.
    $\nu_{max}(KBr)cm^{-1}$: 3254, 2959, 1697, 1376, 754
(5) Proton nuclear magnetic resonance spectrum (400 MHz, CDCl$_3$):
    δ=1.01 (6H, d, J=6.4), 1.22 (3H, t, J=7.1), 2.24 (1H, m), 2.31 (2H, d, J=6.4), 3.07 (2H, q, J=7.1), 7.10 (1H, ddd, J=8.4, 6.8, 1.1), 7.53 (1H, ddd, J=8.5, 6.8, 1.4), 7.93 (1H, dd, J=8.0, 1.4), 8.78 (1H, d, J=8.5), 11.75 (1H, br s)
(6) $^{13}C$ nuclear magnetic resonance spectrum (100 MHz, CDCl$_3$):
    δ=8.45, 22.46, 26.20, 33.15, 48.09, 120.81, 121.38, 122.16, 130.59, 134.85, 141.02, 172.14, 205.40

—Production of the Compound Expressed by Structural Formula (4)—

Sodium hydroxide (3.0 equivalents) was added to a 1,4-dioxane solution of the compound expressed by the above Structural Formula (18) (1 equivalent) (0.1 M), and the mixture was stirred at 110° C. for 1 hour to 2 hours. The reaction solution was returned to room temperature, followed by addition of water, and also, 1N hydrochloric acid was added thereto until the pH thereof reached 7. Furthermore, when hexane was added and ultrasonic waves were applied thereto, solids precipitated. The solids were filtrated through aspiration, followed by washing sequentially with water, hexane, and a solvent mixture of hexane/ethyl acetate=1:1. The washing was followed by drying, and as a result the compound expressed by Structural Formula (4) was obtained.

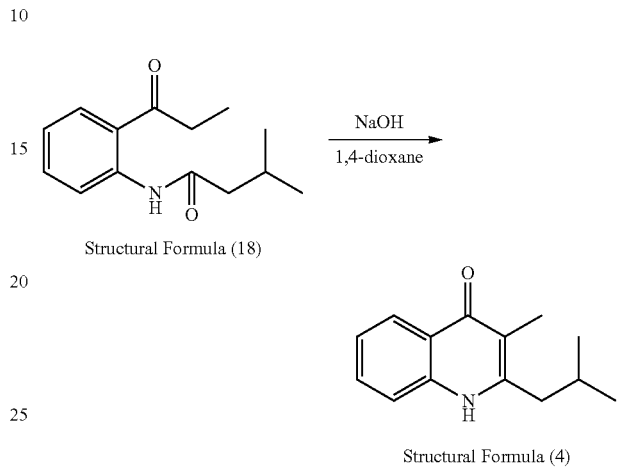

—Physico-Chemical Properties—

Physico-chemical properties of the compound expressed by Structural Formula (4) as follows.

(1) Appearance: white powder
(2) Melting point: 240° C.-244° C.;
(3) Molecular formula: $C_{14}H_{17}ON$
(4) High resolution mass spectrometry (HRESI-MS)(m/z):
    Found: 216.1385 (M+H)$^+$
    Calcd: 216.1383 (as $C_{14}H_{18}ON$)
(5) Infrared absorption spectrum:
    Peaks of infrared absorption measured by the KBr tablet method are as follows.
    $\nu_{max}(KBr)cm^{-1}$: 3059, 2956, 1636, 1609, 1554, 1505, 1369, 1359, 1189, 998, 762, 695
(6) Proton nuclear magnetic resonance spectrum (400 MHz, DMSO-d$_6$):
    δ=0.89 (6H, d, J=6.6), 1.94 (3H, s), 1.99 (1H, m), 2.53 (2H, d, J=7.5), 7.18 (1H, ddd, J=8.2, 6.6, 1.4), 7.46 (1H, d, J=8.2), 7.52 (1H, ddd, J=8.2, 6.6, 1.4), 8.01 (1H, dd, J=8.2, 1.1), 11.23 (1H, br s)
(7) $^{13}C$ nuclear magnetic resonance spectrum (100 MHz, DMSO-d$_6$):
    δ=11.03, 22.28, 28.30, 114.68, 117.74, 122.39, 123.00, 125.18, 131.08, 139.33, 148.76, 176.43

Production Example 3

Production of the Compound Expressed by Structural Formula (8)

In the following manner, the compound expressed by the above Structural Formula (8) was produced through chemical synthesis.

—Production of the Compound Expressed by Structural Formula (19)—

In an argon atmosphere, the compound expressed by the above Structural Formula (14) (1 equivalent) was dissolved in methylene chloride, followed by addition of triethylamine (2 equivalents). Furthermore, cinnamoyl chloride (1.1 equivalents), which is an acid chloride, was added dropwise to the mixture in an ice bath, followed by stirring at room temperature. The reaction was terminated with 0.1N hydrochloric acid, and the mixture was extracted with methylene chloride, followed by washing with saturated sodium hydrogencarbonate aqueous solution and brine. The combined organic layer was dried with Glauber's salt, and then the solvent was evaporated. The residue was purified through silica gel chromatography (hexane:ethyl acetate), and as a result the compound expressed by Structural Formula (19) was obtained.

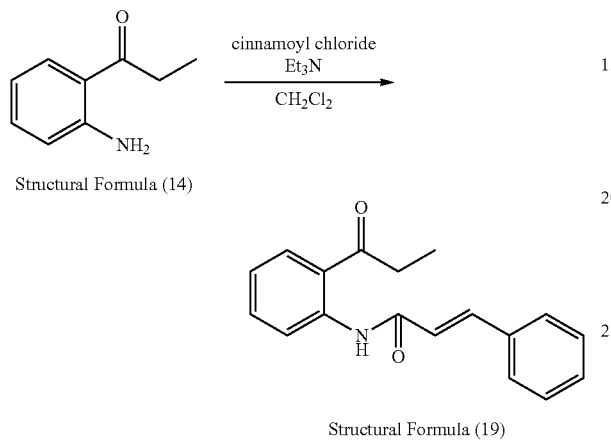

Structural Formula (14)

Structural Formula (19)

—Physico-Chemical Properties—

Physico-chemical properties of the compound expressed by Structural Formula (19) as follows.
(1) Appearance: white powder
(2) Melting point: 109° C.-111° C.
(3) Molecular formula: $C_{18}H_{17}O_2N$
(4) High resolution mass spectrometry (HRESI-MS)(m/z):
   Found: 302.1151 (M+Na)$^+$
   Calcd: 302.1152 (as $C_{18}H_{17}O_2NNa$)
(5) Infrared absorption spectrum:
   Peaks of infrared absorption measured by the KBr tablet method are as follows.
   $v_{max}$(KBr)cm$^{-1}$: 3223, 3023, 1677, 1653, 751, 727
(6) Proton nuclear magnetic resonance spectrum (400 MHz, CDCl$_3$):
   δ=1.25 (3H, t, J=7.1), 3.11 (2H, q, J=7.1), 6.65 (1H, d, J=15.5), 7.13 (1H, ddd, J=8.0, 7.1, 1.1), 7.36-7.44 (3H, m), 7.56-7.62 (3H, m), 7.76 (1H, d, J=15.5), 7.96 (1H, dd, J=8.0, 1.4), 8.91 (1H, dd, J=8.5, 1.4), 12.10 (1H, br s)
(7) $^{13}$C nuclear magnetic resonance spectrum (100 MHz, CDCl$_3$):
   δ=8.43, 33.15, 121.06, 121.47, 122.09, 122.41, 128.07, 128.83, 129.95, 130.69, 134.66, 134.93, 141.25, 142.25, 164.85, 205.56

—Production of the Compound Expressed by Structural Formula (8)—

Sodium hydroxide (3.0 equivalents) was added to a 1,4-dioxane solution of the compound expressed by the above Structural Formula (19) (1 equivalent) (0.1 M), and the mixture was stirred at 110° C. for 1 hour to 2 hours. The reaction solution was returned to room temperature, followed by addition of water, and also, 1N hydrochloric acid was added thereto until the pH thereof reached 7. Furthermore, when hexane was added and ultrasonic waves were applied thereto, solids precipitated. The solids were filtrated through aspiration, followed by washing sequentially with water and hexane. The washing was followed by drying, and as a result the compound expressed by Structural Formula (8) was obtained.

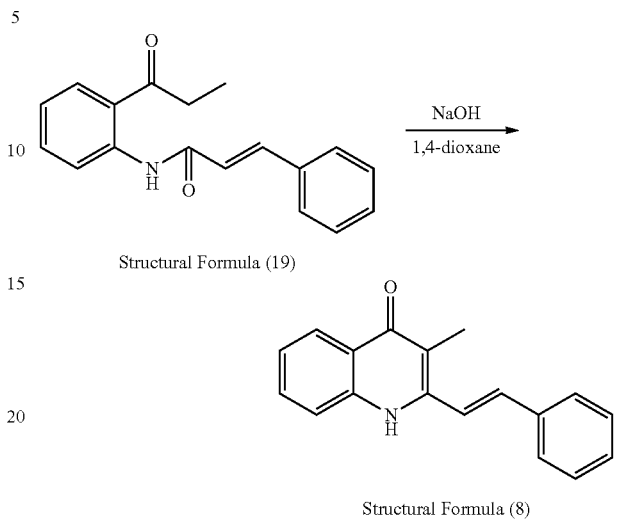

Structural Formula (19)

Structural Formula (8)

—Physico-Chemical Properties—

Physico-chemical properties of the compound expressed by Structural Formula (8) as follows.
(1) Appearance: yellow powder
(2) Melting point: >260° C.
(3) Molecular formula: $C_{18}H_{15}ON$
(4) High resolution mass spectrometry (HRESI-MS)(m/z):
   Found: 284.1046 (M+Na)$^+$
   Calcd: 284.1046 (as $C_{18}H_{15}ONNa$)
(5) Infrared absorption spectrum:
   Peaks of infrared absorption measured by the KBr tablet method are as follows.
   $v_{max}$(KBr)cm$^{-1}$: 3064, 2938, 1628, 1570, 1507, 1387, 1359, 1187, 965, 755, 690
(6) Proton nuclear magnetic resonance spectrum (400 MHz, DMSO-d$_6$):
   δ=2.13 (3H, s), 7.21 (1H, ddd, J=8.5, 6.8, 1.1), 7.32-7.50 (5H, m), 7.55-7.59 (1H, m), 7.67-7.72 (3H, m), 8.03 (1H, dd, J=8.2, 1.4), 11.20 (1H, s)
(7) $^{13}$C nuclear magnetic resonance spectrum (100 MHz, DMSO-d$_6$):
   δ=10.66, 115.68, 118.18, 121.14, 122.55, 123.13, 125.14, 127.57, 129.16, 129.30, 131.61, 135.11, 135.94, 139.75, 143.14, 176.76

Production Example 4

Production of the Compound Expressed by Structural Formula (5)

In the following manner, the compound expressed by the above Structural Formula (5) was produced through chemical synthesis.

—Production of the Compound Expressed by Structural Formula (16)—

In an argon atmosphere, the compound expressed by the above Structural Formula (14) (1 equivalent) was dissolved in methylene chloride, and triethylamine (2 equivalents) was added thereto. Furthermore, nonanoyl chloride (1.1 equivalents), which is an acid chloride, was added dropwise to the mixture in an ice bath, followed by stirring at room temperature. The reaction was terminated with 0.1N hydrochloric acid, and the mixture was extracted with methylene chloride, followed by washing with saturated sodium hydrogencarbonate aqueous solution and brine. The combined organic layer was dried with Glauber's salt, and then the solvent was evaporated. The residue was purified through silica gel chromatography (hexane:ethyl acetate), and as a result the compound expressed by Structural Formula (16) was obtained.

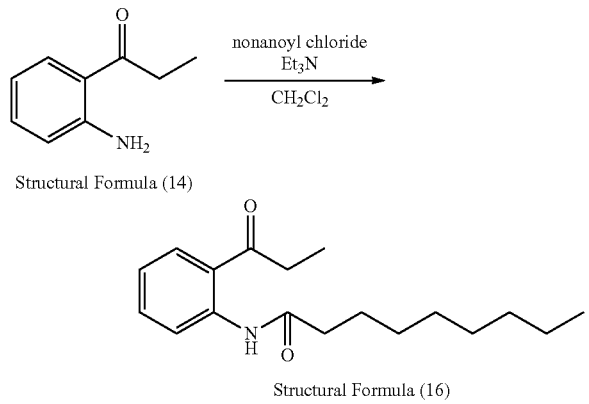

Structural Formula (16)

—Physico-Chemical Properties—

Physico-chemical properties of the compound expressed by Structural Formula (16) as follows.

(1) Appearance: colorless oily substance
(2) Molecular formula: $C_{18}H_{27}O_2N$
(3) High resolution mass spectrometry (HRESI-MS)(m/z):
   Found: 312.1933 (M+Na)$^+$
   Calcd: 312.1934 (as $C_{18}H_{27}O_2NNa$)
(4) Infrared absorption spectrum:
   Peaks of infrared absorption measured by the KBr tablet method are as follows.
   $v_{max}$(KBr)cm$^{-1}$: 3255, 2953, 2928, 1698, 754
(5) Proton nuclear magnetic resonance spectrum (400 MHz, CDCl$_3$):
   δ=0.87 (3H, t, J=6.6), 1.20-1.41 (13H, m), 1.74 (2H, m), 2.43 (2H, t, J=7.6), 3.08 (2H, q, J=7.3), 7.09 (1H, ddd, J=8.0, 7.3, 1.1), 7.53 (1H, ddd, J=8.5, 7.3, 1.6), 7.93 (1H, dd, J=8.0, 1.6), 8.77 (1H, dd, J=8.5, 1.1), 11.76 (1H, br s)
(6) $^{13}$C nuclear magnetic resonance spectrum (100 MHz, CDCl$_3$):
   δ=8.54, 14.07, 22.63, 25.55, 29.14, 29.22, 29.28, 31.87, 33.20, 38.80, 120.85, 121.96, 122.12, 130.57, 134.84, 141.08, 172.80, 205.37

—Production of the Compound Expressed by Structural Formula (21)—

Sodium hydroxide (3.0 equivalents) was added to a 1,4-dioxane solution of the compound expressed by the above Structural Formula (16) (1 equivalent) (0.1 M), and the mixture was stirred at 110° C. for 1 hour to 2 hours. The reaction solution was returned to room temperature, followed by addition of water, and also, 1N hydrochloric acid was added thereto until the pH thereof reached 7. Furthermore, when hexane was added and ultrasonic waves were applied thereto, solids precipitated. The solids were filtrated through aspiration, followed by washing with water and hexane. The washing was followed by drying, and as a result the compound expressed by Structural Formula (21) was obtained.

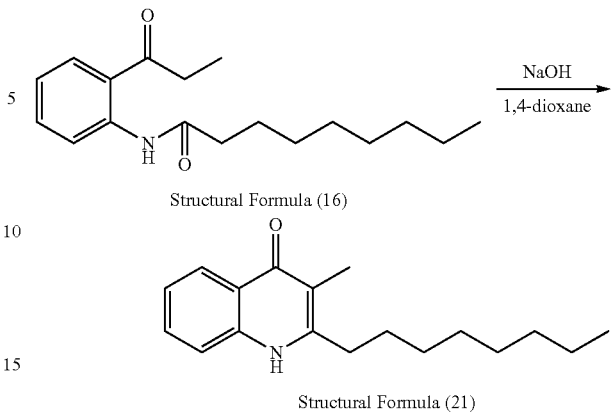

—Physico-Chemical Properties—

Physico-chemical properties of the compound expressed by Structural Formula (21) as follows.

(1) Appearance: white powder
(2) Melting point: 228° C.-231° C.
(3) Molecular formula: $C_{18}H_{25}ON$
(4) High resolution mass spectrometry (HRESI-MS)(m/z):
   Found: 272.2010 (M+H)$^+$
   Calcd: 272.2009 (as $C_{18}H_{26}ON$)
(5) Infrared absorption spectrum:
   Peaks of infrared absorption measured by the KBr tablet method are as follows.
   $v_{max}$(KBr)cm$^{-1}$: 3059, 2952, 2923, 1638, 1607, 1555, 1500, 1190, 998, 754, 693
(6) Proton nuclear magnetic resonance spectrum (400 MHz, DMSO-d$_6$):
   δ=0.80 (3H, t, J=6.6), 1.19-1.35 (10H, m), 1.59 (2H, m), 1.94 (3H, s), 2.62 (2H, t, J=7.5), 7.18 (1H, dd, J=8.2, 6.6), 7.45 (1H, d, J=8.0), 7.51 (1H, ddd, J=8.2, 6.7, 1.4), 8.00 (1H, dd, J=8.0, 1.4), 11.31 (1H, br s)
(7) $^{13}$C nuclear magnetic resonance spectrum (100 MHz, DMSO-d$_6$):
   δ=10.48, 14.15, 22.26, 28.49, 28.80, 28.92, 29.04, 31.43, 31.84, 113.87, 117.73, 122.39, 123.06, 125.18, 131.05, 139.36, 149.82, 176.39

—Production of the Compound Expressed by Structural Formula (5)—

In an argon atmosphere, the compound expressed by the above Structural Formula (21) (800 mg, 2.95 mmol) was dissolved in THF (20 mL), and a THF solution of lithium t-butoxide (4.4 mL, 4.42 mmol) was added thereto, followed by stirring at room temperature for 20 minutes. Next, methyl bromoacetate (1.4 mL, 14.7 mmol) was added thereto, and the mixture was further stirred under reflux for 12 hours. The reaction was terminated by the addition of water, and the mixture was extracted with ethyl acetate. The organic layer was dried with Glauber's salt, and then the solvent was evaporated. The residue was purified through silica gel chromatography (hexane:ethyl acetate=2:1), and as a result the compound expressed by Structural Formula (5) (780 mg, 76%) was obtained.

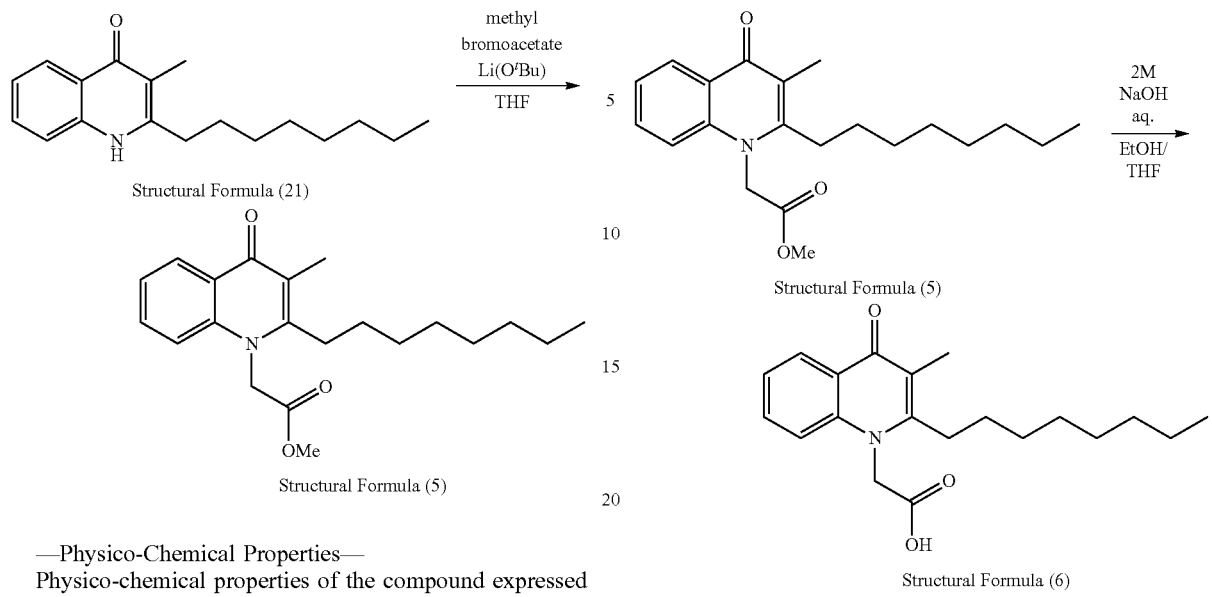

Structural Formula (21)

Structural Formula (5)

Structural Formula (6)

—Physico-Chemical Properties—

Physico-chemical properties of the compound expressed by Structural Formula (5) as follows.
(1) Appearance: colorless oily substance
(2) Molecular formula: $C_{21}H_{29}O_3N$
(3) High resolution mass spectrometry (HRESI-MS)(m/z):
 Found: 344.2222 (M+H)$^+$
 Calcd: 344.2220 (as $C_{21}H_{30}O_3N$)
(4) Infrared absorption spectrum:
 Peaks of infrared absorption measured by the KBr tablet method are as follows.
 $\nu_{max}$(KBr)cm$^{-1}$: 2953, 2922, 1743, 1635, 1617, 1558, 1507, 1214, 994, 760, 688
(5) Proton nuclear magnetic resonance spectrum (400 MHz, CDCl$_3$):
 δ=0.89 (3H, t, J=6.6), 1.21-1.51 (10H, m), 1.60 (2H, m), 2.22 (3H, s), 2.74 (2H, br), 3.80 (3H, s), 4.90 (2H, s), 7.20 (1H, d, J=8.7), 7.33 (1H, ddd, J=8.0, 6.8, 0.7), 7.58 (1H, ddd, J=8.7, 7.1, 1.6), 8.47 (1H, dd, J=8.0, 1.6)
(6) $^{13}$C nuclear magnetic resonance spectrum (100 MHz, CDCl$_3$):
 δ=11.65, 14.06, 22.60, 28.06, 29.13, 29.17, 29.75, 30.93, 31.75, 48.47, 53.01, 114.19, 117.55, 123.11, 124.79, 127.30, 131.89, 140.66, 150.66, 168.69, 177.39

Production Example 5

Production of the Compound Expressed by Structural Formula (6)

In the following manner, the compound expressed by the above Structural Formula (6) was produced through chemical synthesis.

—Production of the Compound Expressed by Structural Formula (6)—

The compound expressed by the above Structural Formula (5) (890 mg, 2.59 mmol) was dissolved in a solvent mixture of ethanol (hereinafter may be referred to as "EtOH", 5 mL) and THF (5 mL), and sodium hydroxide aqueous solution (2 M) (2.0 mL) was added thereto, followed by stirring at room temperature for 2 hours. The pH of the mixture was adjusted to 4 by the addition of 11\T hydrochloric acid in an ice bath, and the mixture was extracted with ethyl acetate. The organic layer was dried with Glauber's salt and the solvent was evaporated, and as a result the compound expressed by Structural Formula (6) (530 mg, 62%) was obtained.

—Physico-Chemical Properties—

Physico-chemical properties of the compound expressed by Structural Formula (6) as follows.
(1) Appearance: white powder
(2) Melting point: 161° C.-163° C.
(3) Molecular formula: $C_{20}H_{27}O_3N$
(4) High resolution mass spectrometry (HRESI-MS)(m/z):
 Found: 330.2063 (M+H)$^+$
 Calcd: 330.2064 (as $C_{20}H_{28}O_3N$)
(5) Infrared absorption spectrum:
 Peaks of infrared absorption measured by the KBr tablet method are as follows.
 $\nu_{max}$(KBr)cm$^{-1}$: 2955, 2925, 2853, 1725, 1635, 1593, 1506, 1191, 976, 760, 689
(6) Proton nuclear magnetic resonance spectrum (400 MHz, CDCl$_3$):
 δ=0.87 (3H, t, J=6.4), 1.20-1.65 (12H, m), 2.19 (3H, s), 2.80 (2H, br), 4.98 (2H, br), 7.26 (1H, t, J=8.0), 7.42 (1H, d, J=8.7), 7.54 (1H, ddd, J=8.7, 6.8, 1.1), 8.39 (1H, dd, J=8.0, 1.1)
(7) $^{13}$C nuclear magnetic resonance spectrum (100 MHz, CDCl$_3$):
 δ=11.91, 14.06, 22.68, 27.85, 29.12, 29.78, 31.26, 31.73, 49.71, 115.46, 117.21, 123.86, 123.94, 126.69, 132.47, 140.53, 154.22, 169.35, 176.57

Production Example 6

Production of the Compound Expressed by Structural Formula (1)

In the following manner, the compound expressed by the above Structural Formula (1) was produced through chemical synthesis.

—Production of the Compound Expressed by Structural Formula (1)—

The compound expressed by the above Structural Formula (21) (100 mg, 0.37 mmol) was dissolved in N,N-dimethylformamide (hereinafter may be referred to as "DMF", 5 mL), and potassium carbonate (332 mg, 2.40 mmol) and methyl bromoacetate (53.0 mL, 0.56 mmol) were added thereto, followed by stirring at 80° C. for 12 hours. The reaction was terminated by the addition of water, and the mixture was extracted with ethyl acetate. The organic layer was dried with Glauber's salt, and then the solvent was evaporated. The residue was purified through silica gel chromatography (hexane:ethyl acetate=2:1), and as a result the compound expressed by Structural Formula (1) (83.0 mg, 66%) was obtained.

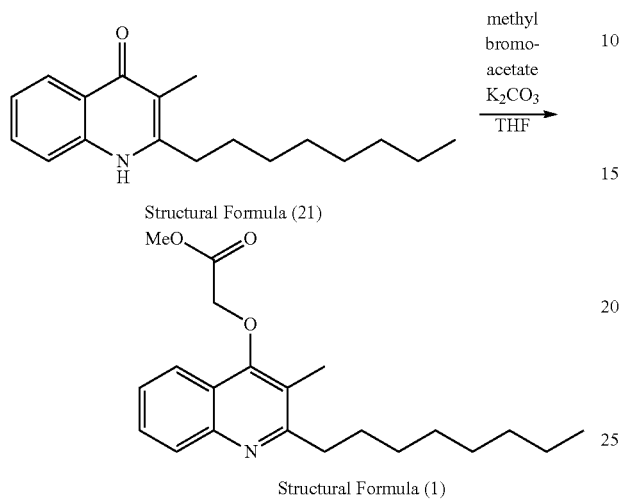

Structural Formula (21)

Structural Formula (1)

thereto, followed by stirring at room temperature for 2 hours. The pH of the mixture was adjusted to 4 by the addition of 1N hydrochloric acid in an ice bath, and the mixture was extracted with ethyl acetate. The organic layer was dried with Glauber's salt and the solvent was evaporated, and as a result the compound expressed by Structural Formula (2) (68.2 mg, 88%) was obtained.

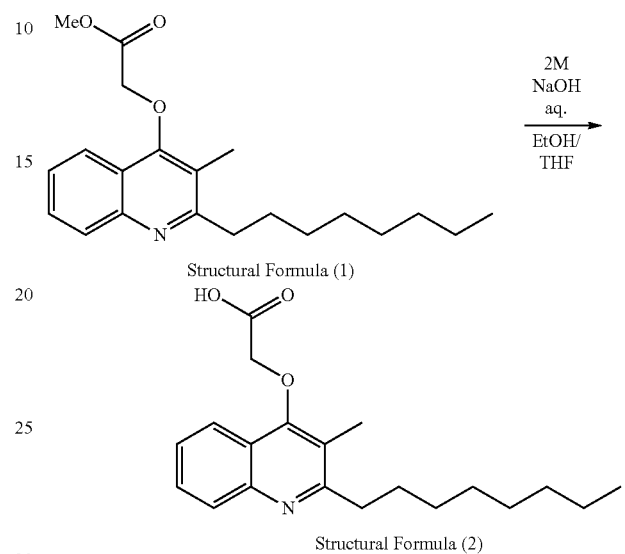

Structural Formula (1)

Structural Formula (2)

—Physico-Chemical Properties—

Physico-chemical properties of the compound expressed by Structural Formula (1) as follows.
(1) Appearance: colorless oily substance
(2) Molecular formula: $C_{21}H_{29}O_3N$
(3) High resolution mass spectrometry (HRESI-MS)(m/z):
Found: 344.2221 (M+H)$^+$
Calcd: 344.2220 (as $C_{211}$-13003N)
(4) Infrared absorption spectrum:
Peaks of infrared absorption measured by the KBr tablet method are as follows.
$v_{max}$(KBr)cm$^{-1}$: 2953, 2925, 2854, 1765, 1618, 1596, 1437, 1123, 968, 768, 680
(5) Proton nuclear magnetic resonance spectrum (400 MHz, CDCl$_3$):
δ=0.87 (3H, t, J=6.6), 1.20-1.48 (10H, m), 1.71 (2H, m), 2.43 (3H, s), 2.95 (2H, m), 3.86 (3H, s), 4.62 (2H, s), 7.47 (1H, ddd, J=8.2, 6.8, 1.1), 7.62 (1H, ddd, J=8.4, 6.8, 1.3), 8.00 (1H, d, J=8.4), 8.05 (1H, d, J=8.2)
(6) $^{13}$C nuclear magnetic resonance spectrum (100 MHz, CDCl$_3$):
δ=11.90, 14.08, 22.63, 28.99, 29.23, 29.49, 29.86, 31.83, 37.02, 52.32, 70.26, 120.85, 120.73, 121.39, 121.76, 125.73, 128.82, 128.85, 147.84, 159.03, 164.32, 168.95

Production Example 7

Production of the Compound Expressed by Structural Formula (2)

In the following manner, the compound expressed by the above Structural Formula (2) was produced through chemical synthesis.

—Production of the Compound Expressed by Structural Formula (2)—

The compound expressed by the above Structural Formula (1) (80.0 mg, 0.233 mmol) was dissolved in a solvent mixture of EtOH (1 mL) and THF (1 mL), and sodium hydroxide aqueous solution (2 M) (0.5 ml) was added —Physico-Chemical Properties—

Physico-chemical properties of the compound expressed by Structural Formula (2) as follows.
(1) Appearance: white powder
(2) Melting point: 59° C.-62° C.
(3) Molecular formula: $C_{20}H_{27}O_3N$
(4) High resolution mass spectrometry (HRESI-MS)(m/z):
Found: 330.2064 (M+H)$^+$
Calcd: 330.2064 (as $C_{20}H_{28}O_3N$)
(5) Infrared absorption spectrum:
Peaks of infrared absorption measured by the KBr tablet method are as follows.
$v_{max}$(KBr)cm$^{-1}$: 2927, 2855, 2713, 1736, 1642, 1589, 1227, 1181, 1078, 764, 724
(6) Proton nuclear magnetic resonance spectrum (600 MHz, Methanol-d$_4$):
δ=0.88 (3H, t, J=6.8), 1.25-1.41 (8H, m), 1.50 (2H, m), 1.78 (2H, m), 2.54 (3H, s), 3.15 (2H, t, m), 4.92 (2H, s), 7.54 (1H, ddd, J=8.2, 7.2, 1.0), 7.92 (1H, ddd, J=8.5, 6.8, 1.0), 8.07 (1H, brd, J=8.5), 8.42 (1H, brd, J=8.2)
(7) $^{13}$C nuclear magnetic resonance spectrum (150 MHz, Methanol-d$_4$):
δ=12.23, 14.40, 23.67, 29.93, 30.27, 30.34, 30.74, 32.97, 35.07, 72.72, 122.81, 123.71, 123.85, 124.62, 129.16, 133.85, 142.14, 164.30, 167.46, 171.91

Production Example 8

Production of the Compound Expressed by Structural Formula (7)

In the following manner, the compound expressed by the above Structural Formula (7) was produced through chemical synthesis.

—Production of the Compound Expressed by Structural Formula (7)—

In an argon atmosphere, the compound expressed by the above Structural Formula (21) (50.0 mg, 0.184 mmol) was dissolved in THF (1.0 mL), and lithium t-butoxide (29.4 mg, 0.37 mmol) was added thereto, followed by stirring at room temperature for 20 minutes. Next, cyanogen bromide (0.6 mL, 1.84 mmol) was added thereto, and the mixture was stirred at room temperature for 2 hours. The reaction was terminated by the addition of water, and the mixture was extracted with ethyl acetate. The organic layer was dried with Glauber's salt, and then the solvent was evaporated. The residue was purified through silica gel chromatography (hexane:ethyl acetate=2:1), and as a result the compound expressed by Structural Formula (7) (34.0 mg, 62%) was obtained.

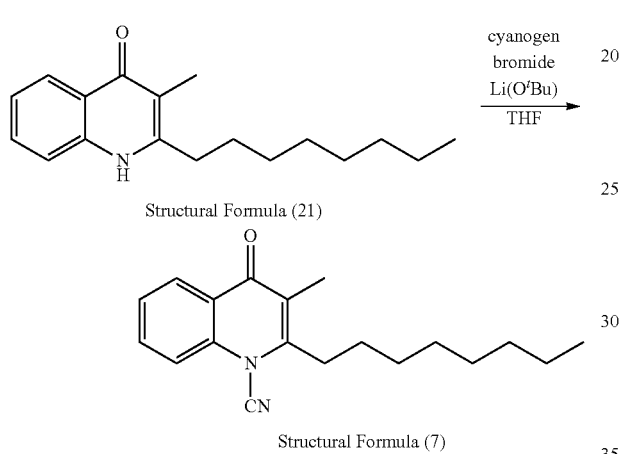

—Physico-Chemical Properties—
Physico-chemical properties of the compound expressed by Structural Formula (7) as follows.
(1) Appearance: colorless oily substance
(2) Molecular formula: $C_{19}H_{24}ON_2$
(3) High resolution mass spectrometry (HRESI-MS)(m/z):
  Found: 297.1961 $(M+H)^+$
  Calcd: 297.1961 (as $C_{19}H_{25}ON_2$)
(4) Infrared absorption spectrum:
Peaks of infrared absorption measured by the KBr tablet method are as follows.
$\nu_{max}(KBr)cm^{-1}$: 2961, 2926, 2853, 2237, 1628, 1576, 1470, 1292, 1191, 761, 693
(5) Proton nuclear magnetic resonance spectrum (400 MHz, $CDCl_3$):
  δ=0.87 (3H, t, J=6.8), 1.20-1.50 (10H, m), 1.71 (2H, m), 2.15 (3H, s), 2.93 (2H, m), 7.47 (1H, m), 7.73 (2H, m), 8.33 (1H, ddd, J=8.0, 0.92, 1.1)
(6) $^{13}C$ nuclear magnetic resonance spectrum (100 MHz, $CDCl_3$):
  δ=11.20, 14.05, 22.59, 28.00, 29.07, 29.11, 29.42, 31.73, 31.80, 106.42, 116.28, 120.30, 123.35, 126.23, 127.08, 133.34, 137.25, 146.10, 177.31

Production Example 9

Production of the Compound Expressed by Structural Formula (9)

In the following manner, the compound expressed by the above Structural Formula (9) was produced through chemical synthesis.

—Production of the Compound Expressed by Structural Formula (9)—

The compound expressed by the above Structural Formula (6) (100 mg, 0.30 mmol) was suspended in THF (5 mL), and triethylamine (50.8 mL, 0.36 mmol), diphenylphosphoryl azide (hereinafter may be referred to as "DPPA", 72.0 mL, 0.33 mmol), and sodium thiomethoxide (23.0 mg, 0.334 mmol) were added thereto, and the mixture was stirred under reflux for 2 hours. Ammonium chloride aqueous solution was added thereto, and the mixture was extracted with ethyl acetate. The organic layer was dried with Glauber's salt, and the solvent was evaporated. The residue was purified through silica gel chromatography (hexane:ethyl acetate=3:1), and as a result the compound expressed by Structural Formula (9) (39.3 mg, 36%) was obtained.

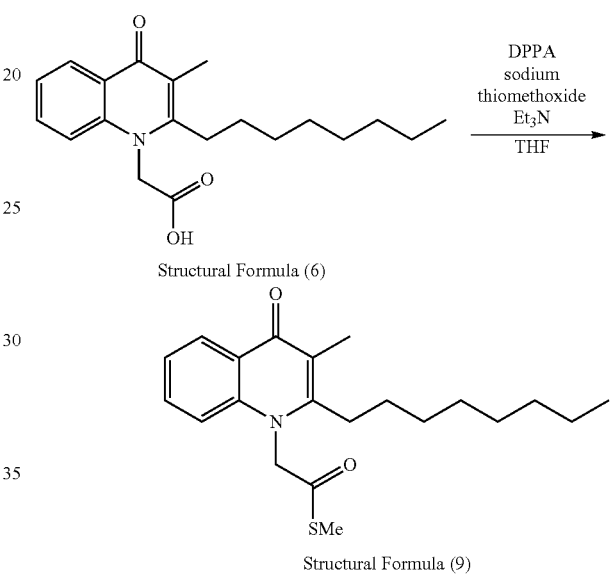

—Physico-Chemical Properties—
Physico-chemical properties of the compound expressed by Structural Formula (9) as follows.
(1) Appearance: colorless oily substance
(2) Molecular formula: $C_{21}H_{29}O_2NS$
(3) High resolution mass spectrometry (HRESI-MS)(m/z):
  Found: 360.1994 $(M+H)^+$
  Calcd: 360.1992 (as $C_{21}H_{30}O_2NS$)
(4) Infrared absorption spectrum:
Peaks of infrared absorption measured by the KBr tablet method are as follows.
$\nu_{max}(KBr)cm^{-1}$: 2924, 2852, 1687, 1614, 1594, 1542, 1193, 1028, 757, 558
(5) Proton nuclear magnetic resonance spectrum (400 MHz, $CDCl_3$):
  δ=0.88 (3H, t, J=6.4), 1.20-1.50 (10H, m), 1.60 (2H, br), 2.23 (3H, s), 2.33 (3H, s), 2.51-2.99 (2H, br), 5.01 (2H, br), 7.21 (1H, d, J=8.7), 7.34 (1H, dd, J=8.0, 6.6), 7.58 (1H, ddd, J=8.7, 6.6, 1.4), 8.47 (1H, dd, J=8.0, 1.4)
(6) $^{13}C$ nuclear magnetic resonance spectrum (100 MHz, $CDCl_3$):
  δ=11.38, 11.68, 14.06, 22.60, 28.16, 29.13, 29.16, 29.75, 31.03, 31.74, 55.95, 114.61, 117.94, 123.32, 127.29, 131.97, 132.02, 140.73, 150.65, 177.49, 196.82

Production Example 10

Production of the Compound Expressed by Structural Formula (10)

In the following manner, the compound expressed by the above Structural Formula (10) was produced through chemical synthesis.

—Production of the Compound Expressed by Structural Formula (10)—

The compound expressed by the above Structural Formula (6) (100 mg, 0.30 mmol) was suspended in THF (5 mL), and triethylamine (50.8 mL, 0.365 mmol) and DPPA (72.0 mL, 0.33 mmol) were added thereto under cooling with ice, and the mixture was further stirred under reflux for 1 hour. Sodium thiomethoxide (23.0 mg, 0.33 mmol) was added thereto, followed by stirring for another 1 hour. Ammonium chloride aqueous solution was added thereto, and the mixture was extracted with ethyl acetate. The organic layer was dried with Glauber's salt, and the solvent was evaporated. The residue was purified through silica gel chromatography (hexane:ethyl acetate=5:1), and as a result the compound expressed by Structural Formula (10) (48.6 mg, 43%) was obtained.

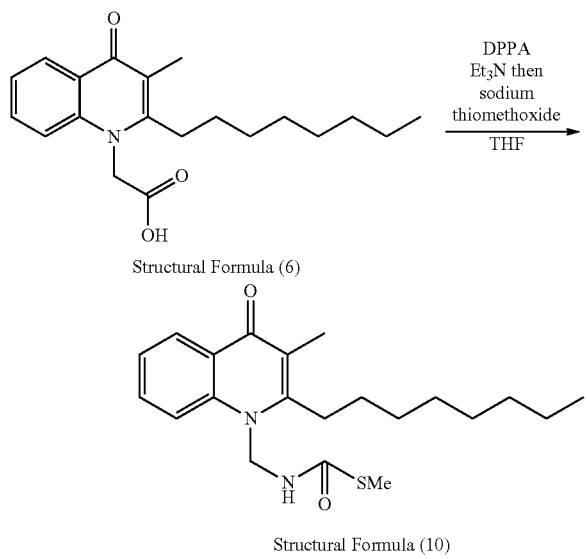

—Physico-Chemical Properties—

Physico-chemical properties of the compound expressed by Structural Formula (10) as follows.
(1) Appearance: colorless oily substance
(2) Molecular formula: $C_{21}H_{30}O_2N_2S$
(3) High resolution mass spectrometry (HRESI-MS)(m/z):
   Found: 397.1921 (M+Na)+
   Calcd: 397.1920 (as $C_{21}H_{30}O_2N_2NaS$)
(4) Infrared absorption spectrum:
Peaks of infrared absorption measured by the KBr tablet method are as follows.
   $\nu_{max}$(KBr)cm$^{-1}$: 3169, 2955, 2927, 1671, 1615, 1595, 1556, 1492, 1195, 1084, 760, 651
(5) Proton nuclear magnetic resonance spectrum (600 MHz, CDCl$_3$):
   δ=0.89 (3H, t, J=6.7), 1.22-1.45 (15H, m), 2.45 (2H, br), 2.46 (3H, s), 5.67 (2H, br), 7.24 (1H, ddd, J=7.9, 6.8, 1.0), 7.49 (1H, d, J=8.6), 7.59 (1H, ddd, J=8.6, 6.8, 1.4), 8.26 (1H, dd, J=7.9, 1.4), 8.78 (1H, br)

(6) $^{13}$C nuclear magnetic resonance spectrum (150 MHz, CDCl$_3$):
   δ=11.05, 12.22, 14.02, 22.59, 28.48, 29.11, 29.16, 29.73, 30.73, 31.77, 52.58, 115.46, 117.00, 123.24, 124.37, 126.89, 132.32, 139.56, 151.60, 168.61, 177.27

Production Example 11

Production of the Compound Expressed by Structural Formula (11)

In the following manner, the compound expressed by the above Structural Formula (11) was produced through chemical synthesis.

—Production of the Compound Expressed by Structural Formula (15)—

In an argon atmosphere, the compound expressed by the above Structural Formula (14) (1 equivalent) was dissolved in methylene chloride, and triethylamine (2 equivalents) was added thereto. Furthermore, octanoyl chloride (3.0 equivalents), which is an acid chloride, was added dropwise to the mixture in an ice bath, followed by stirring at room temperature. The reaction was terminated with 0.1N hydrochloric acid, and the mixture was extracted with methylene chloride, followed by washing with saturated sodium hydrogencarbonate aqueous solution and brine. The combined organic layer was dried with Glauber's salt, and then the solvent was evaporated. The residue was purified through silica gel chromatography (hexane:ethyl acetate), and as a result the compound expressed by Structural Formula (15) was obtained.

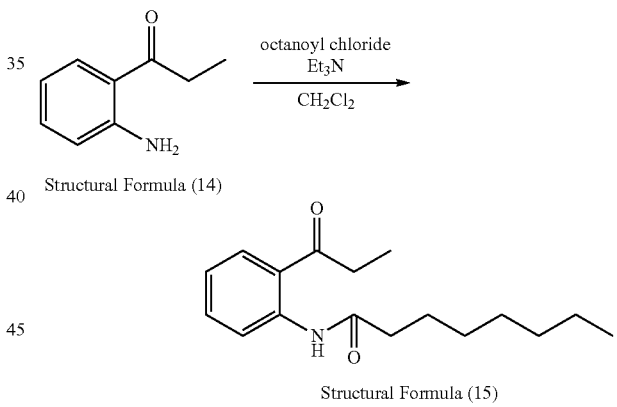

—Physico-Chemical Properties—

Physico-chemical properties of the compound expressed by Structural Formula (15) as follows.
(1) Appearance: colorless oily substance
(2) Molecular formula: $C_{17}H_{25}O_2N$
(3) High resolution mass spectrometry (HRESI-MS)(m/z):
   Found: 298.1777 (M+Na)+
   Calcd: 298.1778 (as $C_{17}H_{25}O_2NNa$)
(4) Infrared absorption spectrum:
Peaks of infrared absorption measured by the KBr tablet method are as follows.
   $\nu_{max}$(KBr)cm$^{-1}$: 3255, 2954, 2928, 1698, 754
(5) Proton nuclear magnetic resonance spectrum (400 MHz, CDCl$_3$):
   δ=0.87 (3H, t, J=6.6), 1.20-1.41 (11H, m), 1.74 (2H, m), 2.43 (2H, t, J=7.5), 3.08 (2H, q, J=7.1), 7.09 (1H, ddd, J=8.2, 7.1, 1.4), 7.53 (1H, ddd, J=8.4, 7.1, 1.4), 7.92 (1H, dd, J=8.2, 1.4), 8.77 (1H, dd, J=8.4, 1.4), 11.65 (1H, br)

(6) $^{13}$C nuclear magnetic resonance spectrum (100 MHz, CDCl$_3$):

δ=8.44, 14.05, 22.59, 25.53, 28.98, 29.16, 31.67, 33.13, 38.78, 120.83, 121.37, 122.11, 130.56, 134.82, 141.06, 172.78, 205.36

—Production of the Compound Expressed by Structural Formula (20)—

Sodium hydroxide (3.0 equivalents) was added to a dioxane solution of the compound expressed by the above Structural Formula (15) (1 equivalent) (0.1 M), and the mixture was stirred at 110° C. for 1 hour to 2 hours. The reaction solution was returned to room temperature, followed by addition of water, and also, 1N hydrochloric acid was added thereto until the pH thereof reached 7. Furthermore, when hexane was added and ultrasonic waves were applied thereto, solids precipitated. The solids were filtrated through aspiration, followed by washing sequentially with water and hexane. The washing was followed by drying, and as a result the compound expressed by Structural Formula (20) was obtained.

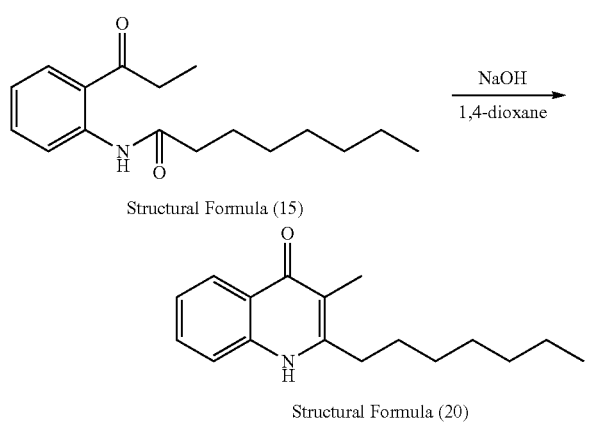

—Physico-Chemical Properties—

Physico-chemical properties of the compound expressed by Structural Formula (20) as follows.
(1) Appearance: white powder
(2) Melting point: 228° C.-231° C.
(3) Molecular formula: C$_{17}$H$_{23}$ON
(4) High resolution mass spectrometry (HRESI-MS)(m/z):
Found: 258.1853 (M+H)$^+$
Calcd: 258.1852 (as C$_{17}$H$_{24}$ON)
(5) Infrared absorption spectrum:
Peaks of infrared absorption measured by the KBr tablet method are as follows.
ν$_{max}$(KBr)cm$^{-1}$: 3061, 2954, 2925, 1637, 1608, 1556, 1504, 1188, 998, 754, 692
(6) Proton nuclear magnetic resonance spectrum (400 MHz, Methanol-d$_4$):
δ=0.88 (3H, t, J=6.6), 1.30-1.46 (8H, m), 1.65-1.73 (2H, m), 2.14 (3H, s), 2.78 (2H, t, J=7.7), 7.32 (1H, t, J=8.1), 7.52 (1H, d, m), 7.61 (1H, m), 8.21 (1H, d, J=8.2)
(7) $^{13}$C nuclear magnetic resonance spectrum (100 MHz, Methanol-d$_4$):
δ=10.84, 14.40, 23.68, 29.99, 30.16, 30.54, 32.91, 33.45, 116.16, 118.67, 124.38, 124.51, 126.15, 132.65, 140.55, 153.37, 179.53

—Production of the Compound Expressed by Structural Formula (11)—

In an argon atmosphere, the compound expressed by the above Structural Formula (20) (1.0 g, 3.89 mmol) was dissolved in THF (10 mL), and a THF solution of lithium t-butoxide (5.8 mL, 5.80 mmol) was added thereto, followed by stirring at room temperature for 20 minutes. Chloromethyl thiocyanate (6.7 mL, 38.9 mmol) was added dropwise thereto under cooling with ice, followed by further stirring at room temperature for 2 hours. The reaction was terminated by the addition of brine, and the mixture was extracted with ethyl acetate. The organic layer was dried with Glauber's salt, and then the residue was purified through silica gel chromatography (hexane:ethyl acetate=2:1), and as a result the compound expressed by Structural Formula (11) (330 mg, 26%) was obtained.

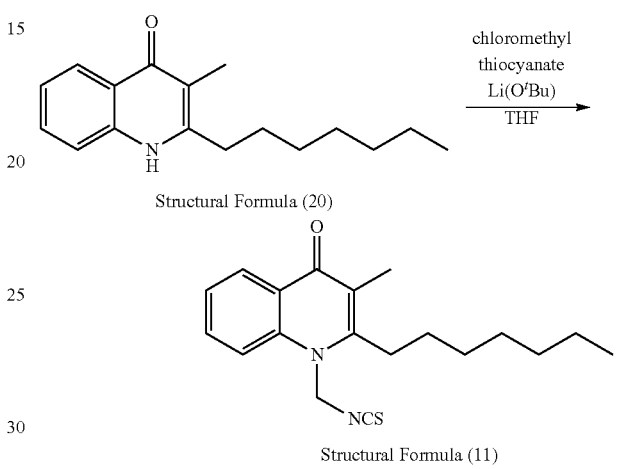

—Physico-Chemical Properties—

Physico-chemical properties of the compound expressed by Structural Formula (11) as follows.
(1) Appearance: yellow oily substance
(2) Molecular formula: C$_{19}$H$_{24}$ON$_2$S
(3) High resolution mass spectrometry (HRESI-MS)(m/z):
Found: 329.1682 (M+H)$^+$
Calcd: 329.1682 (as C$_{19}$H$_{25}$ON$_2$S)
(4) Infrared absorption spectrum:
Peaks of infrared absorption measured by the KBr tablet method are as follows.
ν$_{max}$(KBr)cm$^{-1}$: 2961, 2926, 2853, 2237, 1628, 1576, 1470, 1292, 1191, 987, 761, 693
(5) Proton nuclear magnetic resonance spectrum (400 MHz, CDCl$_3$):
δ=0.90 (3H, t, J=6.6), 1.23-1.71 (10H, m), 2.19 (3H, s), 2.84 (2H, m), 5.71 (2H, s), 7.38 (1H, ddd, J=8.0, 6.8, 0.9), 7.46 (1H, d, J=8.7), 7.68 (1H, ddd, J=8.7, 6.8, 1.6), 8.45 (1H, dd, J=8.0, 1.6)
(6) $^{13}$C nuclear magnetic resonance spectrum (100 MHz, CDCl$_3$):
δ=11.60, 14.05, 22.56, 28.59, 28.88, 29.76, 30.55, 31.66, 56.26, 114.42, 118.19, 123.83, 124.60, 127.31, 132.41, 139.86, 141.68, 149.60, 177.64

Production Example 12

Production of the Compound Expressed by Structural Formula (12)

In the following manner, the compound expressed by the above Structural Formula (12) was produced through chemical synthesis.

—Production of the Compound Expressed by Structural Formula (12)—

Acetonitrile (1.5 mL) was added to a mixture of the compound expressed by the above Structural Formula (11) (100 mg, 0.30 mmol) and sodium thiomethoxide (23.4 mg, 0.33 mmol), followed by stirring at room temperature for 20 minutes. Saturated sodium hydrogencarbonate aqueous solution was added thereto, and the mixture was extracted with ethyl acetate. The organic layer was dried with Glauber's salt, and then the residue was purified through silica gel chromatography (hexane:ethyl acetate=2:1), and as a result the compound expressed by Structural Formula (12) (31.7 mg, 27%) was obtained.

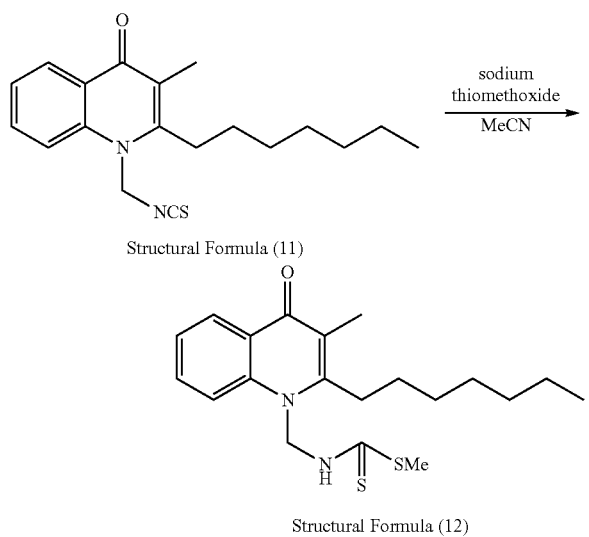

—Physico-Chemical Properties—

Physico-chemical properties of the compound expressed by Structural Formula (12) as follows.

(1) Appearance: yellow powder (2) Melting point: 167° C.-170° C.;

(3) Molecular formula: $C_{20}H_{28}ON_2S_2$ (4) High resolution mass spectrometry (HRESI-MS)(m/z):

Found: 399.1534 $(M+Na)^+$

Calcd: 399.1535 (as $C_{20}H_{28}ON_2NaS_2$)

(5) Infrared absorption spectrum:

Peaks of infrared absorption measured by the KBr tablet method are as follows.

$v_{max}(KBr)cm^{-1}$: 3119, 2958, 2918, 2850, 1619, 1598, 1538, 1282, 1199, 1105, 938, 764, 688

(6) Proton nuclear magnetic resonance spectrum (400 MHz, $CDCl_3$):

δ=0.86 (3H, t, J=6.6), 1.21-1.50 (13H, m), 2.22-2.58 (2H, br), 2.76 (3H, s), 5.68-6.41 (2H, br), 7.22 (1H, t, J=7.8), 7.44 (1H, d, J=8.7), 7.59 (1H, ddd, J=8.7, 7.8, 1.1), 8.15 (1H, d, J=7.8), 10.09 (1H, br)

(7) $^{13}C$ nuclear magnetic resonance spectrum (100 MHz, $CDCl_3$):

δ=10.74, 14.02, 18.01, 22.53, 28.29, 28.77, 29.64, 30.85, 31.59, 58.21, 115.93, 116.84, 123.54, 123.91, 126.35, 132.65, 139.39, 152.23, 177.13, 199.84

Production Example 13

Production of the Compound Expressed by Structural Formula (13)

In the following manner, the compound expressed by the above Structural Formula (13) was produced through chemical synthesis.

—Production of the Compound Expressed by Structural Formula (13)—

Acetonitrile (1.5 mL) was added to a mixture of the compound expressed by the above Structural Formula (11) (50.0 mg, 0.15 mmol) and sodium thiomethoxide (10.6 mg, 0.15 mmol), followed by stirring at room temperature for 20 minutes. Methyl iodide (8.5 mL, 0.17 mmol) was added thereto at room temperature, and the mixture was further stirred for 30 minutes. Saturated sodium hydrogencarbonate aqueous solution was added thereto, and the mixture was extracted with ethyl acetate. The organic layer was dried with Glauber's salt, and then the residue is purified through silica gel chromatography (hexane:ethyl acetate=2:1), and as a result the compound expressed by Structural Formula (13) (30.6 mg, 51%) was obtained.

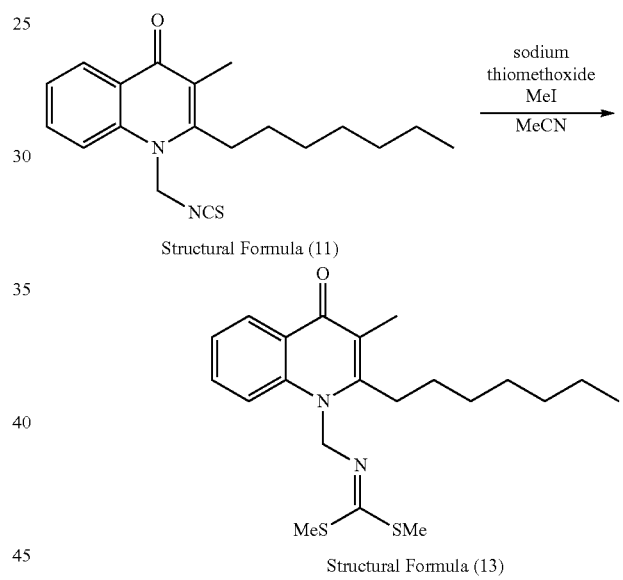

—Physico-Chemical Properties—

Physico-chemical properties of the compound expressed by Structural Formula (13) as follows.

(1) Appearance: white powder (2) Melting point: 92° C.-94° C.

(3) Molecular formula: $C_{21}H_{30}ON_2S_2$ (4) High resolution mass spectrometry (HRESI-MS)(m/z):

Found: 413.1689 $(M+Na)^+$

Calcd: 413.1692 (as $C_{21}H_{30}ON_2NaS_2$)

(5) Infrared absorption spectrum:

Peaks of infrared absorption measured by the KBr tablet method are as follows.

$v_{max}(KBr)cm^{-1}$: 2958, 2922, 2852, 1618, 1595, 1566, 1492, 1370, 1277, 1192, 1004, 769, 700

(6) Proton nuclear magnetic resonance spectrum (400 MHz, $CDCl_3$):

δ=0.89 (3H, t, J=6.8), 1.24-1.50 (8H, m), 1.64 (2H, m), 2.22 (3H, s), 2.28 (3H, s), 2.71 (3H, s), 2.77 (2H, m), 5.60 (2H, s), 7.31 (2H, m), 7.55 (1H, ddd, J=8.4, 7.1, 1.6), 8.46 (1H, dd, J=8.0, 1.6)

(7) $^{13}$C nuclear magnetic resonance spectrum (100 MHz, CDCl$_3$):

δ=11.50, 14.06, 14.75, 15.03, 22.61, 28.28, 28.92, 29.83, 30.66, 31.76, 63.75, 115.84, 116.97, 122.77, 124.81, 126.75, 131.27, 141.06, 151.35, 161.39, 177.54

Test Example 1: Anti-Cancer Activity In Vitro

The compounds expressed by Structural Formulas (1) to (13) obtained in the above Production Examples 1 to 13 were tested for anti-cancer activity In vitro in the following manner.

Cell Proliferation Test 1 (Human Stomach Cancer Cells MKN-74)

—Preparation of Cells—

Human stomach cancer cells MKN-74 (Riken Cell Bank) were cultured at 37° C. and 5% CO$_2$ in DMEM supplemented with 10% FBS (product of GIBCO Co.), 100 units/mL penicillin G (product of Invitrogen Co.), and 100 μg/mL streptomycin (product of Invitrogen Co.).

The above cancer cells were allowed to undergo gene transfer of Green fluorescence protein (GFP) expression vector, pEGFP-C1 (product of BD Biosciences Co.) using the Lipofectamine reagent (product of Invitrogen Co.), to thereby clone cells stably expressing GFP.

Normal stromal cells derived from the human stomach, Hs738 ((CRL-7869), ATCC) were cultured at 37° C. and 5% CO$_2$ in DMEM supplemented with 10% FBS, 100 units/mL penicillin G (product of Invitrogen Co.), 100 μg/mL streptomycin (product of Invitrogen Co.), 5 μg/mL insulin, 5 μg/mL transferrin (product of Wako Pure Chemical Industries Co.), 1.4 μM hydrocortisone (product of Sigma Co.), and 5 mg/mL basic-FGF (product of Pepro Tech Co.).

—Coculture Test—

The above normal stromal cells derived from the human stomach, Hs738 were dispersed at 5×10$^4$ cells/mL in DMEM containing 1% dialyzed serum, 5 μg/mL insulin, 5 μg/mL transferrine (product of Wako Pure Chemical Industries Co.), and 1.4 μM hydrocortisone (product of Sigma Co.), and were placed in a 96-well plate at 0.1 mL/well. Respective evaluation samples (the compounds expressed by Structural Formulas (1) to (13)) were added thereto at respective concentrations, followed by culturing at 37° C. and 5% CO$_2$ for 2 days.

Next, the above human stomach cancer cells MKN-74 were dispersed in DMEM at 5×10$^5$ cells/mL, and were placed at 10 μL/well in the plate in which the above normal stromal cells derived from the human stomach, Hs738 had been cultured, followed by further coculturing at 37° C. and 5% CO$_2$ for 3 days.

—Monoculture Test—

Only DMEM containing 1% dialyzed serum, 5 μg/mL insulin, 5 μg/mL transferrine (product of Wako Pure Chemical Industries Co.), and 1.4 μM hydrocortisone (product of Sigma Co.) was placed in a 96-well plate at 0.1 mL/well, and respective evaluation samples (the compounds expressed by Structural Formulas (1) to (13)) were added thereto at respective concentrations, followed by maintaining at 37° C. and 5% CO$_2$ for 2 days.

Next, the above human stomach cancer cells MKN-74 were dispersed in DMEM at 5×10$^5$ cells/mL, and were placed in the above plate at 10 μL/well, followed by further coculturing at 37° C. and 5% CO$_2$ for 3 days.

—Measurement of Cell Proliferation Rates—

Measurement of cell proliferation rates in the above coculture test and monoculture test was performed in the following manner.

The medium was removed from the wells of the above plate, and a cytolysis liquid (10 mM Tris-HCl [pH 7.4], 150 mM NaCl, 0.9 mM CaCl$_2$, and 1% Triton X-100) was added thereto at 0.1 mL/well to lyse the cells. The fluorescence intensity of GFP was measured at an excitation wavelength of 485 nm and a fluorescence wavelength of 538 nm, and the cell proliferation rates were calculated from the following formula. The results of the cell proliferation rates were used to calculate IC$_{50}$, and the calculated results are presented in Table 1.

Cell proliferation rate (%)=(Fluorescence intensity in the presence of the evaluation sample/Fluorescence intensity in the absence of the evaluation sample)×100

TABLE 1

| Compounds | Mono IC$_{50}$ (μg/mL) | Cocul IC$_{50}$ (μg/mL) |
| --- | --- | --- |
| Structural Formula (1) | 28.1 | 0.35 |
| Structural Formula (2) | 2.95 | 0.37 |
| Structural Formula (3) | >100 | 0.012 |
| Structural Formula (4) | >100 | 1.32 |
| Structural Formula (5) | >100 | 0.53 |
| Structural Formula (6) | 70.95 | 4.15 |
| Structural Formula (7) | >100 | 0.007 |
| Structural Formula (8) | >100 | >100 |
| Structural Formula (9) | 5.84 | 1.4 |
| Structural Formula (10) | 7.57 | 0.27 |
| Structural Formula (11) | 89.5 | 0.12 |
| Structural Formula (12) | 39.5 | 2.91 |
| Structural Formula (13) | 1.36 | 0.78 |

The values in Table 1 are average values in duplicate, and standard errors (SE) were 10% or less.

In Table 1, "Mono" presents the results of the monoculture test, and "Cocul" presents the results of the coculture test.

As presented in Table 1, each of the 13 compounds expressed by the above Structural Formulas (1) to (13) strongly inhibited proliferation of the stomach cancer cells MKN-74 cocultured with the stromal cells (Cocul) at lower concentrations (lower IC$_{50}$ values) as compared with the stomach cancer cells MKN-74 monocultured (Mono).

Test Example 2: Anti-Cancer Activity In Vivo

The compound expressed by Structural Formula (2) and the compound expressed by Structural Formula (13) obtained in the above Production Examples were tested for anti-cancer activity In vivo in the following manner.

Test Example 2-1: Human Stomach Cancer Cells MKN-74 Alone

BALB/c nu/nu nude mice (female, 5 weeks old, product of Charles River Co.) were bred under the SPF conditions.

Cultured human stomach cancer cells MKN-74 were trypsinized, and the human stomach cancer cells MKN-74 (8×10$^6$ cells) peeled off from the culture dish were dispersed in 0.3 mL DMEM containing 10% FBS and mixed with 0.5 mL growth factor-reduced Matrigel (product of BD Biosciences Co.).

The above mixed cell liquid (0.1 mL) (cancer cells: 1×10$^6$ cells) was subcutaneously inoculated to the left groin region of the above mice.

The compound expressed by the Structural Formula (2) or the compound expressed by the Structural Formula (13) was intravenously administered for a predetermined period, and tumor formed under the skin was cut out and measured for weight. Note that, the administration dose of the compound expressed by the Structural Formula (2) or the compound expressed by the Structural Formula (13) was 12.5 mg/kg per administration day.

Also, a tumor volume was calculated from the following formula referring to the above NPL 1.

Tumor volume (mm$^3$)=(major axis×minor axis$^2$)/2

Note that, as controls, those to which physiological saline (vehicle) was administered instead of the compound expressed by the Structural Formula (2) or the compound expressed by the Structural Formula (13) were tested in the same manner.

Test Example 2-2: Human Stomach Cancer Cells MKN-74 and Normal Stromal Cells Derived from the Human Stomach, Hs738

A test was performed in the same manner as in Test Example 2-1 except that the use of the human stomach cancer cells MKN-74 alone in Test Example 2-1 was changed to use of the human stomach cancer cells MKN-74 and the normal stromal cells derived from the human stomach, Hs738.

Note that, a cell liquid and inoculation of the cell liquid to mice were as follows.

Cultured human stomach cancer cells MKN-74 and normal stromal cells derived from the human stomach, Hs738 were respectively trypsinized to be peeled off from the culture dishes. The above human stomach cancer cells MKN-74 (8×10$^6$ cells) and the above normal stromal cells derived from the human stomach, Hs738 (8×10$^6$ cells) were dispersed in 0.3 mL DMEM containing 10% FBS and mixed with 0.5 mL growth factor-reduced Matrigel (product of BD Biosciences Co.).

The above mixed cell liquid (0.1 mL) (a mixture of cancer cells: 1×10$^6$ cells, and stromal cells: 1×10$^6$ cells) was subcutaneously inoculated to the left groin region of the above mice.

The results of the above Test Example 2 are presented in FIGS. 1A to 1D.

Figure 1B:
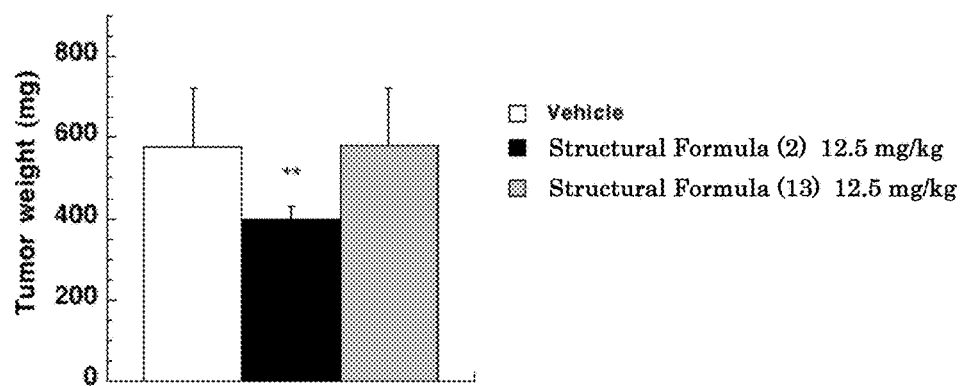
FIG. 1B is a graph of changes in tumor weight in Test Example 2-1 (Day 21 from inoculation of tumor).
Figure 1C:
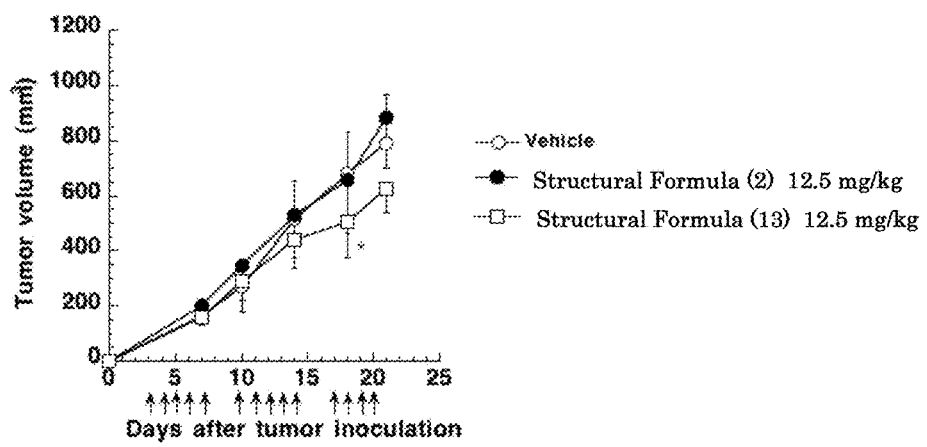
FIG. 1C is a graph of changes in tumor volume in Test Example 2-2.
Figure 1D:
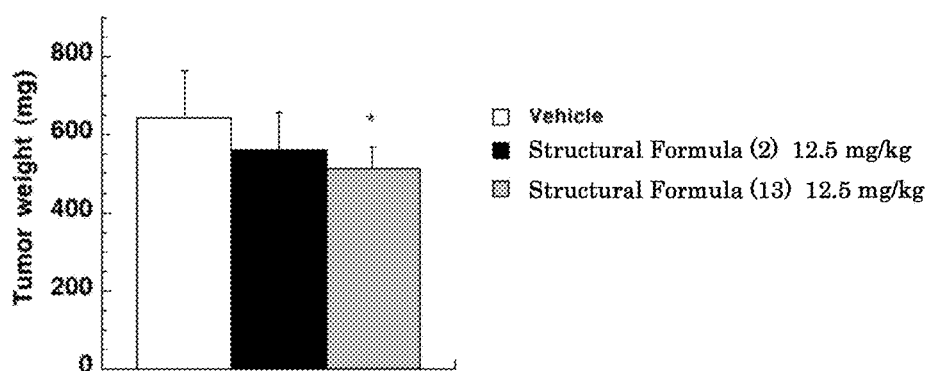
FIG. 1D is a graph of changes in tumor weight in Test Example 2-2 (Day 21 from inoculation of tumor).

FIG. 1A indicates changes in tumor volume in Test Example 2-1, FIG. 1B indicates changes in tumor weight in Test Example 2-1 (Day 21 from inoculation of tumor), FIG. 1C indicates changes in tumor volume in Test Example 2-2, and FIG. 1D indicates changes in tumor weight in Test Example 2-2 (Day 21 from inoculation of tumor).

In FIGS. 1A and 1C, "white circle" indicates the results of "vehicle", "black circle" indicates the results obtained "when the administration dose of the compound expressed by Structural Formula (2) was 12.5 mg/kg", and "white square" indicates the results obtained "when the administration dose of the compound expressed by Structural Formula (13) was 12.5 mg/kg". Also, in FIGS. 1A and 1C, "arrow" indicates the day when the compound expressed by Structural Formula (2) or the compound expressed by Structural Formula (13) was administered.

FIGS. 1B and 1D, "white" indicates the results of "vehicle", "black" indicates the results obtained "when the administration dose of the compound expressed by Structural Formula (2) was 12.5 mg/kg", and "gray" indicates the results obtained "when the administration dose of the compound expressed by Structural Formula (13) was 12.5 mg/kg".

The values in FIGS. 1A to 1D are average values in 5 mice and standard deviations (SD), and * indicates $P<0.05$ and ** indicates $P<0.01$.

As presented in FIGS. 1A to 1D, in the case of the human stomach cancer cells MKN-74 alone, significant suppression was observed by intravenous administration of the compound expressed by Structural Formula (2) at 12.5 mg/kg.

Meanwhile, in the case of the tumor transplanted together with the normal stromal cells derived from the human stomach, Hs738, significant suppression was observed by intravenous administration of the compound expressed by Structural Formula (13) at 12.5 mg/kg.

Test Example 3: Acute Toxicity Test

ICR mice (female, 4 weeks old, product of Charles River Co.) were bred under the SPF conditions.

As evaluation samples, the compounds expressed by the above Structural Formulas (1) to (13) were intravenously administered thereto, and the mice were observed for 2 weeks. One half of the administration dose at which the mice were recognized to be dead or have serious toxicity for the observation period of 2 weeks was defined as the maximum tolerated dose (MTD) in the present experiment. The results are presented in Table 2.

TABLE 2

| Compounds | MTD (mg/kg) |
|---|---|
| Structural Formula (1) | >50.0 |
| Structural Formula (2) | >50.0 |
| Structural Formula (3) | 1.56 |
| Structural Formula (4) | 25 |
| Structural Formula (5) | 6.25 |
| Structural Formula (6) | >50.0 |
| Structural Formula (7) | 6.25 |
| Structural Formula (8) | 12.5 |
| Structural Formula (9) | >50.0 |
| Structural Formula (10) | >50.0 |
| Structural Formula (11) | 6.25 |
| Structural Formula (12) | >50.0 |
| Structural Formula (13) | >50.0 |

From the results of the above Table 2, the MTD was found to be 50 mg/kg or higher when the compound expressed by the above Structural Formula (1), the compound expressed by the above Structural Formula (2), the compound expressed by the above Structural Formula (6), the compound expressed by the above Structural Formula (9), the compound expressed by the above Structural Formula (10), the compound expressed by the above Structural Formula (12), and the compound expressed by the above Structural Formula (13) were intravenously administered.

Test Example 4: Anti-Bacterial Activity

The compound expressed by the above Structural Formula (2), the compound expressed by the above Structural Formula (3), the compound expressed by the above Structural Formula (4), the compound expressed by the above Structural Formula (5), the compound expressed by the above Structural Formula (6), the compound expressed by the above Structural Formula (8), the compound expressed by the above Structural Formula (11), the compound expressed by the above Structural Formula (12), and the compound expressed by the above Structural Formula (13) were tested for anti-bacterial activity in the following manner.

Note that, as comparisons, clarithromycin and ampicillin (ABPC) were tested in the same manner.

Test Example 4-1: Measurement of MIC for *Helicobacter pylori*

Each of the above compounds was measured for minimum inhibitory concentration (MIC) for *Helicobacter pylori*.

*Helicobacter pylori* JCM12093 strain and *H. pylori* JCM12095 strain each were statically cultured in a HP medium (brain heart infusion broth (product of Becton, Dickinson Co.) supplemented with 10% fetal bovine serum (product of Life Technologies Co.)) for 144 hours at 37° C. under microaerobic culture conditions (microaerobic conditions ($N_2:O_2:CO_2=85:5:10$)).

After completion of the culturing, the culture was suspended with the HP medium and diluted so that *Helicobacter pylori* was $2\times10^6$ CFU/mL to $9\times10^6$ CFU/mL.

Each of the test samples (each of the above compounds, clarithromycin, and ampicillin) was prepared with the HP medium to have a concentration of 256 mg/L. From this concentration, the test sample was 2-fold diluted serially in 15 steps to 0.0078 mg/L.

The above-diluted culture was added at 50 μL/well to 50 μL/well of the HP medium containing each of the test samples at the above concentrations, and was statically cultured for 144 hours at 37° C. under microaerobic culture conditions (microaerobic conditions ($N_2:O_2:CO_2=85:5:10$)). After completion of the culturing, the presence or absence of proliferation of each bacterium was visually determined based on turbidity, and the MIC for each bacterial strain was obtained. The results are presented in Table 3.

Test Example 4-2: Measurement of MIC for *Staphylococcus aureus* and *Escherichia coli*

Each of the above compounds was measured for minimum inhibitory concentration (MIC) for *Staphylococcus aureus* and *Escherichia coli*.

*Staphylococcus aureus* FDA209P strain and *Escherichia coli* K-12 strain each were cultured under shaking in a nutrient broth medium (polypeptone (product of NIHON PHARMACEUTICAL Co.) 1%, fish extract for bacteria (product of KYOKUTO PHARMACEUTICAL INDUSTRIAL Co.) 1%, and sodium chloride 0.2%) at 37° C. overnight.

After completion of the culturing, the culture was diluted with the nutrient broth medium so that the bacteria were $2\times10^6$ CFU/mL to $9\times10^6$ CFU/mL.

Each of the test samples (each of the above compounds, clarithromycin, and ampicillin) was prepared with the nutrient broth medium to have a concentration of 256 mg/L. From this concentration, the test sample was 2-fold diluted serially in 11 steps to 0.125 mg/L.

The above-diluted culture was added at 50 μL/well to 50 μL/well of the nutrient broth medium containing each of the test samples at the above concentrations, and was statically cultured at 37° C. overnight. After completion of the culturing, the presence or absence of proliferation of each bacterium was visually determined based on turbidity, and the MIC for each bacterial strain was obtained. The results are presented in Table 3.

Test Example 4-3: Measurement of MIC for *Enterococcus faecalis*

Each of the above compounds was measured for minimum inhibitory concentration (MIC) for *Enterococcus faecalis*.

*Enterococcus faecalis* JCM5803 strain was cultured under shaking in a heart infusion broth medium (product of Becton, Dickinson Co.) at 37° C. overnight.

After completion of the culturing, the culture was diluted with the heart infusion broth medium so that the bacteria were $2\times10^4$ CFU/mL to $9\times10^4$ CFU/mL.

Each of the test samples (each of the above compounds, clarithromycin, and ampicillin) was prepared with the heart infusion broth medium to have a concentration of 256 mg/L. From this concentration, the test sample was 2-fold diluted serially in 11 steps to 0.125 mg/L.

The above-diluted culture was added at 50 μL/well to 50 μL/well of the heart infusion broth medium containing each of the test samples at the above concentrations, and was statically cultured at 37° C. for 18 hours.

After completion of the culturing, the presence or absence of proliferation of each bacterium was visually determined based on turbidity, and the MIC for each bacterial strain was obtained. The results are presented in Table 3.

Test Example 4-4: Measurement of MIC for *Haemophilus influenza*

Each of the above compounds was measured for minimum inhibitory concentration (MIC) for *Haemophilus influenza*.

*Haemophilus influenza* T-196 strain and *H. influenza* ARD476 strain each were statically cultured in a HI medium (Muller Hinton medium (product of Becton, Dickinson Co.) supplemented with 5% Fildes enrichment (product of Becton, Dickinson Co.)) at 37° C. overnight under aerobic conditions containing 5% carbon dioxide gas.

After completion of the culturing, the culture was suspended with the HI medium and diluted so that each *Haemophilus influenza* strain was $2\times10^6$ CFU/mL to $9\times10^6$ CFU/mL.

Each of the test samples (each of the above compounds, clarithromycin, and ampicillin) was prepared with the HI medium to have a concentration of 256 mg/L. From this concentration, the test sample was 2-fold diluted serially in 11 steps to 0.125 mg/L.

The above-diluted culture was added at 50 μL/well to 50 μL/well of the HI medium containing each of the test samples at the above concentrations, and was statically cultured for 18 hours at 37° C. under aerobic conditions containing 5% carbon dioxide gas.

After completion of the culturing, the presence or absence of proliferation of each bacterium was visually determined based on turbidity, and the MIC for each bacterial strain was obtained. The results are presented in Table 3.

TABLE 3

| MIC (μg/ml) | *Helicobacter pylori* JCM 12093 | *H. pylori* JCM 12095 | *Staphylococcus aureus* FDA209P | *Enterococcus faecalis* JCM5803 | *Escherichia coli* K-12 | *Haemophilus influenzae* T-196 | *H. influenzae* ARD476 |
|---|---|---|---|---|---|---|---|
| Structural Formula (2) | 1 | 0.5 | >128 | >128 | 128 | 64 | 64 |
| Structural Formula (3) | 0.008 | 0.016 | >128 | >128 | >128 | >128 | >128 |

TABLE 3-continued

| MIC (µg/ml) | Helicobacter pylori JCM 12093 | H. pylori JCM 12095 | Staphylococcus aureus FDA209P | Enterococcus faecalis JCM5803 | Escherichia coli K-12 | Haemophilus influenzae T-196 | H. influenzae ARD476 |
| --- | --- | --- | --- | --- | --- | --- | --- |
| Structural Formula (4) | 0.5 | 0.25 | 128 | >128 | 128 | 64 | 128 |
| Structural Formula (5) | 2 | 2 | >128 | >128 | >128 | >128 | >128 |
| Structural Formula (6) | 1 | 0.25 | 128 | >128 | 128 | 128 | 128 |
| Structural Formula (8) | 1 | 0.5 | >128 | >128 | >128 | 64 | 64 |
| Structural Formula (11) | 0.016 | 0.016 | 4 | >128 | >128 | >128 | >128 |
| Structural Formula (12) | 0.03 | 0.06 | >128 | >128 | >128 | >128 | >128 |
| Structural Formula (13) | 2 | 2 | 4 | >128 | >128 | >128 | >128 |
| Clarithromycin | 0.008 | 0.008 | <0.125 | 0.5 | 16 | 8 | 4 |
| ABPC | 0.25 | 0.13 | <0.125 | 0.5 | 4 | 0.5 | 64 |

As presented in Table 3, each of the above compounds exhibited anti-*Helicobacter pylori* activity. Among them, the compound expressed by Structural Formula (3), the compound expressed by Structural Formula (11), and the compound expressed by Structural Formula (12) exhibited anti-*Helicobacter pylori* activity at low concentrations.

Meanwhile, each of the above compounds exhibited low anti-bacterial activity against other general bacteria causing infectious diseases.

INDUSTRIAL APPLICABILITY

Since the compounds expressed by Structural Formulas (1) to (13) of the present invention have excellent anti-cancer effects, or excellent anti-*Helicobacter pylori* activity, and are highly safe compounds, they can be suitably used as an active ingredient of a pharmaceutical composition, an anti-cancer agent, an anti-*Helicobacter pylori* agent, and the like.

The invention claimed is:

1. A method for producing a compound expressed by Structural Formula (3)

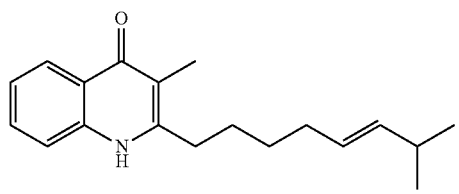

Structural Formula (3)

the method comprising:

reacting a compound expressed by Structural Formula (17)

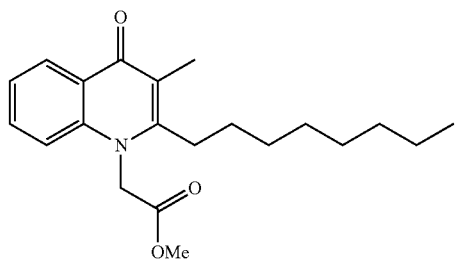

Structural Formula (17)

with a hydroxide of an alkali metal or a hydroxide of an alkaline earth metal, or both thereof.

2. A method for producing a compound expressed by Structural Formula (5)

Structural Formula (5)

the method comprising:

reacting a compound expressed by Structural Formula (21)

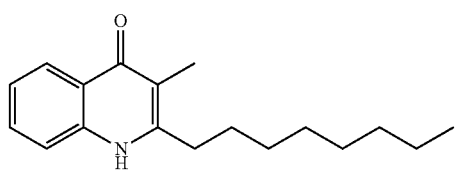

Structural Formula (21)

with an alkoxide of an alkali metal, a carbonic acid salt of an alkali metal or a hydride of an alkali metal, or any combination thereof, to thereby obtain a reaction product, and reacting the reaction product and methyl bromoacetate, where in the Structural Formula (5), Me denotes a methyl group.

3. A method for producing a compound expressed by Structural Formula (6)

Structural Formula (6)

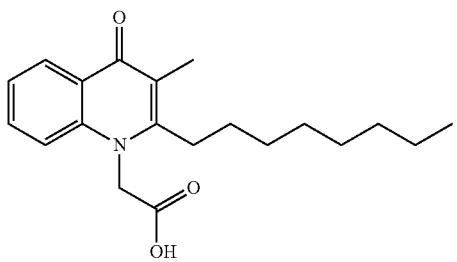

the method comprising:

reacting a compound expressed by Structural Formula (5)

Structural Formula (5)

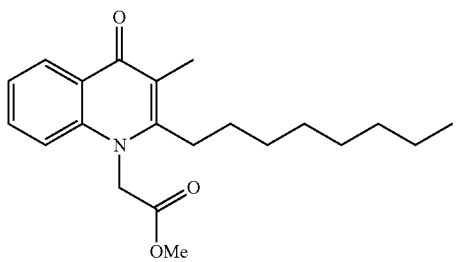

with a hydroxide of an alkali metal or a hydroxide of an alkaline earth metal, or both thereof, to thereby obtain a reaction product, and acidifying a pH of the reaction product, where in the Structural Formula (5), Me denotes a methyl group.

4. A method for producing a compound expressed by Structural Formula (7)

Structural Formula (7)

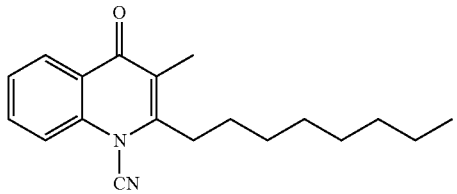

the method comprising:

reacting a compound expressed by Structural Formula (21)

Structural Formula (21)

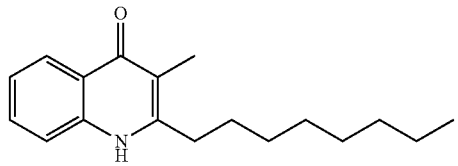

with an alkoxide of an alkali metal or a hydride of an alkali metal, or both thereof, to thereby obtain a reaction product, and reacting the reaction product and cyanogen bromide.

5. A method for producing a compound expressed by Structural Formula (9)

Structural Formula (9)

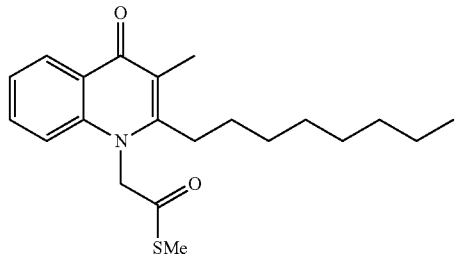

the method comprising:

reacting a compound expressed by Structural Formula (6)

Structural Formula (6)

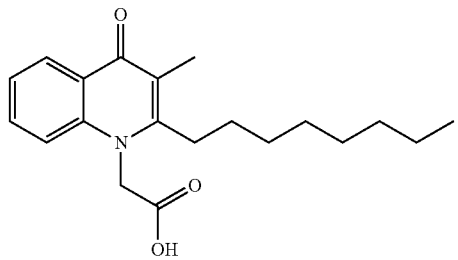

with a tertiary amine or a pyridine, or both thereof, diphenylphosphoryl azide, and sodium thiomethoxide, where in the Structural Formula (9), Me denotes a methyl group.

6. A method for producing a compound expressed by Structural Formula (10)

Structural Formula (10)

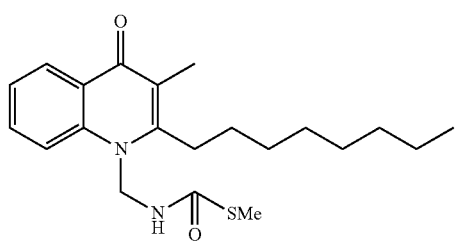

the method comprising:
reacting a compound expressed by Structural Formula (6)

Structural Formula (6)

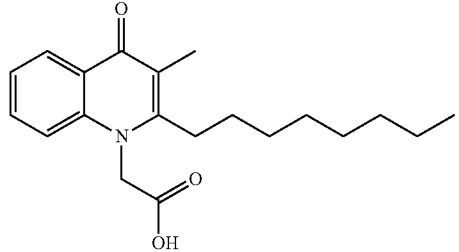

with a tertiary amine or a pyridine, or both thereof, and diphenylphosphoryl azide, to thereby obtain a reaction product, and reacting the reaction product and sodium thiomethoxide,
where in the Structural Formula (10), Me denotes a methyl group.

7. A method for producing a compound expressed by Structural Formula (11)

Structural Formula (11)

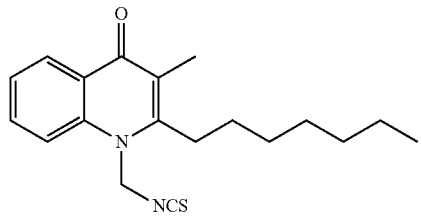

the method comprising:
reacting a compound expressed by Structural Formula (20)

Structural Formula (20)

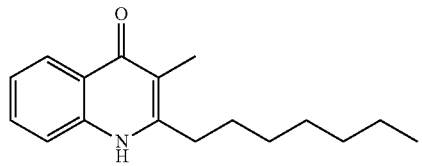

with an alkoxide of an alkali metal or a hydride of an alkali metal, or both thereof, to thereby obtain a reaction product, and reacting the reaction product and chloromethyl thiocyanate.

8. A method for producing a compound expressed by Structural Formula (13)

Structural Formula (13)

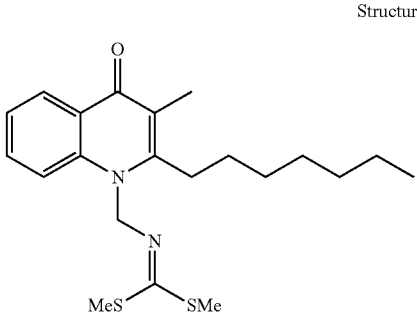

the method comprising:
reacting a compound expressed by Structural Formula (11)

Structural Formula (11)

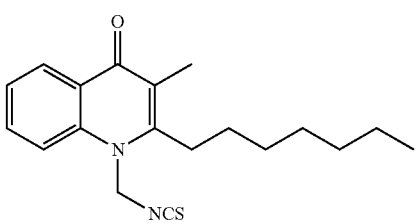

with sodium thiomethoxide in the presence of acetonitrile, to thereby obtain a reaction product, and reacting the reaction product and a methylating agent,
where in the Structural Formula (13), Me denotes a methyl group.

* * * * *